(12) United States Patent
Shetty et al.

(10) Patent No.: US 9,506,167 B2
(45) Date of Patent: Nov. 29, 2016

(54) METHODS AND SYSTEMS FOR CELL STATE QUANTIFICATION

(75) Inventors: Reshma Shetty, Boston, MA (US); Thomas F. Knight, Jr., Belmont, MA (US); Randall D. Rettberg, Concord, MA (US)

(73) Assignee: GINKGO BIOWORKS, INC., Boston, MA (US)

( * ) Notice: Subject to any disclaimer, the term of this patent is extended or adjusted under 35 U.S.C. 154(b) by 529 days.

(21) Appl. No.: 13/560,527

(22) Filed: Jul. 27, 2012

(65) Prior Publication Data

US 2013/0029879 A1    Jan. 31, 2013

Related U.S. Application Data

(60) Provisional application No. 61/513,469, filed on Jul. 29, 2011.

(51) Int. Cl.
 *C12N 15/70* (2006.01)
 *C12N 15/74* (2006.01)
 *C40B 40/08* (2006.01)

(52) U.S. Cl.
 CPC .............. *C40B 40/08* (2013.01); *C12N 15/70* (2013.01); *C12N 15/74* (2013.01)

(58) Field of Classification Search
 None
 See application file for complete search history.

(56) References Cited

U.S. PATENT DOCUMENTS

| 2006/0141528 A1 | 6/2006 | Aebersold et al. |
| 2007/0233394 A1 | 10/2007 | Kangas et al. |
| 2013/0053544 A1* | 2/2013 | Howarth ........................ 530/350 |

FOREIGN PATENT DOCUMENTS

| WO | 2008/146100 | 12/2008 |
| WO | 2009/141141 | 11/2009 |
| WO | 2009/141310 | 11/2009 |
| WO | 2010/136706 | 12/2010 |

OTHER PUBLICATIONS

Yus et al., "Impact of genome reduction on bacterial metabolism and its regulation," Science. 326(5957): 1263-1268 (2009).
Zhang et al., "Integrating multiple 'omics' analysis for microbial biology: application and methodologies," Microbiology. 156(Pt 2): 287-301 (2010).
Allam et al., "Targeted homologous recombination in *Mycoplasma mycoides* subsp. capri is enhanced by inclusion of heterologous recA," Appl Environ Microbiol. (2010).
Bennett et al., "Absolute quantitation of intracellular metabolite concentrations by an isotope ratio-based approach," Nat Protoc. 3(8): 1299-311 (2008).
Bondarenko and Chelius, "Quantitative profiling of proteins in complex mixtures using liquid chromatography and mass spectrometry," J Proteome Res. 1: 317-323 (2002).
Chan et al., "Refactoring bacteriophage T7," Mol Syst Biol. 1: 2005.0018 (2005).
Chang et al., "BRENDA, AMENDA and FRENDA the enzyme information system: new content and tools in 2009," Nucleic Acids Res. 37(Database issue):D588-592 (2009).
Cech and Enke, "Relating electrospray ionization response to non-polar character of small peptides," Anal Chem. 72 (13): 2717-2723 (2000).
Cech et al., "Predicting electrospray response from chromatographic retention time," Anal Chem. 73(2): 208-213 (2001).
Cottingham, K.,"Overcoming ionization suppression in electrospray," Anal Chem. 78: 5239 (2006).
Datta et al., "Identification and analysis of recombineering functions from Gram-negative and Gram-positive bacteria and their phages," Proc Natl Acad Sci U S A. 105(5): 1626-1631 (2008).
Deutsch E et al., "PeptideAtlas: a resource for target selection for emerging targeted proteomics workflows," EMBO Rep. 9(5): 429-434 (2008).
Ellis et al., "High efficiency mutagenesis, repair, and engineering of chromosomal DNA using single-stranded oligonucleotides," Proc Natl Acad Sci U S A. 98 (12): 6742-6746 (2001).
Ficarro et al., "Improved electrospray ionization efficiency compensates for diminished chromatographic resolution and enables proteomics analysis of tyrosine signaling in embryonic stem cells," Anal Chem. 81: 3440-3447 (2009).
Frahm et al., "Achieving augmented limits of detection for peptides with hydrophobic alkyl tags," Anal Chem. 79(11): 3989-3995 (2007).
French et al., "Large-scale transposon mutagenesis of Mycoplasma pulmonis," Mol Microbiol. 69(1): 67-76 (2008).
Fusaro V et al., "Prediction of high-responding peptides for targeted protein assays by mass spectrometry," Nat Biotechnol. 27: 190-198 (2009).
Gibbons et al., "Benchmarking next-generation transcriptome sequencing for functional and evolutionary genomics," Mol Biol Evol. 26(12): 2731-2744. (2009).

(Continued)

*Primary Examiner* — Jim Ketter
(74) *Attorney, Agent, or Firm* — Greenberg Traurig, LLP; Fang Xie

(57) ABSTRACT

Systems, methods, libraries, kits, and computer software tools are provided for designing and producing engineered cells. Such engineered cells can be used for cell state quantification, such as genome, transcriptome and/or proteome quantification. In one aspect, an engineered cell having a plurality of artificially designed oligonucleotides introduced into the genome of the cell is provided. The oligonucleotides are each located in proximity of a gene of interest encoding a protein of interest, and are different from one another. The oligonucleotides can each encode a unique peptide tag for each protein of interest, wherein each peptide tag has a unique quantitatively measurable value such as mass-to-charge ratio which can be quantified by a mass spectrometer. The engineered cell is capable of expressing a plurality of proteins of interest each fused to its corresponding unique peptide tag, wherein each peptide tag is capable of being released therefrom.

23 Claims, 15 Drawing Sheets

(56) References Cited

OTHER PUBLICATIONS

Gibson et al., "Complete chemical synthesis, assembly, and cloning of a Mycoplasma genitalium genome," Science. 319(5867): 1215-1220 (2008).
Gibson et al., "One-step assembly in yeast of 25 overlapping DNA fragments to form a complete synthetic Mycoplasma genitalium genome," Proc Natl Acad Sci U S A. 105(51): 20404-20409 (2008).
Gibson et al., "Creation of a bacterial cell controlled by a chemically synthesized genome," Science. 329(5987): 52-56 (2010).
Glass et al., "Essential genes of a minimal bacterium," Proc Natl Acad Sci U S A. 103(2): 425-430 (2006).
Güell et al., "Transcriptome complexity in a genome-reduced bacterium," Science. 326(5957): 1268-1271 (2009).
Jewett and Forster, "Update on designing and building minimal cells," Curr Opin Biotechnol. 21(5): 697-703 (2010).
Kast P., "pKSS—a second-generation general purpose cloning vector for efficient positive selection of recombinant clones," Gene. 138(1-2): 109-114 (1994).
King et al., "Mechanistic investigation of ionization suppression in electrospray ionization," J Am Soc Mass Spectrom. 11: 942-950 (2000).
Kirkpatrick et al., "The absolute quantification strategy: a general procedure for the quantification of proteins and post-translational modifications," Methods. 35: 265-273. (2005).
Kiyonami et al., "Increased selectivity, analytical precision, and throughput in targeted proteomics," Mol Cell Proteomics. (2010).
Knight T., "BBF RFC10: Draft Standard for BioBrick™ biological parts," DOI: 1721.1/45138, 2007.
Kühner et al., "Proteome organization in a genome-reduced bacterium," Science. 26(5957): 1235-1240 (2009).
Kuster et al., "Scoring proteomes with proteotypic peptide probes," Nat Rev Mol Cell Biol. 6(7): 577-583 (2005).
Lartigue et al., "Creating bacterial strains from genomes that have been cloned and engineered in yeast," Science. 2325(5948): 1693-1696 (2009).
Mallick et al., "Computational prediction of proteotypic peptides for quantitative proteomics," Nat Biotechnol. 25(1): 125-131 (2007).
Muyrers et al., "ET recombination: DNA engineering using homologous recombination in *E. coli*," Methods Mol Biol. 256: 107-121 (2004).
Nagalakshmi et al., "The transcriptional landscape of the yeast genome defined by RNA sequencing," Science. 320 (5881): 1344-1349 (2008).
Oliver et al., "Deep RNA sequencing of L. monocytogenes reveals overlapping and extensive stationary phase and sigma B-dependent transcriptomes, including multiple highly transcribed noncoding RNAs," BMC Genomics. 10: 641 (2009).
Ong et al., "Stable isotope labeling by amino acids in cell culture, SILAC, as a simple and accurate approach to expression proteomics," Mol Cell Proteomics. 1(5): 376-386 (2002).
Ong et al., "Stable isotope labeling by amino acids in cell culture for quantitative proteomics," Methods Mol Biol. 359: 37-52 (2007).
Pavelka et al., "Statistical similarities between transcriptomics and quantitative shotgun proteomics data," Mol Cell Proteomics. 7: 631-644 (2008).
Picot et al., "Full dynamic range proteome analysis of S. cerevisiae by targeted proteomics," Cell. 138(4): 795-806 (2009).
Pósfai et al., "Emergent properties of reduced-genome *Escherichia coli*," Science. 312(5776): 1044-1046 (2006).
Reznikoff et al., "Tn5 as a molecular genetics tool: In vitro transposition and the coupling of in vitro technologies with in vivo transposition," Methods Mol Biol. 260: 83-96 (2004).
Sharan et al., "Recombineering: a homologous recombination-based method of genetic engineering," Nat Protoc. 4(2): 206-223. (2009).
Suthers et al., "A genome-scale metabolic reconstruction of Mycoplasma genitalium, iPS189," PLoS Comput Biol. 5 (2): e1000285 (2009).
Swingle et al., "Oligonucleotide recombination in Gram-negative bacteria," Mol Microbiol. 75(1): 138-48. (2010).
Vickers et al., "Grand Challenge Commentary: Chassis cells for industrial biochemical production," Nat Chem Biol. 6 (12): 875-877. (2010).
Wang et al., "Programming cells by multiplex genome engineering and accelerated evolution," Nature. 460(7257): 894-898 (2009).
Webb-Robertson et al., "A support vector machine model for the prediction of proteotypic peptides for accurate mass and time proteomics," Bioinformatics. 26: 1677-1683 (2010).
Wienkoop et al., "Targeted proteomics for Chlamydomonas reinhardtii combined with rapid subcellular protein fractionation, metabolomics and metabolic flux analyses," Mol Biosyst. 6(6): 1018-1031 (2010).
Wolters et al., "An automated multidimensional protein identification technology for shotgun proteomics," Anal Chem. 73: 5683-5690 (2001).
Yuan et al., "Kinetic flux profiling for quantitation of cellular metabolic fluxes," Nat Protoc. 3(8): 1328-1340 (2008).
Xu, et al., "The genomic sequence of the Chinese hamster ovary (CHO)-K1 cell line", Nature Biotechnology, vol. 29, pp. 735-741 (2011).

* cited by examiner

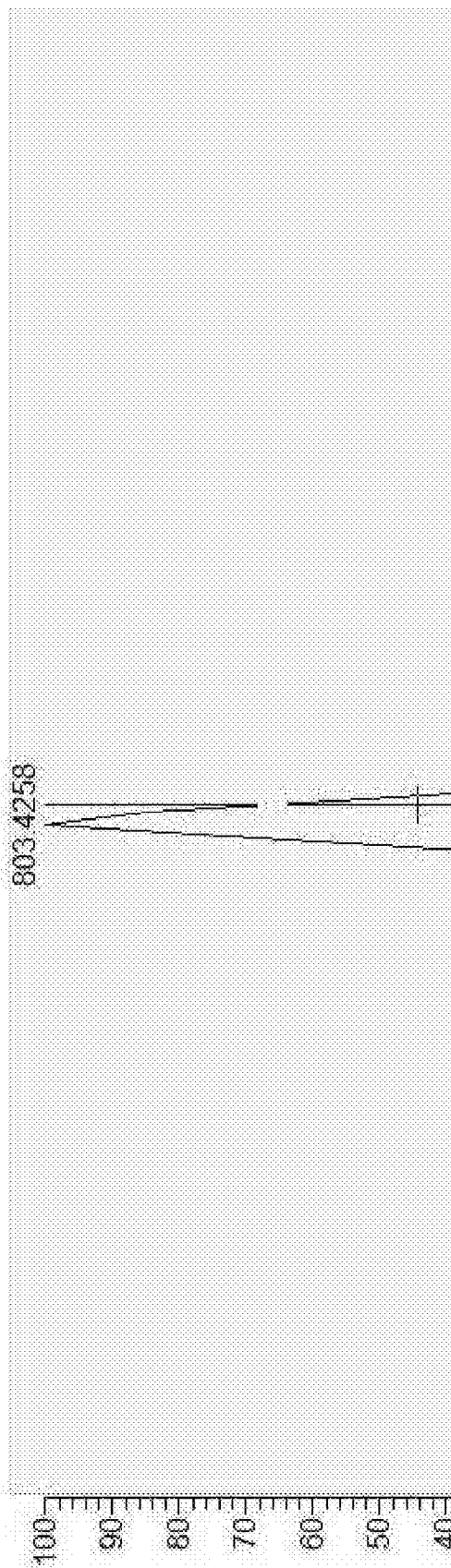

METHODS AND SYSTEMS FOR CELL STATE QUANTIFICATION

RELATED APPLICATIONS

This application claims the benefit of and priority to U.S. Provisional Application Ser. No. 61/513,469, filed Jul. 29, 2011, which is incorporated herein by reference in its entirety

STATEMENT REGARDING GOVERNMENT LICENSE RIGHTS

The invention was made with government support under contract number HR0011-12-C-0010 awarded by U.S. Defense Advanced Research Projects Agency (DARPA). The government has certain rights in the invention.

TECHNICAL FIELD

The invention relates generally to synthetic biology and bioengineering. The invention relates more particularly to methods and systems for designing and producing engineered biological systems that can significantly advance genome, transcriptome and proteome quantification.

BACKGROUND

Engineering is defined as the application of scientific knowledge to meet human needs. In the twentieth century, scientific knowledge of electromagnetism and thermodynamics gave rise to the engineering disciplines of electrical engineering and information technology. Now in the twenty-first century, scientific knowledge of molecular biology promises to give rise to the new engineering discipline of synthetic biology.

Indeed, biology excels where other engineering substrates fall short. It is capable of atomic level precision in manufacturing, and stereo- and regiospecificity in chemical reactions. Biosynthetic pathways can catalyze difficult chemical reactions at mild temperatures and pressures, unlike chemical engineering. Microbes can derive energy from diverse sources and can switch between those sources depending upon availability, unlike electronic systems which derive energy only from electricity. Cells can make nanostructures with atomic level precision, unlike material science. Finally, unlike synthetic chemistry, biology is capable of an exquisite chemical specificity, sensing molecules at very low concentrations and catalyzing very dilute reactions.

These unique capabilities make engineered organisms this century's most important technology for meeting human needs. Foundational advances in the ability to engineer organisms can:
 Spur the transition of the petroleum-based energy and chemicals industry to a bio-based industry;
 Result in new treatments for human disease;
 Improve the stability and reduce the energy consumption of the food supply;
 Correct environmental problems that create a scarcity in raw materials, food and water.

Toward these goals, technologies that accelerate the speed with which engineered biological systems (e.g., viruses, single-cell organisms, plant cells and cell lines, mammalian cells and cell lines, etc.) can be designed, built and tested are needed to make full use of biological functionality. However, the ability to engineer organisms is currently limited. The complexity of the biological systems that scientists can engineer is constrained by the lack of necessary tools to design and test organisms. In particular, a central challenge is that when we construct engineered organisms and they fail to work as intended, it is difficult to determine why. This difficulty stems from the lack of measurement technologies that allow quick, precise and high-throughput identification and quantification of the DNA, RNA and protein species in the cell. While several different technologies are available for genome, transcriptome and proteome analysis, in practice these techniques usually require expensive equipment, specialized expert practitioners and are very time-consuming. These analysis technologies are not amenable to routine use while testing different designs of an engineered organism. Hence, current measurement technologies are inadequate to support the predictable engineering of biological systems.

Accordingly, measurement technologies are needed to routinely test and debug engineered organisms. Such technologies can provide the ability to quickly characterize and localize failures in engineered systems, allow the development of computer-aided design (CAD) tools for synthetic biology, and accelerate the design-build-test loop for the successful engineering of organisms.

SUMMARY

Methods and systems of the present invention relate to the design, production, and use of engineered cells for cell state quantification, such as genome, transcriptome and proteome quantification.

In one aspect, an engineered cell expressing a plurality of proteins of interest, and/or a plurality of cells comprising such engineered cell is provided. The cell can include a plurality of predefined, synthetic oligonucleotides introduced into the genome of the cell, where each of the plurality of oligonucleotides encodes a unique peptide tag for a predetermined protein of interest. Each unique peptide tag can have a different quantitatively measurable value. For example, the quantitatively measurable value can be measurable by mass spectrometry. In some embodiments, the unique peptide tags are separable from one another by chromatography, capillary electrophoresis or combinations thereof.

In various embodiments, the engineered cell is capable of expressing the proteins of interest, and each expressed protein of interest is fused to its unique peptide tag. In some embodiments, each of the unique peptide tags are capable of being released from their corresponding predetermined proteins of interest via proteolytic cleavage. For example, the unique peptide tags can be released from their corresponding proteins of interest upon cleavage by one or more proteolytic enzymes. In various embodiments, the plurality of oligonucleotides are each located in proximity of a gene of interest encoding a protein of interest, at the 5' or 3' of the gene of interest, or within the gene of interest.

In some embodiments, the unique peptide tags can comprise an affinity tag to facilitate affinity purification of the peptide tags.

In various embodiments, the engineered cell can further include one or more of the following:
 mutations of the genome where difficult to sequence DNA and RNA regions have been modified or deleted, and/or where repetitive elements have been removed;
 mutations of the genome to modify or eliminate difficult to measure proteins;
 mutations of the genome to remove background cleavage sites of a proteolytic enzyme;

mutations of the genome to remove spurious background affinity tag sites; and mutations of the genome where cryptic elements have been randomized and genetic elements have been decoupled.

In another aspect, a method for engineering a cell is provided. The method can include selecting a plurality of proteins of interest as subject for quantification and modifying the genome of the cell such that a plurality of predetermined peptide tags are engineered onto the plurality of proteins of interest. Each of the plurality of predetermined peptide tags is designed to be unique to each protein of interest and has a unique quantitatively measurable value. For example, the quantitatively measurable value can be measurable by mass spectrometry.

In some embodiments, the method can further include using one or more computer-aided design tools to optimize the modified cell. In various embodiments, the plurality of predetermined peptide tags are each located at the N- or C-terminus of its corresponding protein of interest, or within the corresponding protein of interest. In certain embodiments, the method can further include one or more of the following:

introducing mutations into the genome of the cell to modify or delete difficult to sequence DNA and RNA regions;

introducing mutations into the genome of the cell to modify or eliminate difficult to measure proteins;

introducing mutations into the genome of the cell to remove background cleavage sites of a proteolytic enzyme;

introducing mutations into the genome of the cell to remove spurious background affinity tag sites; and introducing mutations into the genome of the cell to randomize cryptic elements and to decouple genetic elements.

In some embodiments, the cell can be a prokaryotic or eukaryotic single cell organism, a plant cell or cell line, a mammalian cell or cell line, or an insect cell or cell line. For example, the cell can be *Mesoplasma florum, Escherichia coli, Saccharomyces cerevisiae* or a mammalian cell line.

The present invention also provides a method for measuring a proteome of an engineered cell as discussed herein. The method can comprise releasing the plurality of peptide tags engineered onto the plurality of proteins of interest. The method can further comprise subjecting the plurality of proteins of interest to quantification in a high throughput and automated fashion. In some embodiments, the proteins of interest can be quantified by mass spectrometry (MS).

In yet another aspect, a method for simultaneous genome, transcriptome and proteome quantification of the engineered cell is provided. The method can include providing DNA, RNA, and protein samples of the engineered cell and measuring an amount of the DNA, RNA and peptide tags thereof.

In still another aspect, a library of peptide tags capable of being quantitatively measured in a high throughput and automated fashion, such as mass spectrometry is provided. In some embodiments, each peptide tag can have a unique MS spectra relative to the other members of the library and to the background proteome. In some embodiments, the peptide tags are readily detectable via mass spectrometry. In some embodiments, the peptide tags can include one or more proteolytic cleavage sites, such that the peptide tags can be separated from their corresponding protein of interest. In various embodiments, the library of peptide tags can further have one or more of the following properties:

one or more peptide tag of the library of peptide tags can be less than 50 amino acids in length so as to be separable as a set from the background proteome by size fractionation;

one or more peptide tag of the library of peptide tags can be separable from each other and/or from the background proteome by chromatography and/or capillary electrophoresis;

one or more peptide tag of the library of peptide tags can have substantially the same ionization efficiency to facilitate quantification by mass spectrometry;

one or more peptide tag of the library of peptide tags can minimize ion suppression of other peptide tags to facilitate quantification by mass spectrometry;

one or more peptide tag of the library of peptide tags can contain an affinity tag so as to be capable of being enriched and/or purified from the background proteome and/or its corresponding predetermined protein of interest, for example, by affinity purification;

one or more peptide tag of the library of peptide tags can be isotopically labeled to enable either absolute quantification or simultaneous quantification of multiple samples.

In some embodiments, each of the peptide tags of the library are designed to have a detectable charge state with a unique mass to charge ratio, substantially the same ionization efficiencies, minimal ion suppression. In some embodiments, the peptide tags comprise amino acids selected from a predetermined set of amino acids. For example, the peptide tags can each have up to 40 amino acids selected from a predetermined set of amino acids. In some embodiments, the peptide tags have a proteolytic cleavage site. In some embodiments, each of the peptide tags have a fixed number of instances of each of a preselected set of one or more amino acids to facilitate isotopic labeling.

In another aspect, a method for designing the library of peptide tags is provided. The peptide tags can be designed to ionize efficiently so as to be detectable by mass spectrometry. In some embodiments, the peptide tags can be designed to have detectable charge state with unique mass to charge ratios so as to be uniquely resolvable from each other and the background proteome at the resolution of, for example, the mass spectrometer instrument used. In some embodiments, the peptide tags can be designed to have one or more proteolytic cleavage sites such that the peptide tags can be released from the protein of interest upon proteolysis.

In some embodiments, the proteolytic enzyme is a protease having a long recognition site such as, for example, Tobacco Etch Virus protease, Factor Xa protease, enterokinase, caspases, GranzymeB, GE's PreScission, trypsin, or any combination thereof. The proteolytic enzyme can be thermostable, or stable in denaturing solvent.

In some embodiments, the method can further include using one or more computer-aided design (CAD) tools to optimize design of the library of peptide tags. In various embodiments, the method can further comprise one or more of the following:

the peptide tags can be designed to be short in length (for example, less than 50 amino acids) so that the peptide tags can be separated from the background proteome by size fractionation;

the proteolytic cleavage site can be selected to minimize cleavage of the background proteome;

the peptide tags can be designed to elute at different times from a liquid chromatography column;

the peptide tags can be designed to migrate differently during capillary electrophoresis;

the peptide tags can be designed to have substantially the same ionization efficiency to facilitate quantification by mass spectrometry;

the peptide tags can be designed to minimize ion suppression to facilitate quantification by mass spectrometry;

the peptide tags can be designed to include an affinity tag to enable enrichment and/or purification from the background proteome;

the peptide tags can have an affinity tag which can be selected to minimize isolation of polypeptides from the background proteome;

the peptide tags can be designed to have a fixed number of instances of a set of a fixed number of instances of each of a preselected set of one or more amino acids to facilitate isotopic labeling.

In some aspects, the proteins of interest can be carefully selected to provide specific information about the engineered organism. The proteins of interest may belong to one or more metabolic pathways or one or more cell signaling pathways in the cell. The proteins of interest may all be related to a specific functionality of the cell, such as central metabolism, electron transport, amino acid biosynthesis, nutrient import, specific secondary metabolic pathways, or transcriptional regulation. In certain embodiments, the protein of interest are those proteins that are not readily detectable by untargeted or targeted mass spectrometry methods known in the art. The peptide tags are preferably non-deleterious for functionality of the proteins of interest. In some embodiments, the proteins of interest may account for more than 0.1%, 1%, 5%, 10%, 20%, 30%, 40%, 50%, 60%, 70%, 80%, 90%, or 95% of the proteome of the cell.

In some aspects, the invention provides a quantification system. The system can include a sample preparation unit designed to process a plurality of cells of the same engineered cell comprising the library of peptide tags discussed herein. The peptide tags can be engineered onto a plurality of proteins of interest in the cell and can be designed to be unique to each protein of interest. In some embodiments, the sample preparation unit processes the plurality of cells so as to release and separate the peptide tags from the plurality of proteins of interest. In some embodiments, the system can further include a mass spectrometer for measuring the released peptide tags. In certain embodiments, the system can include a plurality of isotopically labeled synthetic peptides corresponding to the peptide tags, for use as standards for mass spectrometry quantification.

In some aspects, a kit comprising the engineered cell as discussed herein and use instructions thereof is provided. In some embodiments, the kit can further include a plurality of isotopically labeled synthetic peptides corresponding to the unique peptide tags, for use as standards for mass spectrometry quantification.

In a further aspect, a kit comprising a library of oligonucleotides encoding the library of peptide tags as discussed herein and use instructions thereof is provided.

Some aspects of the invention relate to a computer program product for designing a peptide tag for an engineered cell. The program may reside on a hardware computer readable storage medium and may have a plurality of instructions which, when executed by a processor, cause the processor to select an amino acid sequence, for introducing into a cell to tag a protein of interest and without affecting a function of the protein of interest, wherein the amino acid sequence is detectable by mass spectrometry, wherein the amino acid sequence has a unique mass to charge ratio relative to proteolytic products of the background proteome endogenous to the cell, wherein the amino acid sequence includes a proteolytic cleavage site or protease recognition sequence such that the amino acid sequence can be released from the protein of interest upon proteolysis, and wherein the amino acid sequence is uniquely resolvable from other amino acid sequences at an absolute mass resolution of a mass spectrometer instrument used. In some embodiments, the selected amino acid sequence has 3-25, 5-15, 8-10 or up to 40 amino acids In some embodiments, the program further comprises selecting a protease having longer than 4, 5, or 6 amino acid recognition site to minimize overlap of the amino acid sequence with the background proteome. In some embodiments, the program further comprises selecting an affinity tag for inclusion in the amino acid sequence.

In some embodiments, the plurality of amino acid sequences can be designed so as to have substantially the same ionization efficiency and to be detectable by the mass spectrometer instrument used. In some embodiments, the plurality of amino acid sequences can be designed to minimize ion suppression between the sequences and are detectable by the mass spectrometer instrument used. In some embodiments, the plurality of amino acid sequences can be designed to elute at different times from a liquid chromatography column. In some embodiments, the plurality of amino acid sequences can be designed to migrate differently during capillary electrophoresis. In some embodiments, the plurality of amino acids sequences can be designed to comprise a fixed number of instances of each of a preselected set of one or more amino acids to facilitate isotopic labeling.

In some embodiments, the affinity tag can be AU1, AU5, T7-tag, V5-tag, B-tag, E2-tag, FLAG, EE-tag, HA, HAT, HSV-tag, KT3, Myc, NorpA, Arg-tag, Asp-tag, Cys-tag, His-tag, Phe-tag, S1-tag, S-tag, Strep-tag, Universal, VSV-G, or any combination thereof. In some embodiments, the amino acid sequence comprising the affinity tag can have 5 to 40, 7 to 30, or 10 to 25 amino acids.

Further aspects of the invention relate to a computer program product for designing genetic components for an engineered cell. In some embodiments, the program may reside on a hardware computer readable storage medium and may have a plurality of instructions which, when executed by a processor, cause the processor to perform one or more of the following operations:

avoiding a codon that is not translated in the cell;

avoiding a sequence that is cut by a native restriction system in the cell, or deleting the native restriction system therefrom;

recoding all stop codons as TAA;

eliminating key restriction sites so that the genetic components are compatible with a widely used DNA assembly standard, such as the BioBrick standard or DNA assembly method;

avoiding direct or inverted repeats, high GC content regions, high AT content regions or nucleotide homopolymers that can make the genetic components difficult to synthesize via commercial gene synthesis;

avoiding transposon insertion sites that would make the part vulnerable to mutation;

avoiding incidental regulatory motifs, RNase cleavage sites or RNA secondary structure elements that would cause unforeseen gene regulation effects;

designing operons to minimize spurious transcriptional and translational initiation;

eliminating cleavage sites of a proteolytic enzyme that would result in peptide fragments that overlap with a library of peptide tags; and eliminating spurious affinity tag sites that would result in contaminating proteins or peptides during affinity purification.

DETAILED DESCRIPTION

Figure 1:
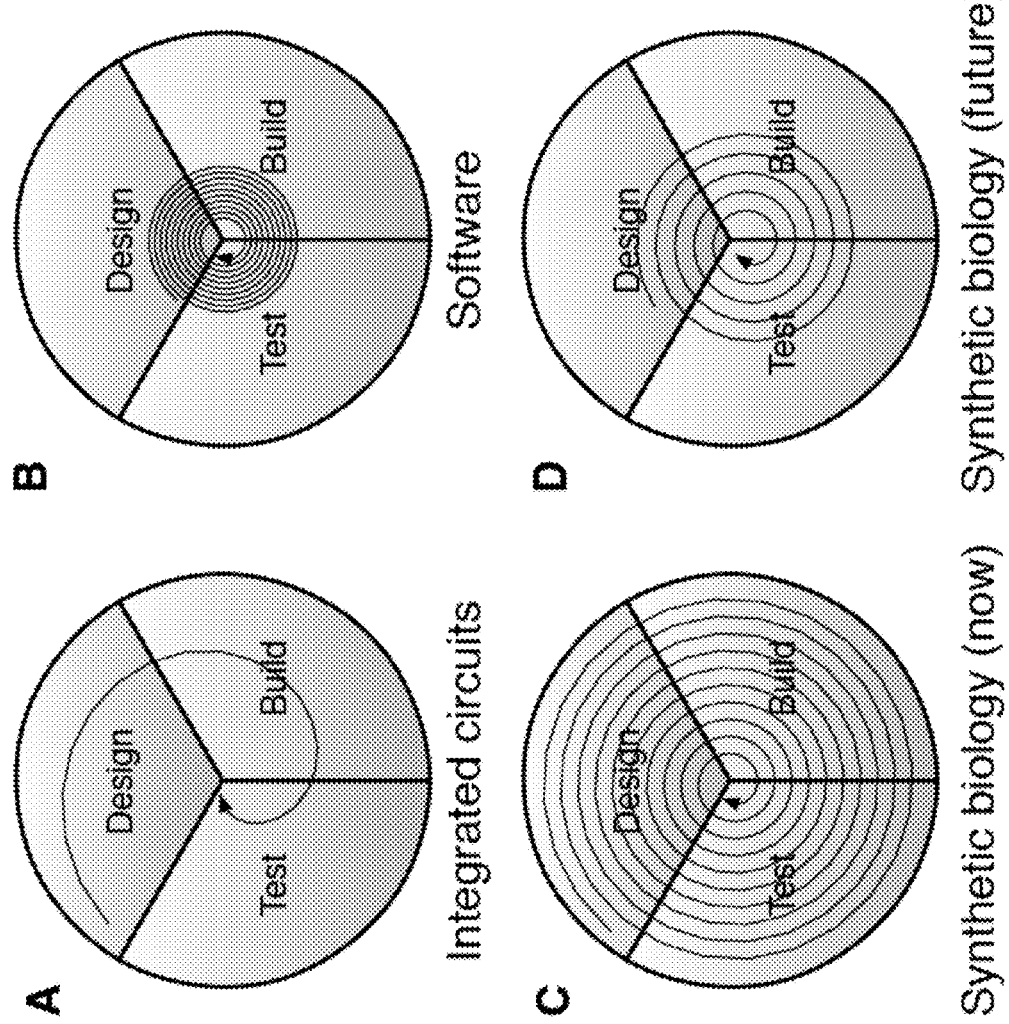
FIG. 1: (A) The design loop for integrated circuits effectively involves a single, long iteration. Investments have been made to ensure that CAD and simulation tools produce chip designs that behave predictably so a chip need only be fabricated once. (B) In contrast, in software development, compilation and testing is so fast that engineers loops around the design loop many times before arriving at a working system. (C) Currently in synthetic biology, designs yields systems with unpredictable behavior and measurement technology is inadequate to identify the points of failure in engineered organisms. Hence, the design loop consists of many lengthy iterations to get to a working system. (D) Methods and technologies for routine measurement of cell state would support the developed of CAD tools for reliable, forward design of biological systems reducing both the number and duration of loops needed to produce engineered organisms.

The present invention, in some aspects, radically redesigns the entire host organism to explicitly support routine measurement. Some aspects of the invention relate to the quantitative measurement of a plurality of DNA, RNA and protein species in the cell. When measuring cell state of natural organisms, different aspects of the cell can confound the analysis. For example, during genome sequencing, stretches of nucleotide homopolymers can be difficult to sequence. As a second example, during transcriptome analysis by RNA-seq, repetitive sequences can result in sequence reads that map to multiple parent transcripts making quantification difficult. Finally, during proteomics analysis by mass spectrometry (MS), peptides produced by protease digestion of the natural proteome can vary in ionization efficiency making detection and quantification difficult.

In conventional proteomics analysis, the total protein content of a cell culture is isolated and then digested with trypsin. Since trypsin has a very short cleavage site, digestion with trypsin typically yields tens of thousands of fragments. The resulting complex mixture of peptides is then separated by chromatography and each peptide subjected to analysis by mass spectrometry (MS). The more complex the initial mixture of peptides, the more sophisticated the separation and MS analysis is needed to successfully identify the parent proteins corresponding to each peptide in the mixture. More sophisticated chromatographic separation and MS analysis generally takes more time and thus limits the number of engineered organisms that can be analyzed per day. Furthermore, proteomics approaches generally only detect 20-40% of the proteins even in relatively small bacterial proteomes [Zhang, 2010]. With tandem affinity purification-mass spectrometry in which individual proteins were tagged, purified and analyzed by MS, Kuhner and colleagues were able to detect 60% of the annotated open reading frames and 85% of the predicted soluble proteome in Mollicutes [Kuhner, 2009].

In an effort to improve the coverage and quantitativeness of proteomics analysis, there is a growing interest in targeted proteomics [Picotti, 2009; Wienkoop, 2010; Kiyonami, 2010]. Targeted proteomics relies on the use of proteotypic peptides: peptides produced by proteolytic cleavage of the proteome that map uniquely to a parent protein and are readily detectable via MS [Kuster, 2005]. The MS can then be programmed to monitor only proteotypic peptides for the proteins of interest in a particular experiment. Such selective monitoring has four advantages: (1) redundant detection of proteins is avoided, a common problem in shotgun proteomics, (2) sensitivity is increased because fewer peptides need be measured in a single run, (3) the same targets can be measured across experimental samples for quantitative comparison [Deutsch, 2008], (4) by examining only the expected analytes, the speed of measurement is enhanced, and (5) isotopically labeled versions of expected peptides can be prepared and used for absolute quantitation. In selecting proteotypic peptides for use in targeted proteomics, there is an inherent tradeoff between finding one or more proteotypic peptides for each protein in the proteome and ensuring that each peptide has desirable properties for MS analysis (uniqueness to parent protein, hydrophobicity, mass, ionization efficiency, etc.). Moreover, these approaches generally require expensive instruments, specialized expertise, and significant effort both to identify suitable proteotypic peptides and then to conduct the subsequent analysis.

The approach of the present invention can eliminate these problems by distinguishing itself from previous work in at least one or more of the following ways:

Genes and gene products that are non-essential for laboratory growth under a pre-selected set of conditions can be eliminated. Due to the combinatorial nature of interactions between cellular components, reducing this gene set can dramatically simplify the analysis of strain performance by reducing the number of possible interactions. In some embodiments, preference can be given to deletion of those gene products that are difficult to measure and quantify using available measurement techniques. For example, the number of genes in M. florum can be reduced from 682 to less than 600.

Remaining essential genes and gene products can be redesigned to eliminate those regions that are difficult to measure and/or lead to unpredictable gene expression or regulation effects.

The proteome can be redesigned by introducing unique, genetically-encoded peptide tags onto each protein of interest that are specifically designed to be quantified by MS. The tags can be separable from the rest of the proteome by proteolytic cleavage and the resulting peptide tag mixture can be analyzable by MS. The peptide tags can be designed such that each tag has a unique MS spectra, can be readily detectable by MS, and does not interfere with parent protein function. Such an approach can dramatically reduce the complexity of the peptide mixture while enhancing detection of individual peptides by MS thereby making proteomics analysis significantly easier.

By developing a simplified, engineered strain that is optimized for cell state measurement together with the methods and systems for routine DNA, RNA and protein analysis, the testing phase of the design-build-test loop can be made significantly faster and more comprehensive. In particular, the present invention enables the rapid characterization and localization of failures in engineered organisms. The ability to routinely measure cell state is an absolute prerequisite to the future development of useful CAD tools for predictable, forward design of engineered cells.

DNA and RNA analysis technologies are reasonably mature and thus with some limited redesign of the genome of an organism of interest (for example, to eliminate repetitive regions, long homopolymers or other difficult to sequence regions), methods for routinely analyzing the genome and transcriptome can be developed using commercially available sequencers. Quantitative proteomics analysis, however, may require additional technology to become a routine process. Some aspects of the invention provide method and systems to facilitate the quantification of proteins by mass spectrometry (MS) by introducing deliberately designed peptide tags onto a plurality of proteins, preferably on the N- or C-terminus. In some embodiments, peptide tags are designed for each protein of the proteome. By designing these tags to have detectable charge state with unique mass to charge ratios, to not interfere with parent protein function, to be cleavable by protease digestion, and to be readily detectable by MS, quantitative proteome analysis by MS can be streamlined. In some embodiments, the tags can further be designed to optionally be enriched or purified from the background proteome by affinity chromatography and/or to optionally be separable from one another by liquid chromatography or capillary electrophoresis. It is also possible to dramatically simplify the host cell by deleting nonessential genes, especially gene whose gene products are difficult to measure. In addition, genes can be redesigned to make them easier to measure and model. Finally, the methods of the present invention are not limited to the punctual measurement of cell state (i.e. just once) but rather can enable fast, routine measurement so that measurement of cell state can be an integral step of the design-build-test loop.

In some embodiments, the present invention provides a simplified *M. florum* strain as a new model organism of great value to the synthetic biology community. *M. florum* has six-fold fewer gene products than the most intensively studied organism, *E. coli*. Recently there have been increased calls from the research community to develop a minimal organism as a next-generation chassis for synthetic biology [Vickers, 2010; Jewett, 2010]. The engineered organism can meet many of the researchers' requested criteria including having a simplified metabolism with fewer competing carbon sinks, fewer regulatory elements reducing unexpected feedback, and reduced toxicity issues. It is possible to have a suite of test strains in which particular subsets of the proteome can be tagged. For example, it is possible to tag all amino acid importers so that the user can observe the impact of the engineered system on nutrient demand by the cell. Furthermore, upon removal of non-essential genes, the re-engineered *M. florum* of the present invention may have the smallest genome of any known free-living organism, making it a powerful model for scientific study. One of skill in the art will appreciate that such engineered new organism can become a foundational resource for the synthetic biology community and provide a new piece of standard "wetware" that can make the design-build-test loop faster and more reliable.

DEFINITIONS

As used herein, the terms "nucleic acids," "nucleic acid molecule" and "polynucleotide" may be used interchangeably and include both single-stranded (ss) and double-stranded (ds) RNA, DNA and RNA:DNA hybrids. As used herein the terms "nucleic acid", "nucleic acid molecule", "polynucleotide", "oligonucleotide", "oligomer" and "oligo" are used interchangeably and are intended to include, but are not limited to, a polymeric form of nucleotides that may have various lengths, including either deoxyribonucleotides or ribonucleotides, or analogs thereof. For example, oligos may be from 5 to about 100 nucleotides, from 10 to about 80 nucleotides, or from 30 to about 50 nucleotides long. However, shorter or longer oligonucleotides may be used. Oligos for use in the present invention can be fully designed. A nucleic acid molecule may encode a full-length polypeptide or a fragment of any length thereof, or may be non-coding.

Nucleic acids can refer to naturally-occurring or synthetic polymeric forms of nucleotides. The oligos and nucleic acid molecules of the present invention may be formed from naturally-occurring nucleotides, for example forming deoxyribonucleic acid (DNA) or ribonucleic acid (RNA) molecules. Alternatively, the naturally-occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the invention include, for example, naturally-occurring nucleotides (for example, ribonucleotides or deoxyribonucleotides), or natural or synthetic modifications of nucleotides, or artificial bases. Modifications can also include phosphothio linked bases for increased stability.

Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the nucleotide comparison methods and algorithms set forth below, or as defined as being capable of hybridizing to the polynucleotides that encode the protein sequences.

As used herein, the term "gene" refers to a nucleic acid that contains information necessary for expression of a polypeptide, protein, or untranslated RNA (e.g., rRNA, tRNA, anti-sense RNA). When the gene encodes a protein, it includes the promoter and the structural gene open reading frame sequence (ORF), as well as other sequences involved in expression of the protein. When the gene encodes an untranslated RNA, it includes the promoter and the nucleic acid that encodes the untranslated RNA.

The term "gene of interest" (GOI) refers to any nucleotide sequence (e.g., RNA or DNA), the manipulation of which may be deemed desirable for any reason (e.g., confer improved qualities and/or quantities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding sequences which do not encode an mRNA or protein product (e.g., promoter sequence, polyadenylation sequence, termination sequence, enhancer sequence, etc.). For example, genes involved in the cis,cis-muconic acid biosynthesis pathway can be genes of interest. It should be noted that non-coding regions are generally untranslated but can be involved in the regulation of transcription and/or translation.

As used herein, the term "genome" refers to the whole hereditary information of an organism that is encoded in the DNA (or RNA for certain viral species) including both coding and non-coding sequences. In various embodiments, the term may include the chromosomal DNA of an organism and/or DNA that is contained in an organelle such as, for example, the mitochondria or chloroplasts and/or extrachromosomal plasmid and/or artificial chromosome. A "native gene" or "endogenous gene" refers to a gene that is native to the host cell with its own regulatory sequences whereas an "exogenous gene" or "heterologous gene" refers to any gene that is not a native gene, comprising regulatory and/or coding sequences that are not native to the host cell. In some embodiments, a heterologous gene may comprise mutated sequences or part of regulatory and/or coding sequences. In some embodiments, the regulatory sequences may be heterologous or homologous to a gene of interest. A heterologous regulatory sequence does not function in nature to regulate the same gene(s) it is regulating in the transformed host cell. "Coding sequence" refers to a DNA sequence coding for a specific amino acid sequence. As used herein, "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, ribosome binding sites, translation leader sequences, RNA processing site, effector (e.g., activator, repressor) binding site, stem-loop structure, and so on.

As described herein, a genetic element may be any coding or non-coding nucleic acid sequence. In some embodiments, a genetic element is a nucleic acid that codes for an amino acid, a peptide or a protein. Genetic elements may be operons, genes, gene fragments, promoters, exons, introns, regulatory sequences, or any combination thereof. Genetic elements can be as short as one or a few codons or may be longer including functional components (e.g. encoding proteins) and/or regulatory components. In some embodiments, a genetic element includes an entire open reading frame of a protein, or the entire open reading frame and one or more (or all) regulatory sequences associated therewith. One skilled in the art will appreciate that the genetic elements can be viewed as modular genetic elements or genetic modules. For example, a genetic module can comprise a regulator sequence or a promoter or a coding sequence or any combination thereof. In some embodiments, the genetic element includes at least two different genetic modules and at least two recombination sites. In eukaryotes, the genetic element can comprise at least three modules. For example, a genetic module can be a regulator sequence or a promoter, a coding sequence, and a polyadenlylation tail or any combination thereof. In addition to the promoter and the coding sequences, the nucleic acid sequence may comprises control modules including, but not limited to a leader, a signal sequence and a transcription terminator. The leader sequence is a non-translated region operably linked to the 5' terminus of the coding nucleic acid sequence. The signal peptide sequence codes for an amino acid sequence linked to the amino terminus of the polypeptide which directs the polypeptide into the cell's secretion pathway.

As generally understood, a codon is a series of three nucleotides (triplets) that encodes a specific amino acid residue in a polypeptide chain or for the termination of translation (stop codons). There are 64 different codons (61 codons encoding for amino acids plus 3 stop codons) but only 20 different translated amino acids. The overabundance in the number of codons allows many amino acids to be encoded by more than one codon. Different organisms (and organelles) often show particular preferences or biases for one of the several codons that encode the same amino acid. The relative frequency of codon usage thus varies depending on the organism and organelle. In some instances, when expressing a heterologous gene in a host organism, it is desirable to modify the gene sequence so as to adapt to the codons used and codon usage frequency in the host. In particular, for reliable expression of heterologous genes it may be preferred to use codons that correlate with the host's tRNA level, especially the tRNA's that remain charged during starvation. In addition, codons having rare cognate tRNA's may affect protein folding and translation rate, and thus, may also be used. Genes designed in accordance with codon usage bias and relative tRNA abundance of the host are often referred to as being "optimized" for codon usage, which has been shown to increase expression level. Optimal codons also help to achieve faster translation rates and high accuracy. In general, codon optimization involves silent mutations that do not result in a change to the amino acid sequence of a protein.

Genetic elements or genetic modules may derive from the genome of natural organisms or from synthetic polynucleotides or from a combination thereof. In some embodiments, the genetic elements modules derive from different organisms. Genetic elements or modules useful for the methods described herein may be obtained from a variety of sources such as, for example, DNA libraries, BAC (bacterial artificial chromosome) libraries, de novo chemical synthesis, or excision and modification of a genomic segment. The sequences obtained from such sources may then be modified using standard molecular biology and/or recombinant DNA technology to produce polynucleotide constructs having desired modifications for reintroduction into, or construction of, a large product nucleic acid, including a modified, partially synthetic or fully synthetic genome. Exemplary methods for modification of polynucleotide sequences obtained from a genome or library include, for example, site directed mutagenesis; PCR mutagenesis; inserting, deleting or swapping portions of a sequence using restriction enzymes optionally in combination with ligation; in vitro or in vivo homologous recombination; and site-specific recombination; or various combinations thereof. In other embodiments, the genetic sequences useful in accordance with the methods described herein may be synthetic oligonucleotides or polynucleotides. Synthetic oligonucleotides or polynucleotides may be produced using a variety of methods known in the art.

In some embodiments, genetic elements share less than 99%, less than 95%, less than 90%, less than 80%, less than 70% sequence identity with a native or natural nucleic acid sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments (*Meth. Mol. Biol.* 70: 173-187 (1997)). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer.

As used herein, the phrase "homologous recombination" refers to the process in which nucleic acid molecules with similar nucleotide sequences associate and exchange nucleotide strands. A nucleotide sequence of a first nucleic acid molecule that is effective for engaging in homologous recombination at a predefined position of a second nucleic acid molecule will therefore have a nucleotide sequence that facilitates the exchange of nucleotide strands between the first nucleic acid molecule and a defined position of the second nucleic acid molecule. Thus, the first nucleic acid will generally have a nucleotide sequence that is sufficiently complementary to a portion of the second nucleic acid molecule to promote nucleotide base pairing. Homologous recombination requires homologous sequences in the two recombining partner nucleic acids but does not require any specific sequences. Homologous recombination can be used to introduce a heterologous nucleic acid and/or mutations into the host genome. Such systems typically rely on sequence flanking the heterologous nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

It should be appreciated that the nucleic acid sequence of interest or the gene of interest may be derived from the genome of natural organisms. In some embodiments, genes of interest may be excised from the genome of a natural organism or from the host genome, for example M. florum. It has been shown that it is possible to excise large genomic fragments by in vitro enzymatic excision and in vivo excision and amplification. For example, the FLP/FRT site specific recombination system and the Cre/loxP site specific recombination systems have been efficiently used for excision large genomic fragments for the purpose of sequencing (see Yoon et al., Genetic Analysis: Biomolecular Engineering, 1998, 14: 89-95). In some embodiments, excision and amplification techniques can be used to facilitate artificial genome or chromosome assembly. Genomic fragments may be excised from M. florum chromosome and altered before being inserted into the host cell artificial genome or chromosome. In some embodiments, the excised genomic fragments can be assembled with engineered promoters and/or other gene expression elements and inserted into the genome of the host cell.

As used herein, the term "polypeptide" refers to a sequence of contiguous amino acids of any length. The terms "peptide," "oligopeptide," "protein" or "enzyme" may be used interchangeably herein with the term "polypeptide". In certain instances, "enzyme" refers to a protein having catalytic activities. As used herein, the terms "protein of interest," "POI," and "desired protein" refer to a polypeptide under study, or whose expression is desired by one practicing the methods disclosed herein. A protein of interest is encoded by its cognate gene of interest (GOI). The identity of a POI can be known or not known. A POI can be a polypeptide encoded by an open reading frame.

A "proteome" is the entire set of proteins expressed by a genome, cell, tissue or organism. More specifically, it is the set of expressed proteins in a given type of cells or an organism at a given time under defined conditions. Transcriptome is the set of all RNA molecules, including mRNA, rRNA, tRNA, and other non-coding RNA produced in one or a population of cells.

The term "fuse," "fused" or "link" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

As used herein, the term "tag" or "peptide tag" is intended to mean an amino acid sequence that, when detected and measured in a particular sample, indicates that the protein to which it was fused is present in the sample and provides a quantitative measurement thereof. For instance, a tag can be designed and selected such that its presence in a sample, as measured, for example, by mass spectrometry, necessarily measures the amount of the protein fused to the tag in the sample. A unique tag sequence is present for each protein of interest to which it is fused and in no other protein the tag may be present in the sample, cell type, or species under investigation. Moreover, different tags should preferably be distinguishable from one another and readily detectable by quantitative analysis such as mass spectrometry. For example, each tag can have a unique mass to charge ratio. In some embodiments, different tags can have different amino acid compositions and/or different isotopic labeling while having uniform ionization efficiency and minimizing ion suppression to facilitate mass spectrometry analysis. The tags can also be readily cleavable from the protein with a selected protease, to allow measurements. In some embodiments, the tags are inserted at the N- or C-terminus of the protein of interest to minimize interference with protein function. The tags can also be placed internally in-frame within the protein sequence, such as between successive protein domains, without affecting functionality. Preferred locations for the tag may be determined in part based on available empirical data (e.g., from affinity tag or other fusion protein experiments such as poly(H is), FLAG tag, MBP tag, etc.), three dimensional structures of the protein or similar proteins and/or in vivo or in vitro expression experiments. In some embodiments, the tags can also contain a short sequence motif, such as an affinity tag or chromatography tag to allow for partial or complete purification from a complex mixture, such as the background proteome. In some embodiments, the peptide tags can be designed to allow inclusion of a fixed number (e.g., one, two, three, or more) of a set of preselected (e.g., one, two, three, or more) amino acids. This design constraint offers two key advantages. First, synthesized, isotopically labeled versions of the tags can be made by incorporating only the specific, labeled amino acid(s) in the peptide synthesis, thereby simplifying and reducing the cost of peptide synthesis. Second, the specific amino acid(s) can be preselected such that the host organism is unable to (or has been engineered to be unable to) synthesize the specific amino acid(s) endogenously and instead must rely on import from the culture medium; thus, the organism can be grown in medium containing those specific, labeled amino acid(s), thereby guaranteeing that each peptide tag in the organism is isotopically labeled. Hence, every peptide tag having incorporated the specific, labeled amino acid(s) will be shifted by an equal, integer number of atomic mass units relative to a corresponding unlabeled tag.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RBS), which promotes efficient and accurate translation of mRNA. The prokaryotic RBS is the Shine-Dalgarno sequence, a purine-rich sequence of 5'-UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence A/GCCACCAUGG, which lies within a short 5' untranslated region, directs translation of mRNA. An mRNA lacking the Kozak consensus sequence may also be translated efficiently in an in vitro systems if it possesses a moderately long 5'-UTR that lacks stable secondary structure. While E. coli ribosome preferentially recognizes the Shine-Dalgarno sequence, eukaryotic ribosomes (such as those found in retic lysate) can efficiently use either the Shine-Dalgarno or the Kozak ribosomal binding sites.

As used herein, the terms "promoter," "promoter element," or "promoter sequence" refer to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

One should appreciate that promoters have modular architecture and that the modular architecture may be altered. Bacterial promoters typically include a core promoter element and additional promoter elements. The core promoter refers to the minimal portion of the promoter required to initiate transcription. A core promoter includes a Transcription Start Site, a binding site for RNA polymerases and general transcription factor binding sites. The "transcription start site" refers to the first nucleotide to be transcribed and is designated +1. Nucleotides downstream of the start site are numbered +1, +2, etc., and nucleotides upstream of the start site are numbered −1, −2, etc. Additional promoter elements are located 5' (i.e., typically 30-250 bp upstream of the start site) of the core promoter and regulate the frequency of the transcription. The proximal promoter elements and the distal promoter elements constitute specific transcription factor site. In prokaryotes, a core promoter usually includes two consensus sequences, a −10 sequence or a −35 sequence, which are recognized by sigma factors (see, for example, Hawley; D. K. et al., *Nucl. Acids Res.* 11, 2237-2255 (1983)). The −10 sequence (10 bp upstream from the first transcribed nucleotide) is typically about 6 nucleotides in length and is typically made up of the nucleotides adenosine and thymidine (also known as the Pribnow box). In some embodiments, the nucleotide sequence of the −10 sequence is 5'-TATAAT or may comprise 3 to 6 bases pairs of the consensus sequence. The presence of this box is essential to the start of the transcription. The −35 sequence of a core promoter is typically about 6 nucleotides in length. The nucleotide sequence of the −35 sequence is typically made up of the each of the four nucleosides. The presence of this sequence allows a very high transcription rate. In some embodiments, the nucleotide sequence of the −35 sequence is 5'-TTGACA or may comprise 3 to 6 bases pairs of the consensus sequence. In some embodiments, the −10 and the −35 sequences are spaced by about 17 nucleotides. Eukaryotic promoters are more diverse than prokaryotic promoters and may be located several kilobases upstream of the transcription starting site. Some eukaryotic promoters contain a TATA box (e.g. containing the consensus sequence TATAAA or part thereof), which is located typically within 40 to 120 bases of the transcriptional start site. One or more upstream activation sequences (UAS), which are recognized by specific binding proteins can act as activators of the transcription. Theses UAS sequences are typically found upstream of the transcription initiation site. The distance between the UAS sequences and the TATA box is highly variable and may be up to 1 kb.

As used herein, the term "vector" refers to any genetic element, such as a plasmid, phage, transposon, cosmid, chromosome, virus, virion, etc., capable of replication when associated with the proper control elements and which can transfer gene sequences into or between cells. The vector may contain a marker suitable for use in the identification of transformed or transfected cells. For example, markers may provide antibiotic resistant, fluorescent, enzymatic, as well as other traits. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The term "expression vector" refers to a vector which is capable of expressing of a gene that has been cloned into it. Such expression can occur after transformation into a host cell, or in IVPS systems. The cloned DNA is usually operably linked to one or more regulatory sequences, such as promoters, activator/repressor binding sites, terminators, enhancers and the like. The promoter sequences can be constitutive, inducible and/or repressible.

As used herein, the term "host" refers to any prokaryotic or eukaryotic (e.g., mammalian, insect, yeast, plant, avian, animal, etc.) cell or organism. The host cell can be a recipient of a replicable expression vector, cloning vector or any heterologous nucleic acid molecule. Host cells may be prokaryotic cells such as *M. florum* and *E. coli*, or eukaryotic cells such as yeast, insect, amphibian, or mammalian cells or cell lines. Cell lines refer to specific cells that can grow indefinitely given the appropriate medium and conditions. Cell lines can be mammalian cell lines, insect cell lines or plant cell lines. Exemplary cell lines can include tumor cell lines and stem cell lines. The heterologous nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Sambrook, et al., Molecular Cloning: A Laboratory Manual, Cold Spring Harbor Laboratory, Cold Spring Harbor, N.Y.

One or more nucleic acid sequences can be targeted for delivery to target prokaryotic or eukaryotic cells via conventional transformation or transfection techniques. As used herein, the terms "transformation" and "transfection" are intended to refer to a variety of art-recognized techniques for introducing an exogenous nucleic acid sequence (e.g., DNA) into a target cell, including calcium phosphate or calcium chloride co-precipitation, DEAE-dextran-mediated transfection, lipofection, electroporation, sonoporation, optoporation, injection and the like. Suitable transformation or transfection media include, but are not limited to, water, $CaCl_2$, cationic polymers, lipids, and the like. Suitable materials and methods for transforming or transfecting target cells can be found in Sambrook, et al., *Molecular Cloning: A Laboratory Manual.* 2nd, ed., Cold Spring Harbor Laboratory, Cold Spring Harbor Laboratory Press, Cold Spring Harbor, N.Y., 1989, and other laboratory manuals. In certain instances, oligo concentrations of about 0.1 to about 0.5 micromolar (per oligo) can be used for transformation or transfection.

As used herein, the term "marker" or "reporter" refers to a gene or protein that can be attached to a regulatory sequence of another gene or protein of interest, so that upon expression in a host cell or organism, the reporter can confer certain characteristics that can be relatively easily selected, identified and/or measured. Reporter genes are often used as an indication of whether a certain gene has been introduced into or expressed in the host cell or organism. Examples of commonly used reporters include: antibiotic resistance genes, auxotropic markers, β-galactosidase (encoded by the bacterial gene lacZ), luciferase (from lightening bugs), chloramphenyl acetyltransferase (CAT; from bacteria), GUS (β-glucuronidase; commonly used in plants) and green fluorescent protein (GFP; from jelly fish). Reporters or markers can be selectable or screenable. A selectable marker (e.g., antibiotic resistance gene, auxotropic marker) is a gene confers a trait suitable for artificial selection; typically host cells expressing the selectable marker is protected from a selective agent that is toxic or inhibitory to cell growth. A screenable marker (e.g., GFP, lacZ) generally allows researchers to distinguish between wanted cells (expressing the marker) and unwanted cells (not expressing the marker or expressing at insufficient level).

Other terms used in the fields of recombinant nucleic acid technology, microbiology, and molecular and cell biology as used herein will be generally understood by one of ordinary skill in the applicable arts.

Organisms or Host Cells for Engineering

The host cell or organism, as disclosed herein, may be chosen from eukaryotic or prokaryotic systems, such as bacterial cells (Gram negative or Gram positive), yeast cells (for example, *Saccharomyces cereviseae* or *Pichia pastoris*), animal cells and cell lines (such as Chinese hamster ovary (CHO) cells), plant cells and cell lines (such as *Arabidopsis* T87 cells and Tabacco BY-2 cells), and/or insect cells and cell lines. Suitable cells and cell lines can also include those commonly used in laboratories and/or industrial applications. In some embodiments, host cells/organisms can be selected from, but are not limited to, *Escherichia coli, Gluconobacter oxydans, Gluconobacter Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Mycoplasma florum, Mycoplasma genitalium, Mycoplasma capricolum, Mycoplasma mycoides, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceusi, Streptomyces tanashiensis, Streptomyces virginiaei, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella enterica, Salmonella typhimurium, Salmonella schottmulleri, Xanthomonas citri, Saccharomyces* spp. (e.g., *Saccharomyces cerevisiae, Saccharomyces bayanus, Saccharomyces boulardii, Schizosaccharomyces pombe), Arabidopsis thaliana, Nicotiana tabacum*, CHO cells, 3T3 cells, COS-7 cells, DuCaP cells, HeLa cells, LNCap cells, THP1 cells, 293-T cells, Baby Hamster Kidney (BHK) cells, HKB cells, hybridoma cells, as well as bacteriophage, baculovirus, adenovirus, or any modifications and/or derivatives thereof. In certain embodiments, the genetically modified host cell is a *Mesoplasma florum, E. coli*, yeast, mammalian cells and cell lines, green plant cells and cell lines, or algae. Non-limiting examples of algae that can be used in this aspect of the invention include: *Botryococcus braunii; Neochloris oleoabundans; Scenedesmus dimorphus; Euglena gracilis; Nannochloropsis salina; Dunaliella tertiolecta; Tetraselmis chui; Isochrysis galbana; Phaeodactylum tricornutum; Pleurochrysis carterae; Prymnesium parvum; Tetraselmis suecica*; or *Spirulina* species. In various aspects of the invention, the cells are genetically engineered or metabolically evolved, for example, for purpose of cell state quantification. The terms "metabolically evolved" or "metabolic evolution" related to growth-based selection (metabolic evolution) of host cells that demonstrate improved growth (cell yield).

It should be noted that various engineered strains and/or mutations of the organisms or cell lines discussed herein can also be used. For example, an exogenous gene, pathway or multi-gene circuit of interest can be added to the cell to obtain a desired behavior, function or phenotype, such as production of a chemical of interest. As a second example, endogenous genes may be modified or deleted to obtain a desired behavior, function or phenotype, such as production of a chemical of interest.

In an exemplary embodiment, *Mesoplasma florum* can be used as a host organism for synthetic biology because it is one of the simplest known organisms that is easy and safe to manipulate. When faced with a challenging design problem, starting from building the simplest possible system that has the necessary functionality is a logic decision. Then, as the needs of the end user grow, additional complexity can be added. *M. florum* has a genome of 793,244 base pairs or ~800 kb (Genbank NC 006055). The *M. florum* genome encodes just 682 annotated genes compared to 4,377 genes in the model organism *E. coli*. The six-fold difference in genome size and complexity between the two organisms makes a significant difference in the ability to wholesale reengineer the organism. For example, to synthesize redesigned versions of all *M. florum* genes would cost less than $240,000 at current commercial gene synthesis rates versus $1.4 million for *E. coli*. Given its small number of genes, it is unsurprising that *M. florum* lacks many of the secondary metabolism pathways, such as amino acid biosynthesis, that exist in other prokaryotes. Its metabolism is similar to that of *Mycoplasma pneumoniae* [Yus, 2009], another *Mycoplasma* with reduced metabolic complexity. Instead, it imports most nutrients necessary for growth from the media. It is estimated that *M. florum* has four times fewer metabolites than *E. coli*, making it a significantly easier target for metabolomics analysis using current methods [Bennett, 2008; Yuan, 2008].

Researchers at the J. Craig Venter Institute initially focused their efforts to construct a chemically synthesized genome on the 580 kb *Mycoplasma genitalium* and later on the 1.08 Mb *Mycoplasma mycoides* genome [Gibson, 2008; Gibson, 2010]. Like *Mesoplasma florum*, Mycoplasmas are also members of the class Mollicutes, a class of bacteria known for their characteristically small number of genes. Similarly, Luis Serrano and colleagues at the Centre for Genomic Regulation in Spain performed a detailed analysis of the transcriptome, proteome and metabolome of another Mollicute, the 816 kb *Mycoplasma pneumoniae* [Guell, 2009; Kuhner, 2009; Yus, 2009]. However, *M. genitalium, M mycoides*, and *M. pneumoniae* are all very poor candidates for a host organism or chassis for synthetic biology research, since all three species are human or livestock pathogens that grow very slowly and are harder to manipulate compared to the non-pathogenic *M. florum.*

Despite being significantly simpler than most other prokaryotes, *M. florum* still retains the necessary characteristics desirable for reengineering: safety (no potential for pathogenicity), fast growth, and genetic tractability. *M. florum* has no known pathogenic potential to people, animals or plants. In fact, as an insect commensal it doesn't even grow at human body temperatures. *M. florum* grows quickly, with a doubling time of 40 minutes, meaning that dense liquid cultures or visible colonies on solid agar media are obtained in 24 hours. There are basic genetic tools for *M. florum* including a transposon insertion system, based on the Tn5 transposome [Reznikoff, 2004].

In addition, the small number of gene products (682 in the wildtype strain) in *M. florum* renders it a far more tractable target for routine "Omics" (e.g., genomics, proteomics, etc.) measurement than other organisms. Given *M. florum's* small genome size, it is possible to sequence genomes from tens of engineered strains in parallel in a single lane of an Illumina Genome Analyzer II. Although the first chemical synthesis and transplantation of the *M. mycoides* genome into *Mycoplasma capricolumn* cost the J. Craig Venter Institute a reported $40 million and took 10-15 years, the cost and time for comparable efforts will fall dramatically over the next decade. Furthermore, using next-generation sequencing technology, transcriptomes can be measured from multiple engineered strains and conditions in a single run using RNA-Seq [Nagalakshmi, 2008; Gibbons, 2009; Oliver, 2009]. RNA-Seq uses sequencing reads to identify and count individual mRNA molecules that have been reverse transcribed into cDNA. The small number of RNA species in *M. florum* means that the short sequence reads can be unambiguously mapped to unique genome locations during analysis.

However, parallel, quantitative analysis of all proteins in the cell remains a significant challenge, despite the small size of the *M. florum* proteome. Making quantitative proteomics analysis routine via proteome redesign is one of the key advantages of the present invention. Furthermore, based on work of the present invention performed on *M. florum*, it is possible to make the measurement of the DNA, RNA and/or protein species in a simplified cell a routine process. Towards this end, *M. florum* or other genomes can be redesigned to facilitate making these measurements.

Mass Spectrometry

Generally speaking, mass spectrometry (MS) is an analytical technique that measures the mass-to-charge ratio of charged particles. It is used for determining masses of particles, determining the elemental composition of a sample or molecule, and elucidating the chemical structures of molecules, such as peptides and other chemical compounds. The MS principle is generally known to be ionizing chemical compounds to generate charged molecules or molecule fragments and measuring their mass-to-charge ratios. In a typical MS procedure:

1) A sample is loaded onto the MS instrument, and undergoes vaporization;
2) The components of the sample are ionized by one of a variety of methods (e.g., by impacting them with an electron beam), which results in the formation of charged particles (ions);
3) The ions are separated according to their mass-to-charge ratio in an analyzer by electromagnetic fields;
4) The ions are detected, usually by a quantitative method; and
5) The ion signal is processed into mass spectra.

MS instruments generally include three modules:

An ion source, which can convert gas phase sample molecules into ions (or, in the case of electrospray ionization, move ions that exist in solution into the gas phase);

A mass analyzer, which sorts the ions by their masses by applying electromagnetic fields;

A detector, which measures the value of an indicator quantity and thus provides data for calculating the abundances of each ion present The MS technique has both qualitative and quantitative uses. These include identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum). MS can be used in analytical studies for physical, chemical, or biological properties of a great variety of compounds.

A tandem mass spectrometer is one capable of multiple rounds of mass spectrometry, usually separated by some form of molecule fragmentation. For example, one mass analyzer can isolate one peptide from many entering a mass spectrometer. A second mass analyzer then stabilizes the peptide ions while they collide with a gas, causing them to fragment by collision-induced dissociation (CID). A third mass analyzer then sorts the fragments produced from the peptides. Tandem MS can also be done in a single mass analyzer over time, as in a quadrupole ion trap. There are various methods for fragmenting molecules for tandem MS, including collision-induced dissociation (CID), electron capture dissociation (ECD), electron transfer dissociation (ETD), infrared multiphoton dissociation (IRMPD), blackbody infrared radiative dissociation (BIRD), electron-detachment dissociation (EDD) and surface-induced dissociation (SID). An important application using tandem mass spectrometry is in protein identification.

Selected reaction monitoring (SRM) and multiple reaction monitoring (MRM) provide highly selective methods of tandem mass spectrometry which have the potential to effectively filter out all molecules and contaminants except the desired analyte. This is particularly beneficial if complex samples are analyzed which tend to have several isobaric species present within a defined analytical window. Usually, a combination of precursor (parent ion) selection in the first stage of the mass spectrometer (here termed Q1: quadrupole 1, but also equivalent for the respective stages in non-quadrupole mass spectrometers such as ion traps etc.), fragmentation of the parent ion into many fragments of which one or several specific fragments are selected in the following steps of the MS-measurement (usually in quadrupole 3, Q3) and detected at the ion detector. This two-step selection ensures that the desired analyte is measured and any other ion species are reduced in their intensity. Signal-to-noise ratio is much superior to conventional MS/MS experiments which select one mass window in Q1, and then measure all generated fragments in the ion detector. In principle, this MS-based approach can provide absolute structural specificity for the analyte, and in combination with appropriate stable isotope-labeled internal standards (SISs), it can provide absolute quantitation of analyte concentration.

In conventional SRM/MRM type experiments, a stable isotope labeled reference is used to generate an analyte/reference pair which will be used for quantification of analyte against the reference. For the analysis of proteins, such a reference peptide differs from the analyte to be measured only by incorporation of isotopes, to make it distinctly different in mass for the Q1 selection, but otherwise identical in chemical composition, and physico-chemical behavior. In a typical experiment, the analyte/reference pair is selected, i.e., in Q1 by switching mass selection channels between these two masses. The subsequent fragmentation of these two ions leads to distinct (specific) fragment masses. One or more suitable fragment masses are then chosen where the Q3 filter remains on the position of the selected fragment ions, thus assuring transition of this ion to the mass analyzer, and filtering out other ion species.

In one embodiment, a quadrupole time-of-flight (QTOF) mass spectrometer can be used. QTOF mass spectrometers combine the high performance of time-of-flight analysis in both the mass spectrometry (MS) and tandem MS (MS/MS) modes, with the well accepted and widely used techniques of electrospray ionization (ESI) and atmospheric pressure chemical ionization (APCI). In general, QTOF is similar to a triple quadrupole with the last quadrupole section replaced by a time-of-flight (TOF) analyzer. In the usual QTOF configuration, an additional r.f. quadrupole Q0 is added to provide collisional damping, so the instrument consists of three quadrupoles, Q0, Q1 and Q2, followed by a reflecting TOF mass analyzer with orthogonal injection of ions. Ions are sampled from a high-pressure electrospray or APCI ion source through an r.f. ion guide Q0 into Q1. The additional quadrupole Q0 is used for collisional cooling and focusing of the ions entering the instrument. Both Q0 and Q2 are operated in the r.f.-only mode: the r.f. field creates a potential well that provides radial confinement of the precursor and/or fragment ions. Since the r.f. quadrupoles are normally operated at a pressure of several millitorr, they provide both radial and axial collisional damping of ion motion. The ions are thermalized in collisions with neutral gas molecules, reducing both the energy spread and the beam diameter and resulting in better transmission into and through both the quadrupole and TOF analyzers. After leaving the r.f. quadrupoles, ions are re-accelerated in the axial direction to the necessary energies with near-thermal energy spreads. One of the main advantages of QTOF instruments over triple quadrupoles is the high mass resolution of TOF, typically around 10 000 (m/$\Delta$m, where $\Delta$m is the full peak width at half-maximum (FWHM)). As a result, interfering peaks of ions having the same nominal mass can be resolved partially or completely, the charge state of multiply charged ions can in many cases be determined from their isotopic spacing, and signal-to-noise ratio is improved owing to grouping of ions into narrower peaks (increasing the peak height).

An enhancement to the mass resolving and mass determining capabilities of mass spectrometry is using it in tandem with chromatographic separation techniques. A common combination is liquid chromatography mass spectrometry (LC/MS or LC-MS). In this technique, a liquid chromatograph is used to separate different molecules before they are introduced to the ion source and mass spectrometer. The mobile phase is liquid, usually a mixture of water and organic solvents. Most commonly, an electrospray ionization source is used in LC/MS. There are also some newly developed ionization techniques like laser spray. In an embodiment, Agilent's RapidFire automated, solid phase purification, high-throughput system, can be used. RapidFire sample throughput is 10× faster than conventional MS screening methods.

Similar to liquid chromatography MS (LC/MS), gas chromatography mass spectrometry (GC/MS or GC-MS) separates compounds chromatographically before they are introduced to the MS. In this technique, a gas chromatograph is used to separate different compounds. This stream of separated compounds is fed online into the ion source, a metallic filament to which voltage is applied. This filament emits electrons which ionize the compounds. The ions can then further fragment, yielding predictable patterns. Intact ions and fragments pass into the mass spectrometer's analyzer and are eventually detected. GC/MS is particularly useful in the separation and analysis of volatile metabolites.

Ion mobility spectrometry/mass spectrometry (IMS/MS or IMMS) is a technique where ions are first separated by drift time through some neutral gas under an applied electrical potential gradient before being introduced into a mass spectrometer. Drift time is a measure of the radius relative to the charge of the ion. The duty cycle of IMS (the time over which the experiment takes place) is longer than most mass spectrometric techniques, such that the mass spectrometer can sample along the course of the IMS separation. This produces data about the IMS separation and the mass-to-charge ratio of the ions in a manner similar to LC/MS.

The duty cycle of IMS is short relative to liquid chromatography or gas chromatography separations and can thus be coupled to such techniques, producing triple modalities such as LC/IMS/MS.

Capillary electrophoresis (CE) can also be used to separate molecular species prior to mass spectroscopy. Both positive and negative CE can be effective in separating molecules by charge prior to MS analysis. CE/MS and CE/MS/MS are especially useful in separation and analysis of metabolites.

Mass spectrometry can be used for the characterization and sequencing of proteins or peptides. The two primary methods for ionization of whole proteins are electrospray ionization (ESI) and matrix-assisted laser desorption/ionization (MALDI). In keeping with the performance and mass range of available mass spectrometers, two approaches are used for characterizing proteins. In the first, intact proteins are ionized by either of the two techniques described above, and then introduced to a mass analyzer. This approach is referred to as "top-down" strategy of protein analysis. In the second, proteins are enzymatically digested into smaller peptides using proteases such as trypsin or pepsin, either in solution or in gel after electrophoretic separation. Other proteolytic agents can also be used. The collection of peptide products are then introduced to the mass analyzer. When the characteristic pattern of peptides is used for the identification of the protein the method is called peptide mass fingerprinting (PMF), if the identification is performed using the sequence data determined in tandem MS analysis it is called de novo sequencing. These procedures of protein analysis are also referred to as the "bottom-up" approach.

For mass spectrometry base protein quantification of a given proteome, the proteome can be digested using a protease and subsequently the resulting peptides are analyzed and quantified using a mass spectrometer. There are two major approaches to protein quantification. First is relative quantification of a protein from one sample to another. In this approach the peptides can be either isotopically labeled during cell growth or post protease digest labeled to differentiate the samples for the quantification purpose. Second is absolute quantification of a protein or proteins in a sample—in this approach proteolytic peptides of a protein are first identified and characterized. From the characterized peptides a few sequences are selected and chemically synthesized using isotopically labeled amino acids, to differentiate these peptides from their native forms, and are spiked into the proteolytic digest to be used as internal standards for the peptide quantification. In various embodiments, either relative or absolute quantification can be applied, for example, to measure cell state such as the proteome. In certain embodiments, a pre-selected and pre-labeled series of internal standards can be provided, as part of the kit/package to be supplied with the mass spectrometer and engineered cell. These standards can be selected based on the peptide tags present in the engineered cell.

Engineered Biological Systems or Cells

The present invention, in some aspects, provides methods and systems for redesigning a host cell to explicitly support routine, quantitative analysis, so as to quickly characterize and localize failures in engineered systems, and to facilitate efforts to develop CAD tools for synthetic biology. As an initial example and for reasons explained above, one of the simplest known free-living organisms, *Mesoplasma florum* was chosen. Yus and colleagues have established a metabolic reconstruction for a related organism, *Mycoplasma pneumonia*. Based on our annotated genome of *Mycoplasma florum*, we expect it to have a similar metabolism.

In some embodiments, *M. florum* genes whose products are difficult to measure can be deleted. In all, a simplified cell containing a sufficiently small number of genes (e.g., a few hundred or less than 600 genes) may be provided, which would constitute a simple free-living organism—an ideal chassis for synthetic biology. In addition, the *M. florum* proteome can be redesigned to be readily quantifiable by mass spectrometry (MS) by introducing genetically-encoded peptide tags onto each protein that can be quantified simultaneously by MS. Using the measurement technologies described herein, it is possible to quickly test and debug the engineered strains and use the resulting data to inform the next iteration of design. The testing tools described here can then pave the way for subsequent work to develop CAD tools for the predictive, forward design of biological systems.

Some embodiments relate to methods and systems to measure cell state, for example, nucleic acids (e.g. DNA, RNA) and/or protein species in a cell. The ability to routinely, quantitatively measure cell state can allow for the development of predictive, forward design tools for synthetic biology. In some embodiments, the entire genome of a host strain of choice can be redesigned, such as for example, the simple organism *M. florum*, to explicitly support routine cell state measurements.

Designed Peptide Tags

In certain aspects, the present invention provides for an engineered host cell or organism in which intentionally designed, unique peptide sequences (peptide tags) are introduced onto every protein of interest in the proteome. The tags are preferably positioned on either the N- or C-terminus of the protein of interest but may also be located within the protein of interest. The tags can be released by proteolytic cleavage and optionally be purified from the background proteome by size selective methods, chromatographic separation and/or by affinity chromatography. Since the tags are being designed rather than relying on naturally occurring peptides, it is possible to design them to occur within a relatively narrow mass range while still being resolvable by MS in a single run. Similarly, the tags are designed to have unique MS spectra, comparable ionization efficiencies and to minimize ion suppression effects so that the tags can be quantitatively compared within a single experimental sample. By designing the peptide tags, the entire organism, and even the MS instrument, proteomics can be dramatically simplified. In designing the peptide tag set, lessons from the selection of proteotypic peptides from natural proteomes can be leveraged [Mallick, 2007; Fusaro, 2009; Webb-Robertson, 2010].

In certain aspects, the present invention provides for a set or sets of unique peptide tags, to be genetically fused with each protein of interest in the proteome, that can serve as an unambiguous identifier for the associated protein. In some embodiments, the unique peptide tags can serve as unambiguous identifier using, for example, a MS measurement. A specific protease cleavage site can be associated with unique peptide tag sequences so that the peptide tags can be liberated from the intact proteins by proteolysis prior to MS analysis. In some embodiments, the design of the peptide tag set is dictated by a number or combination of the following interdependent factors. In some embodiments, the tags can be designed so as to be readily detectable via a quantification method, such as MS. In some embodiments, the tags can be designed so as to be readily cleavable from the parent proteins with a selected protease. Proteases with varying cleavage specificity, efficiency and robustness can be used. In some embodiments, the tags can be designed to have unique masses and/or mass to charge ratio relative to the peptide fragments produced from proteolysis of the background proteome. In a preferred embodiment, proteases with long recognition sites can be used to ensure minimal overlap of peptides from the background proteome. In some embodiments, the tags are designed not be deleterious to or interfere significantly with the parent proteins' function. One of skill in the art will understand that it is also possible to delete from the genome nonessential proteins that cannot be tagged. In some embodiments, the tags are designed to be uniquely resolvable from other tags at the absolute mass resolution of the mass spectrometer instrument used. If needed, an additional separation step, such as liquid chromatography, prior to MS analysis can be used to decrease coincident mass overlap. In some embodiments, the tags are designed to have similar lengths (e.g., 3-50, 5-25, 8-15 or up to 40 amino acids without the protease cleavage site). Thus, the peptide tags can be separated from the background proteome via any suitable size selection method, such as, for example filtration. In some embodiments, the tags are designed to have uniform ionization efficiency. In some embodiments, the tags are designed to minimize ion suppression between tags.

In some embodiments, the tags are designed from a restricted set of amino acids to avoid those amino acids with undesirable properties. Amino acids with complex side chains or side chains modified either by the cell or during sample preparation can be omitted. Examples include methionine and cysteine, prone to oxidation; asparagine and glutamine, subject to deamination; histidine and tryptophan with complex and charged side chains; lysine, subject to acetylation; and serine, threonine, and tyrosine, subject to phosphorylation. Proline can contributed to difficulties in identifying peptides by fragmentation. Isoleucine and leucine have identical molecular weights, so one or the other should not be used in tags. The remaining set of amino acids: glycine, alanine, valine, leucine, aspartic acid, glutamic acid, phenylalanine, and arginine are typically suitable for use in design of peptide tags. Under some circumstances, it may be desirable to include one or more of the hydroxy-amino acids, tyrosine, serine or threonine, to manage the charge properties of peptides, despite the possibility of modification.

In some embodiments, the tags are designed to further include, if necessary, an affinity tag to facilitate affinity purification and/or enrichment of the tags from the background proteome. In some embodiments, if necessary, the tags can be separable from the background proteome via any suitable technique known in the art, for example a liquid chromatography or filtration step. In some embodiments, it is preferred to avoid a time-consuming, slow gradient liquid chromatography (LC) step if possible, but if an LC step is necessary, then the peptides can be designed to elute at different times from the LC column.

If desired, peptide tags can be designed to include a fixed number (e.g., one, two, three, or more) of a set of specific (e.g., one, two, three, or more) amino acids. This design constraint guarantees that synthesized, isotopically labeled versions of the tags can be made by incorporating only the specific, labeled amino acid(s) in the peptide synthesis. Such a design can reduce the cost of synthesizing pure peptide standards. In addition, the specific amino acid(s) can be preselected such that the engineered organism is unable to synthesize the specific amino acid(s) endogenously and instead must rely on import from the culture medium; thus, the organism can be grown in medium containing those specific, labeled amino acid(s), thereby guaranteeing that each peptide tag is isotopically labeled. Hence, every peptide tag having incorporated the specific, labeled amino acid(s) will be shifted by an equal, integer number of atomic mass units relative to a corresponding unlabeled tag.

In some embodiments, the overall design approach is to co-optimize the above factors using a mixture of CAD tools and available empirical data and then iterate the designs and algorithms based upon experimental data. It is expected that the tag design tools and principles developed here can prove generally valuable.

In a preferred embodiment, each peptide tag is separable from its parent protein via proteolysis using a common protease or proteolytic chemical. Suitable proteases include Arg-C proteinase (cleavage occurs after Arg residue), Asp-N endopeptidase (cleavage occurs before Asp), Chymotrypsin-high specificity (cleavage occurs after Phe or Tyr that is not followed by Met or Trp that is not followed by Met or Pro), Clostripain (cleavage occurs after Arg), Glutamyl endopeptidase (cleavage occurs after Glu), LysC (cleavage occurs after Lys), Pepsin (cleavage occurs after Phe or Leu at pH 1.3), Proline-endopeptidase (cleavage occurs after Pro not followed by Pro), Proteinase K (cleavage occurs after Ala/Glu/Phe/Ile/Leu/ThrNal/Trp/Tyr), Staphylococcal peptidase I (cleavage occurs after Glu), Thermolysin (cleavage before Ile/Leu/Val/Ala/Met/Phe that are not preceded by acidic residues and not followed by Pro), Thrombin (recognition site is Gly-Arg-Gly and cleavage occurs after Arg), Tobacco Etch Virus (TEV) protease (recognition sequence is Glu-Asn-Leu-Tyr-Phe-Gln-(Gly/Ser) and cleavage occurs between the Gln and Gly/Ser residues), Factor Xa protease (recognition sequence is (Ile/Ala)-(Glu/Asp)-Gly-Arg and cleavage occurs after Arg), enterokinase (recognition sequence is Asp-Asp-Asp-Asp-Lys and cleavage occurs after Lys), caspases (recognition sequence is X-X-X-Asp and cleavage occurs after Asp), GranzymeB (recognition sequence is Ile-Glu-Pro-Asp and cleavage occurs after Asp), GE's PreScission protease (recognition sequence is Leu-Glu-(Val/Ala/Thr)-Leu-Phe-Gln-Gly-Pro and cleavage occurs between Gln and Gly), trypsin (cleavage occurs after Lys or Arg that is not followed by Pro), or any combination there of. Alternatively, the proteome may be digested with a proteolytic chemical. Suitable chemicals include BNPS-Skatole (cleavage occurs after Trp), cyanogen bromide (cleavage occurs after Met), Formic acid (cleavage occurs after Asp), hydroxylamine (cleavage occurs after Asn and before Gly), iodosobenzoic acid (cleavage occurs after Trp), 2-nitro-5-thiocyanobenzoic acid (cleavage occurs before Cys), or any combination thereof.

Figure 2:
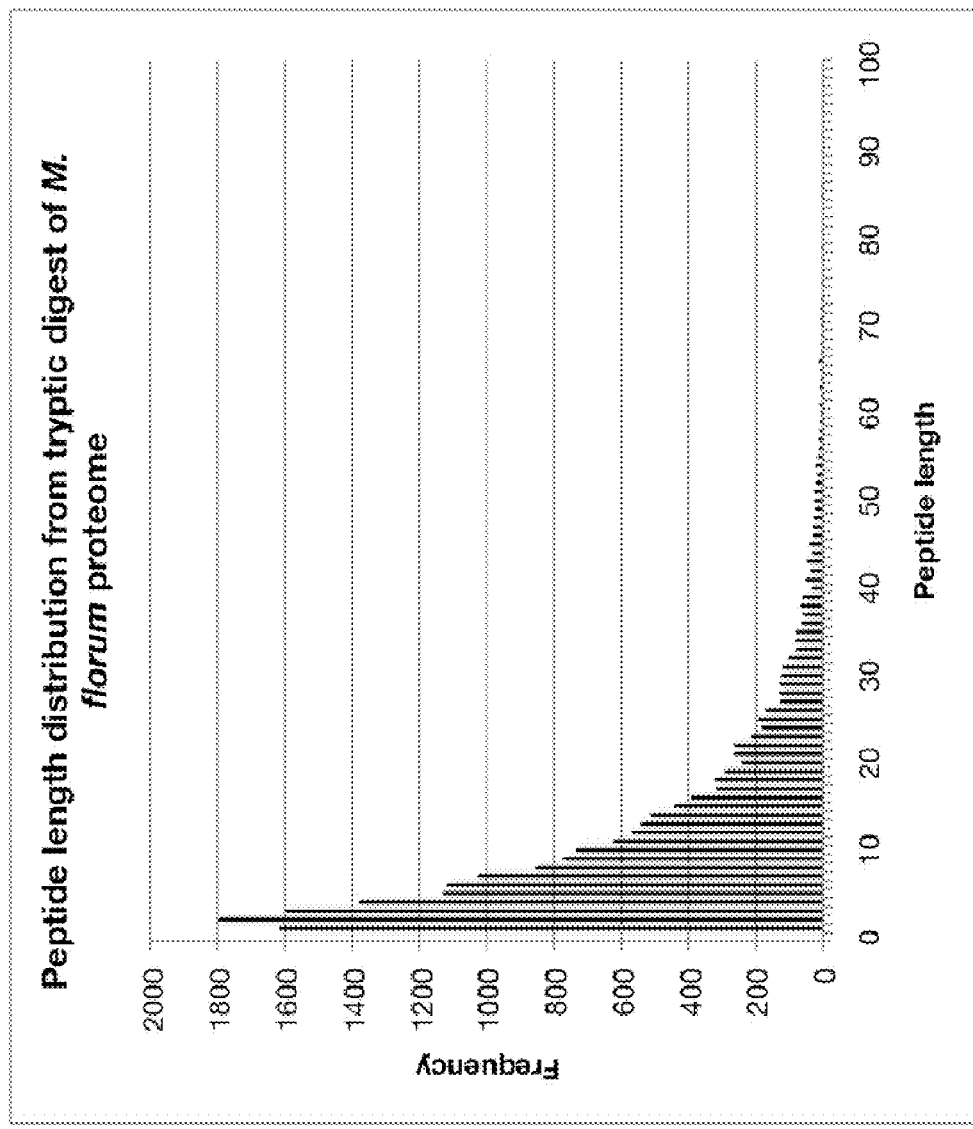
FIG. 2 illustrates the distribution of peptide lengths resulting from tryptic digest of the M. florum proteome. The frequency decreases as a function of peptide length.

In a preferred design, the release of the peptide tags from the mature proteins by the protease would generate tags having a length that could be easily separated away from any other peptides produced by proteolysis. For this reason, proteases having a sufficiently large recognition site to minimize the number of natural cleavage sites within the proteome and yet does not over-constrain the amino acid composition and sequence of the peptide tag sets are preferred. Trypsin has a short recognition sequence with 29,721 cleavage sites within the proteome of the example host organism *M. florum* (Table 1 and FIG. 2). In contrast, Factor Xa, Tobacco Etch Virus (TEV), and GE PreScission proteases have longer recognition sequences with only 22, 36 and 0 cleavage sites, respectively. Although trypsin is a robust, stable protease that can be obtained at very high purity and has significant utility in general protein analysis, the large number of cleavage sites within even the very small proteome of *M. florum* means that proteolysis can produce a large number of peptide fragments from the native proteome. Many of these peptide fragments could overlap in size with the designed peptide tags (2,658 fragments are 8-10 amino acids in length), increasing the sample complexity that must be analyzed by MS. Such a complex mixture may likely necessitate an LC or similar separation step prior to MS analysis. Since LC separation can take between 15 minutes and 4 hours per sample depending on the gradient, it may be preferred to avoid LC if possible to decrease the time per measurement. Hence, the preferred approach is to use a protease with a longer recognition site like Factor Xa, TEV or GE's PreScission to eliminate issues around separation of peptide tags from the background proteome. In some embodiments, most or all native Factor Xa or TEV cleavage sites can be avoided via gene deletion or mutation. It should be noted that the sequence and composition of peptide tags can be designed to accommodate the longer recognition site, particularly those positioned on the N-terminus. In certain embodiments, more than one protease recognition site can be used. For example, a combination of a long recognition site and a short recognition site can be included in the peptide tags. Accordingly, when releasing the peptide tags from their corresponding proteins of interest, a combination of two proteases can be used; that is, one protease for the long recognition site and the other protease for the short recognition site.

TABLE 1

Candidate proteases for proteolysis of the protein complement of *M. florum*, their cleavage sites and the number of sites in the *M. florum* proteome.

| Protease | Cleavage site | Number of sites |
|---|---|---|
| Trypsin* | K,R ↓ not P<br>W-K ↓ P<br>M-R ↓ P | 29,721 |
| TEV | E-X-X-Y-X-Q ↓ G,S | 36 |
| Factor Xa | A,F,G,I,L,T,V,M-D,E-G-R ↓ X | 22 |
| GE's PreScission | L-E-V-L-F-Q ↓ G-P | 0 |

Proteases with longer recognition sites result in a significantly smaller number of peptides than trypsin.
The cleavage position is indicated by ↓.
Residue positions are separated by -.
X denotes any amino acid.
Limited sets of amino acids at a particular position are specified by commas-separated lists.
*There are four exceptions to this trypsin cleavage site motif that are not listed here.

Additional key factors in protease selection include its cleavage efficiency and specificity: suitable protease should completely digest the proteome while still maintaining specificity for its recognition site(s). Cleavage efficiency can vary based on the surrounding protein context, so in some cases it may be necessary to add spacer residues to separate the protease site from the rest of the parent protein. Alternatively, if using a thermostable or solvent-stable protease with a long recognition site, it is possible perform the proteolytic cleavage under denaturing or partially denaturing conditions, thereby improving access of the protease to the cleavage site. In addition to Factor Xa, TEV and GE's PreScission, there are several additional proteases with long recognition sites, including enterokinase, caspases, and GranzymeB. Alternatively, tryptic digestion coupled to either an LC step or an affinity purification can be used for tag isolation.

In some embodiments, the peptide tags can include an affinity tag therein to facilitate enrichment of the peptide tags in the sample and/or purification of the peptide tags from the background proteome. Such enrichment or purification can be achieved via any suitable affinity chromatography technique known in the art. The affinity tag can be common to all peptide tags or to a subset thereof. Suitable affinity tags include AU1 (recognition sequence Asp-Thr-Tyr-Arg-Tyr-Ile), AU5 (recognition sequence Thr-Asp-Phe-Tyr-Leu-Lys), Bacteriophage T7 epitope or T7-tag (Met-Ala-Ser-Met-Thr-Gly-Gly-Gln-Gln-Met-Gly), Bacteriophage V5 epitope or V5-tag (Gly-Lys-Pro-Ile-Pro-Asn-Pro-Leu-Leu-Gly-Leu-Asp-Ser-Thr), B-tag (recognition sequence Gln-Tyr-Pro-Ala-Leu-Thr), Myc (recognition sequence Glu-Gln-Lys-Leu-Ile-Ser-Glu-Glu-Asp-Leu), E2-tag (recognition sequence Ser-Ser-Thr-Ser-Ser-Asp-Phe-Arg-Asp-Arg), FLAG (recognition sequence Asp-Tyr-Lys-Asp-Asp-Asp-Lys), Glu-Glu or EE-tag (recognition sequence Glu-(Tyr/Phe)-Met-Pro-Met-Glu), HA (recognition sequence Tyr-Pro-Tyr-Asp-Val-Pro-Asp-Tyr-Ala), HAT (recognition sequence Lys-Asp-His-Leu-Ile-His-Asn-Val-His-Lys-Glu-Phe-His-Ala-His-Ala-His-Asn-Lys), HSV-tag (recognition sequence Gln-Pro-Glu-Leu-Ala-Pro-Glu-Asp-Pro-Glu-Asp), KT3 (recognition sequence Lys-Pro-Pro-Thr-Pro-Pro-Pro-Glu-Pro-Glu-Thr), Myc (recognition sequence Cys-Glu-Gln-Lys-Leu-Ile-Ser-Glu-Glu-Asp-Leu), NorpA (recognition sequence Thr-Glu-Phe-Cys-Ala), Polyarginine or Arg-tag (recognition site of 5-6 Arg amino acids), Polyaspartate or Asp-tag (recognition sequence of 5-16 Asp amino acids), Polycysteine or Cys-tag (recognition sequence of 4 Cys amino acids), Polyhistidine or His-tag (recognition sequence of 2-10 His amino acids), Polyphenylalanine or Phe-tag (recognition sequence of 11 Phe amino acids), S1-tag (recognition sequence of Asn-Ala-Asn-Asn-Pro-Asp-Trp-Asp-Phe), S-tag (recognition sequence of Lys-Glu-Thr-Ala-Ala-Ala-Lys-Phe-Glu-Arg-Gln-His-Met-Asp-Ser), Strep-tag (recognition sequence Ala-Trp-Arg-His-Pro-Gln-Phe-Gly-Gly or Ala-Trp-Ala-His-Pro-Gln-Pro-Gly-Gly), StrepII-tag (recognition sequence of Trp-Ser-His-Pro-Gln-Phe-Glu-Lys), Universal (recognition sequence of His-Thr-Thr-Pro-His-His), VSV-G (recognition sequence of Tyr-Thr-Asp-Ile-Glu-Met-Asn-Arg-Leu-Gly-Lys), or any combination thereof.

In some embodiments, a cell can be selected or engineered to be auxotrophic for one or more specific amino acids and must rely on import from the culture medium. These amino acids can be designed to be included at a fixed number of instances in the peptide tags. Thus, when the cells are grown in medium containing those specific and isotopically labeled amino acid(s), each peptide tag can be isotopically labeled. Hence, every peptide tag having incorporated the specific, labeled amino acid(s) will be shifted by an equal, integer number of atomic mass units relative to a corresponding unlabeled tag, allowing the labeled tags to be distinguished from unlabeled tags in, for example, mass spectrometry.

Another aspect of the peptide tag design architecture is to ensure that the introduced tags do not interfere with protein function. While it is difficult to predict a priori which tag designs will be deleterious to protein function, steps can be taken to minimize this possibility. First, for proteins whose homologs have been successfully purified previously via affinity tag protein purification, the tag can be placed at the same terminus to which the affinity tag was previously fused. Collecting such knowledge requires a survey of the published literature and online enzyme databases like BRENDA [Chang, 2009]. Second, for proteins with available structural data, the tag can be added to whichever protein terminus residues are disordered and therefore likely to be flexible and tolerant of a peptide tag fusion. If no structural data is available, then secondary structure prediction algorithms can be used to inform whether a particular terminus is likely to be disordered. Where possible, the peptide tag can be preferentially introduced on the C-terminus so that the peptide tag sequence is not constrained by the protease cleavage site and so that the tag does not interfere with any N-terminal signal sequences that may be present. For proteins that cannot tolerate either N- or C-terminal peptide tag fusions, the preference can be to eliminate them from the proteome by gene deletion. In the rare case that a particular protein is essential for cell viability and cannot tolerate peptide tag fusions on either the N- or C-terminus, it is possible to add an internal peptide tag, for example between protein domains.

By making use of designed peptides rather than naturally occurring peptides for quantification of the parent protein during mass spectrometry analysis, the possibility of tailoring the tag sequence for analysis by MS is open. Given that there are 19 amino acids with unique masses (leucine and isoleucine are isomers), there are a large number of possible sequence compositions for even short tags. For example, for an 8 amino acid tag, there are over 1.5 million possible sequence compositions ranging in mass from 456 to 1489 AMU. Note that one may choose to further limit the number of possible amino acids in the tags by avoiding problematic amino acids. For example, glutamine and lysine's masses differ by less than 0.04 AMU and thus can be hard to distinguish except by high resolution MS analysis. As a second example, some amino acids are prone to derivatization during sample preparation due to their reactive side chains and thus might be avoided. The equation below yields the number of possible sequence compositions, given the number of possible amino acids (N) and the length of the tag (r).

$$F(N, r) = \left(\frac{(N+r-1)!}{r!(N-1)!}\right)$$

Figure 3:
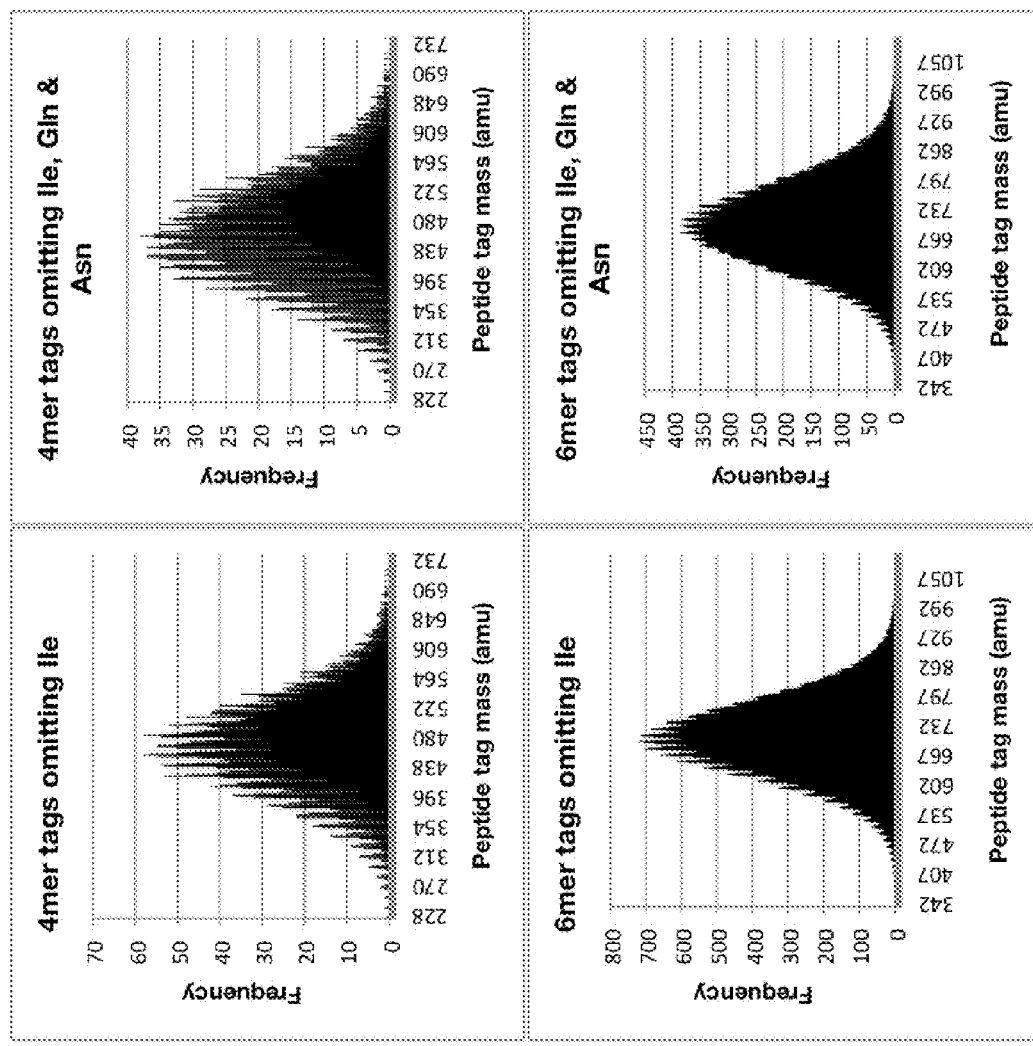
FIG. 3 is a plot of frequency versus peptide mass for all possible 4 and 6 amino acid tags with unique sequence composition (top and bottom plots, respectively). Longer peptide tags have a wider mass range from which to draw tags but also have a high number of tags with coincident masses. The size of the amino acid pool is either 19 or 17 amino acids (left and right plots, respectively). By omitting glutamine and asparagine which have similar masses to other amino acids, the frequency of tags with coincident masses can be reduced. To generate these plots, a very conservative estimate of a 1.0 atomic mass unit ("AMU") resolution on the instrument and bin peptide tag masses accordingly was assumed. (For simplicity, the x axis corresponds to mass rather than mass to charge ratio which is the actual basis for MS.) Use of a higher mass resolution would reduce the frequency of peptides with coincident masses. All calculations used monoisotopic amino acid masses.

Even with a restricted set of amino acids, some of these sequence compositions may have similar mass to charge ratios that are not resolvable by mass spectrometry analysis. In FIG. 3, the frequency is plotted as a function of mass for peptides of a given length and sequence composition, assuming a very conservative mass resolution of 1.0 AMU. Specifically, FIG. 3 is a plot of frequency versus peptide mass for all possible 4 and 6 amino acid tags with unique sequence composition (top and bottom plots, respectively). Longer peptide tags have a wider mass range from which to draw tags but also have a high number of tags with coincident masses. The size of the amino acid pool is either 19 or 17 amino acids (left and right plots, respectively). By omitting glutamine and asparagine which have similar masses to other amino acids, it is possible to reduce the frequency of tags with any given mass. To generate these plots, a very conservative estimate of a 1.0 AMU resolution on the instrument is assumed and peptide tag masses are binned accordingly. (For simplicity, the x axis corresponds to mass rather than mass to charge ratio which is the actual basis for MS.) Use of a higher mass resolution would reduce the frequency of peptides with coincident masses. All calculations used monoisotopic amino acid masses.

Referring to FIG. 3, peptides with different sequence compositions can have overlapping masses and thus are likely to have overlapping mass to charge ratios when analyzed by MS, particularly given multiple possible charge states and isotope variation. Hence, in some embodimemts, peptide tags need to be carefully designed in sets to ensure that each tag in the set has unique MS spectra given other peptide tags in the set. Peptide tags may be further designed to ensure that each tag is also unique, given the presence of isotopically labeled versions of each peptide tag. The MS can have sufficient mass to charge ratio range to uniquely resolve hundreds to thousands of peptide tags.

In addition to ensuring that the peptide tags are resolvable by MS analysis, it may also be necessary to ensure that the peptide tags are each detectable by MS analysis. To be detectable, all peptide tags can be designed to ionize with reasonable efficiency. Yet peptides can span ~4 orders of magnitude in observed ionization efficiencies using traditional Electrospray Ionization (ESI) methods for MS analysis, depending on amino acid sequence and composition [Ficarro, 2009]. Differences in ionization efficiency cannot be commonly predicted from sequence alone with complete accuracy, though some studies have been done [Cech, 2000; Cech, 2001; Frahm, 2007]. Hence, it is not trivial currently to design peptides that will ionize well. Nevertheless, in support of targeted proteomics, tools have been evolved to predict proteotypic peptides that are readily detectable by MS from collections of all possible peptides produced by trypsin digest of proteomes [Mallick, 2007; Fusaro, 2009; Webb-Robertson, 2010].

For example, Pacific Northwest National Laboratory provides the STEPP software which uses support vector machines technique to evaluate proteotypic peptides. These rules can be reversed to support forward engineering of tags that ionize efficiently. Moreover, there exist repositories (e.g., PeptideAtlas) of significant amounts of LC-MS data from diverse sources that can be used to extract relevant data concerning ionization efficiency. By mining this information, putative design rules can be developed for peptides that ionize efficiently. It is possible then to test these design rules by making synthetic peptides with different sequences and analyzing them by MS to verify whether they ionize well or not. By iterating on possible peptide sequences, synthesizing peptides, and then testing detectability by MS, a set of validated design rules can be developed to guide tag design. As an additional challenge, ion suppression effects can arise when analyzing complex peptide mixtures by MS [King, 2000; Cottingham, 2006]. For example, a change in concentration of some subset of peptide tags, as the direct result of a change in a protein concentration, may indirectly affect the ionization efficiency of other peptide tags within the peptide mixture, thereby giving a false indication of a concentration change for the other peptide tags. These issues too can only be tested via iterations of experimentation.

In a preferred embodiment, the sequences of the peptide tags are derived from the sequences of known MS standards. Example sources of MS standards include, but are not limited to, angiotensin I, angiotensin II, leu enkephalin, vasoactive intestinal peptide, glu-fibrinogen, bradykinin, ACTH, allantain, RASG-1, enolase T35, enolase T37, angiotensin II phosphate, renin substrate, mellitin, trypticdigested peptides from bovine serum albumin, tryptic-digested peptides from beta-galactosidase, calcitonin and cholecystokinin.

In some embodiments, it can be preferable to design the peptide tags to not only ionize well but also to have consistent ionization efficiency across the peptide tag set. Currently, quantitation by MS analysis alone is limited because peptides that ionize well may appear to be more abundant than peptides that ionize poorly, despite having equal abundance in the experimental sample. If all peptide tags have equivalent ionization efficiencies with minimal ionization suppression effects, it would be possible to compare protein abundances within a single experimental sample directly by MS, as opposed to the relative quantification approaches used now. Such a technical feat would be a huge leap forward in terms of the utility of MS analysis for routine measurement of cell state and is only possible using the designed peptide tag approach described here. However, even in the absence of a peptide tag set with similar ionization efficiencies, it can still be possible to make use of stable isotope labeled peptides to quantify protein levels by MS.

Methods for Introduction of Peptide Tags into a Host Cell or Organism

To add peptide tags to all proteins of interest so that they are readily measurable via MS, it may ultimately be necessary to introduce a few hundred changes to the genome of the host organism or host cell of interest. A preferred approach is to rebuild sections of the host cell's or host organism's genome in parallel. Each section can span multiple genes and can encode tagged versions of those genes. As sections are built, each section can be integrated onto the genome via methods known to those skilled in the art. Such an incremental approach ensures that the viability of the engineered strain is not compromised during redesign. Robustness of the genome modifications performed can be monitored by measuring cell doubling times after modifications are made.

A key aspect of any targeted homologous recombination strategy used is that it can support iterative recombination on the genome. For many homologous recombination strategies, a single recombination step can result in the insertion of an antibiotic selection marker into the genome so that cells that have undergone recombination can be distinguished from cells that have not. Hence, to perform gene insertions or deletions at multiple, noncontiguous locations in the genome, it may be necessary either to use multiple resistance markers or to remove/inactivate the selection marker so that it can be reused elsewhere. To support unlimited iterations of gene deletion/insertion on the genome, the latter approach is preferred. In the first recombination step, not only the antibiotic selection marker but also a counter-selectable marker such as upp, pheS, sacB, pyrF, thyA, lacY, etc. [Kast, 1994] can be inserted. For example, pheS encodes a mutant form of the phenylalanine tRNA charging enzyme which can incorporate p-chlorophenylalanine in addition to the normal amino acid. Incorporation of this unnatural amino acid is lethal. Hence, in a second round of recombination, deletion of both the antibiotic resistance marker and the mutant PheS by growing the cells in the presence of p-chlorophenylalanine can be selected. This type of two-round recombination strategy has been successfully used in organisms like *E. coli* for seamless genome editing [Sharan, 2009]. Another excellent counterselectable marker is the upp gene. The naturally occurring upp gene incorporates uracil into UTP. The presence of the gene allows incorporation of the base analog 5-fluorouracil, which is lethal. Strains which are upp– are insensitive to 5-fluorouracil. Introduction of the upp gene as part of a modification cassette allows selection for the cassette removal by growth in the presence of 5-fluorouracil.

Figure 4:
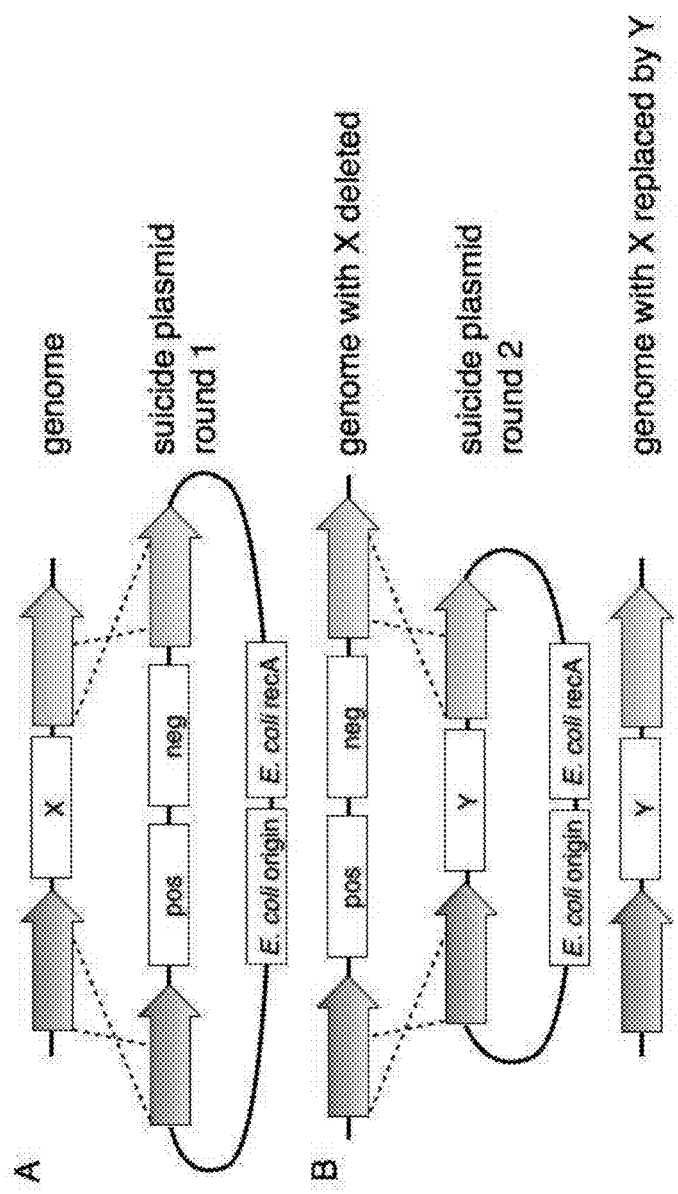
FIG. 4 illustrates a schematic of an iterative approach to E. coli RecA-mediated homologous recombination in M. florum. (A) In the first round of homologous recombination, genomic fragment X is replaced by one or more selection markers via a double crossover recombination event. A positive selection marker, such as an antibiotic resistance cassette, is indicated by "pos". A negative selection marker, such as the counter-selectable marker pheS, sacB, pyrF, thyA, etc., is indicated by "neg". The selection markers are flanked by regions that are homologous to the intended site of recombination. Since the plasmid lacks a Mycoplasma replication origin, it is unable to replicate in M. florum and is referred to as a suicide plasmid. (B) To ensure that the recombination process can be done at multiple, noncontiguous locations on the genome, a second round of recombination is performed to replace the selection markers with a new DNA fragment Y. In the case of gene deletions, Y represents a null or non-coding fragment.

To enhance the efficiency of recombination, recombinase proteins may be expressed in the host cell or organism of interest. For example, expression of *E. coli* recA (ecRecA) can increase the efficiency of recombination in a *Mycoplasma* species by >30-fold [Allam, 2010]. As an illustrative example, an iterative homologous recombination system for *M. florum* can be based on heterologous expression of ecRecA (FIG. 4). Alternatively, a RecET-based recombination system may be developed to enhance the efficiency of targeted recombination. RecET catalyzes efficient recombination in *E. coli* [Muyrers, 2004] and has also been demonstrated in other organisms. The crucial enzyme in this system is RecT, a phage recombinase. RecE simply provides 5' exonuclease activity for linear DNA fragments. For example, a recT homolog has been identified in *Spiroplasma citri* and thus may be used to enhance recombination efficiency in *M. florum*. In addition to RecA- and RecET-mediated recombination, systems based on Cre-lox recombination and/or lambda RED recombination can be used. Finally, a systematic search can be conducted for native phages in the host cell or organism of interest that may yield additional phage integration parts to enhance recombination.

An alternative method for introducing the genetically-encoded peptide tags into the genome of a host organism or host cell is oligo-mediated allelic replacement [Ellis, 2001; Wang, 2009]. In this approach, single-stranded oligonucleotides (oligos) are transformed into the host strain via electroporation to introduce short insertions, deletions or mutations into the host genome. Since oligo-mediated allelic replacement does not rely on selection markers, it is necessary to verify successful introduction of the desired genome modification by sequencing. Hence, the key technical challenge of this approach is ensuring that conditions are optimized to support efficient oligo recombination so that a successfully modified clone can be found by sequencing a relatively small number of colonies. Based on prior work done in *E. coli*, it is possible to optimize several different parameters to influence the efficiency of oligo-mediated allelic replacement, including oligo length, GC content, and oligo concentration. As an additional challenge, oligo-mediated allelic replacement can result in unintended changes elsewhere in the genome, therefore it may be necessary to regularly sequence the genome of the modified strains to verify the integrity of the introduced tags. In *E. coli*, oligo recombination is usually done in conjunction with the bacteriophage λ Red system to boost efficiency.

Fortunately, recombinases similar to that in the λ Red system are widespread in many bacteria [Datta, 2008], suggesting that it is possible to implement oligo-mediated allelic replacement in other host cells and host organisms. Moreover, recent reports indicated that there is also Red-independent oligo recombination in gram-negative bacteria [Swingle, 2010]. Hence, it is possible that oligo-mediated recombination may work without a functional λ red or equivalent system in the host cell. As a final option for introducing tagged versions of the protein coding sequences into a host cell or host organism, recently published techniques can be used for complete chemical genome synthesis and transplantation [Gibson, 2008, Gibson, 2008b; Lartigue, 2009; Gibson, 2010].

In some embodiments, the peptide tags are fused to proteins of interest and those proteins are then heterologously expressed in a host cell or host organism via methods known to those skilled in the art. The DNA encoding tagged heterologous proteins of interest may be inserted in the host cell via several different suitable methods known in the art, such as a plasmid, transposon insertion or homologous recombination. The heterologous protein may comprise a metabolic pathway, a regulatory network or other engineered system of interest.

Further Modification of the Genome of a Host Cell or Host Organism

Natural biological systems did not evolve to be good substrates for synthetic biology. For example, even simple organisms like *M. florum* have genes that are not necessary for growth in laboratory conditions and are therefore candidates for deletion. Based on techniques developed by other groups [Glass, 2006; French, 2008], extensive gene knockout studies can be carried out to establish which genes are individually dispensable under laboratory growth conditions, without adversely impacting growth rate. Such genes are candidates for gene deletion and genome simplification of the host cell or organism. The elimination of all transposable elements has been demonstrated, suggesting that significant genome redesign is tractable in *E. coli* [Posfai, 2006].

As an illustrative example, extensive gene knockout studies have been carried out in the present invention in *M. florum* generating approximately 3100 viable transposon insertion events. This work has established that 336 genes are individually dispensable under laboratory growth conditions (e.g., result in a viable strain). Based on this library of transposon insertion mutants, the growth rates of each member of a curated library of transposon insertion mutants were measured and 94 candidate genes for deletion that maintained robust growth rates under laboratory conditions were identified (doubling time less than 60 minutes). Based on this analysis, candidate genes for deletion can include, but are not limited to, ksgA, truA, bglA, folD, bglA, Mfl168, Mfl015, guaC, Mfl031, frvB, Mfl032, Mfl182, lplA, Mfl184, pdhA, Mfl194, ackA, sun, tatD, recA, Mfl051, ptsG, polA, add, pepA, Mfl216, rplI, Mfl224, pldB, Mfl225, Mfl103, smc, Mfl104, pstCA, upp, Mfl238, spoU, spoU, Mfl262, Mfl375, Mfl263, pepQ, Mfl272, ftsZ, apt, lon, Mfl280, ruvA, Mfl300, Mfl429, parC, bg1H, Mfl313, Mfl437, Mfl315, Mfl448, Mfl318, Mfl458, Mfl325, Mfl461, Mfl329, Mfl483, Mfl335, Mfl489, Mfl338, Mfl505, tkt, Mfl506, Mfl358, scrA, Mfl369, farR, rhel, potE, scrB, rbsB, treP, Mfl670, rnhB, Mfl681, Mfl546, Mfl548, Mfl551, rluC, Mfl574, Mfl606, Mfl610, xylR, Mfl619, Mfl627, tdk, Mfl645, Mfl647, ychF and combinations thereof.

To further inform the genome simplification efforts, it is possible to use a sequencer (e.g., the Illumina Genome Analyzer II) to sequence multiple strains and closely related species of a host cell or organism of interest. The resulting genome sequences can be used for a comparative genomics study, providing insight into viable polymorphisms, missing or additional genes, genome organization (synteny) and viable rearrangements in closely related organisms. This information is particularly useful to identify genes that are more amenable to deletion from the chromosome without impact on viability or cell physiology.

Based on the transposon deletion library and comparative genomics analysis of the host cell or host organism, unnecessary genes can be deleted from the genome, in particular, genes that encode transcripts or proteins that are difficult to quantify or difficult to distinguish from other gene products.

It is common practice in synthetic biology to make use of physicochemical models to inform design of biological systems. However, the accuracy of these models is often compromised by their inability to fully account for all the relevant parameters and interactions from the host organisms that influence system behavior. The present invention can be used to redesign the host genome of the cell or organism of interest to be simpler and easier to model, building upon previous efforts with other organisms [Chan, 2005]. Specifically, aspects of the present invention provides methods to (1) codon randomize genes to eliminate cryptic regulatory motifs, transposon insertion sites, RNase sites and RNA second structure elements, (2) to replace promoters and ribosome binding sites of genes whose expression levels are difficult to predict with standardized parts, and (3) to decouple overlapping genetic elements. It may be challenging to eliminate all aspects of the cell that are difficult to model. In particular, fundamental physical phenomena like local concentration or stochastic effects are unavoidable. Nevertheless, the ability to redesign the entire organism to simplify those aspects of the cell that are difficult to simulate is a significant advantage of the present approach compared to other groups who focus on modeling natural organisms only.

All standard, genetic parts that can be designed for a host cell or organism of interest should adhere to a general set of design rules:

Avoid any codons that are unused in the host cell.
Avoid any sequences that are cut by native restriction systems in the host cell. Alternatively, it is possible to delete the native restriction system from the cell.
Recode all stop codons as TAA.
Eliminate key restriction sites so that the parts are compatible with widely used DNA assembly standards (such as BioBrick assembly standards 10, 21, 23 or 25) or DNA assembly methods.
Avoid any direct or inverted repeats, high GC content regions, high AT content regions or nucleotide homopolymers that would make the part difficult to synthesize via commercial gene synthesis. Many of these features also make sequencing, especially on next-generation sequencing platforms, problematic.
Avoid transposon insertion sites that would make the part vulnerable to mutation.
Avoid incidental regulatory motifs, RNase cleavage sites or RNA secondary structure elements that would lead to unpredictable gene regulation effects.
Design operons to minimize spurious transcriptional or translational initiation.
Design protein coding genes such that the corresponding protein does not contain undesirable proteolytic cleavage sites.
Design protein coding genes such that the corresponding protein does not contain sequences that may lead to spurious protein binding during affinity purification.
Design protein coding regions to reduce potential translational frameshifts.

As such, these design rules can be encoded within a DNA design program to facilitate design of new genetic parts for a host cell or organism of interest.

Cell State Measurements

To enable use of the engineered strains by the broader synthetic biology community, the present invention provides methods and systems for routinely measuring cell state, e.g., in a *M. florum* or *E. coli* sample. Off-the-shelf, commercially available instruments can be used for measurements. However, it is also possible to develop new, potentially more capable, lower cost and more user-friendly MS instrumentation that is specifically targeted to the engineered strains.

One advantage of the present invention is to enable the routine analysis of the cell state of the engineered strains. An important aspect of data analysis would be to reliably compare results across different designed strains and at different times. Hence, it may be important to grow strains under consistent and comparable conditions to ensure reproducible results. Use of a defined medium in which all components are well-specified may enhance the reproducibility of results. By standardizing growth conditions, mRNA and protein levels may be more reproducible across measurements. Moreover, such work can support analysis efforts since isotopically labeled nutrients eliminate the confusion from foreign proteins found in media when performing proteomic analysis.

As an illustrative example, due to its rather limited metabolic repertoire, *M. florum* requires a complex array of nutrients for growth and, to date, a minimal defined medium has not been developed for *Mesoplasma*, unlike other Mollicutes [Hackett, 1995]. To standardize growth conditions for *M. florum*, a minimal medium can be defined that supports culture growth. Previously, a systematic metabolic network analysis of the Mollicute *Mycoplasma pneumoniae* led to the successful development of a defined medium [Yus, 2009]. Similarly, a prediction of minimal medium components was generated for the related organism *Mycoplasma genitalium* through large-scale metabolic modeling, but this prediction has not been tested experimentally [Suthers, 2009]. Using similar approaches, a defined medium may be developed for *M. florum*.

It is also possible to build turbidostats that indefinitely maintain *M. florum* cultures under constant conditions. The system would monitor cell density in a fixed-volume chamber and add fresh medium as the culture grow, ensuring that cell state can be analyzed under well-defined and highly-reproducible conditions. Turbidostats can be made from a LED light source, a photodiode, two peristaltic pumps, two solenoid pinch valves, and a stirrer.

Transcriptome data provides useful insights into gene regulation in the cell. The transcriptome of host cells or host organisms, including engineered strains, can be measured by RNA-seq [Nagalakshmi, 2008; Gibbons, 2009; Oliver, 2009]. RNA-seq is a particularly interesting approach because it can accurately identify and count RNA molecules for several strains in parallel, rapidly and at low cost. RNA-seq also offers more flexibility for synthetic biology applications since the same procedures and reagents are used for all strains, independent of genome sequence. In contrast, for microarray-based transcriptome analysis, new microarrays need to be designed and manufactured for each new host strain. Moreover, additional useful information such as transcriptional start and end sites, operon structure, transcript directionality, and the presence of unannotated genes, including non-coding RNA species, can be obtained from the same data. With current technology (Illumina Genome Analyzer), a full transcriptome could be analyzed in approximately 2-3 days for less than $100, provided that several samples are multiplexed and sequenced simultaneously. It is anticipated that the cost and time required to accomplish these experiments will decrease substantially in the next 2-3 years, especially with the advent of real-time sequencing instruments capable of generating data in just a few minutes. In brief, RNA-seq involves RNA fragmentation to increase sequencing coverage uniformity, polyadenylation of the molecules, and ligation of a 5'-adaptor followed by a reverse-transcription PCR step. The cDNA molecules are then directly used for sequencing, and the reads are aligned to the corresponding reference genome, allowing us to count how many reads are found for each gene or annotated genomic feature. Recent studies have demonstrated significant correlation between RNA-Seq quantitative transcriptome measurements and quantitative proteomic profiling via MRM measurements [Pavelka, 2008].

If needed, the genome of the host cell or host organism can be redesigned to eliminate regions with repetitive, high GC content and significant secondary structure that confound RNA analysis by RNA-seq. Leveraging next generation sequencing platforms for nucleic acid analysis is particularly attractive, since increasing demand for low-cost personal genome sequencing is driving down sequencing instrumentation and reaction costs significantly over time. In the event that RNA-seq is inadequate or not desired for a particular application, microarray analysis is also possible using the same short, genetically encoded tags introduced in support of MS analysis as hybridization targets.

Figure 6:
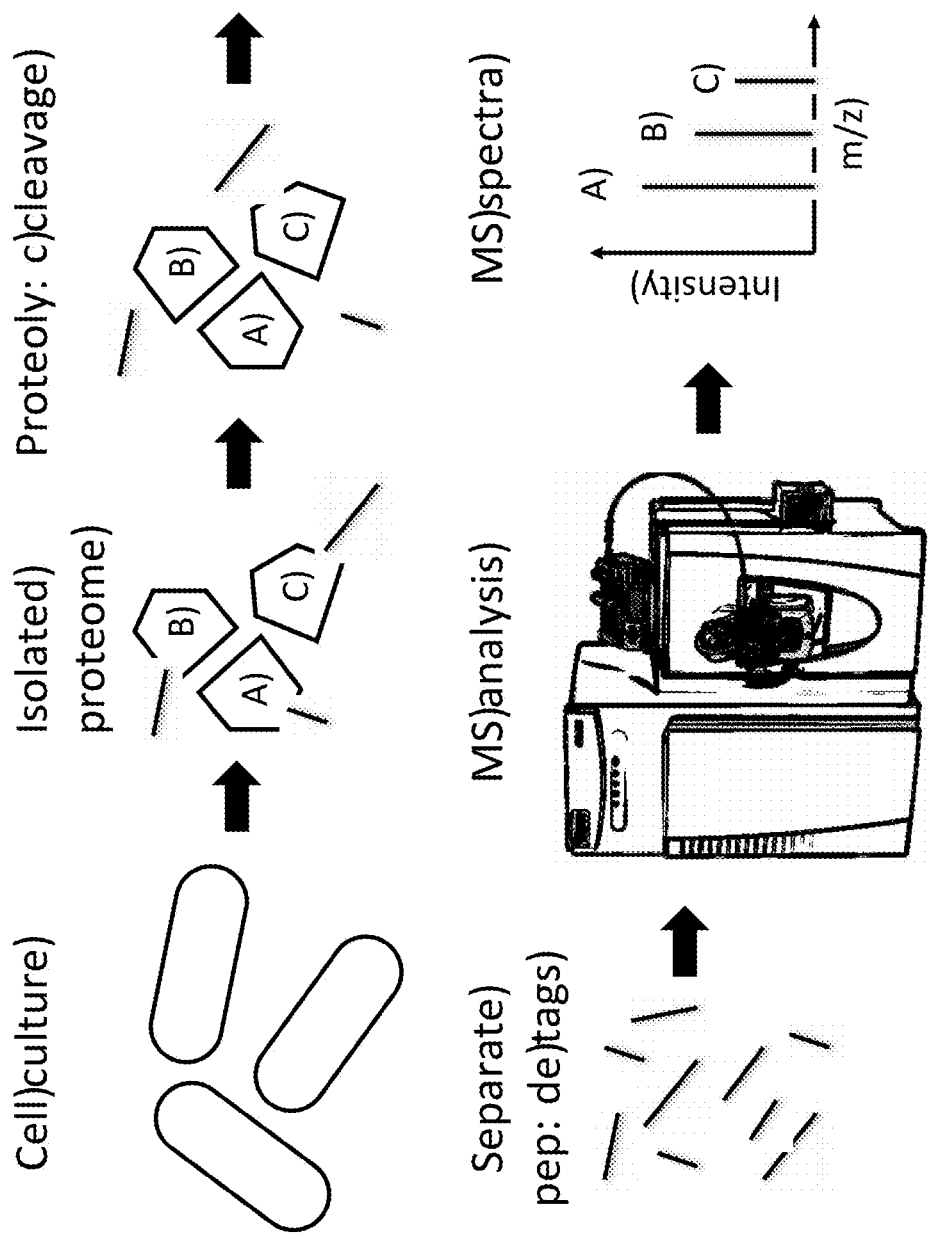
FIG. 6 illustrates a schematic of the sample preparation and mass spectrometry analysis workflow for analysis of an engineered cell according to one embodiment of the present invention. First, cells from a cell culture are pelleted. Second, the proteome of the cell culture sample is isolated. Third, the proteome sample undergoes proteolytic cleavage to separate the peptide tags from the associated proteins of interest. Fourth, the peptide tags are isolated from the background proteome, for example, via size fractionation or affinity purification. Fifth, the isolated peptide tags are analyzed by mass spectrometry (with an optional LC step). Finally, the MS analysis produces an MS spectra of each peak.

In some embodiments, methods of the present invention for measuring the proteome make use of the engineered host cell or host organism. Quantitative proteome analysis can involve the following steps. These steps can be done in high throughput 96 well plates so that protein samples from many strains can be prepared in parallel in a rapid fashion. A schematic of this process is shown (FIG. 6).

Pellet cells from cell culture by centrifugation.
Lyse cells in the presence of a protease inhibitor.
Cleave the peptide tags from their associated protein with the selected protease(s).
Separate the peptide tags from the rest of the cellular debris via ultracentrifugation or filtration or other suitable size selection approach.
If necessary, purify, enrich or separate the peptide tags from peptides stemming from the background proteome.
Analyze the tags by MS. If necessary, a fast LC or capillary electrophoresis step or suitable approach can be included prior to MS analysis to spread out the tags prior to ionization.
Using the MS data, identify the peptide tags and quantify their levels.

MS analysis alone typically does not yield quantitative information because differences in ionization efficiency among peptides leads to misleading apparent differences in abundance. Hence, most researchers use MS analysis for relative quantification, comparing a single peptide across multiple experimental conditions, as opposed to two or more peptides within a single sample. Label-free relative quantitation is based on integrated extracted ion chromatogram abundance [Bondarenko, 2002] or spectral-counting [Wolters, 2001]. However, there is dispute as to the quantitativeness of such analysis.

To achieve more reproducible relative quantitation, stable isotope labeling by amino acids in cell culture (SILAC) is now used [Ong, 2002; Ong, 2007]. SILAC relies on the fact that peptides with "light" and "heavy" amino acids have identical chemical structure and thus identical ionization efficiency. In SILAC, cells are grown under control and experimental conditions in minimal media supplemented with either light or heavy versions of an amino acid, respectively (or vice versa). After several cell doublings, the proteome of cells grown in heavy media is fully labeled and thus each peptide should be shifted by an integer number of AMU relative to the same peptide from cells grown in light media. The control and experimental samples are then mixed prior to MS analysis. By comparing the levels of light and heavy peptides, the levels of each protein in the experimental sample can be reported relative to the corresponding protein in the control sample. SILAC requires that cells be grown in defined minimal media, that the proteome of the cells grown in heavy media be completely labeled, and that the protein(s) of interest be expressed in both the control and experimental samples. In some embodiments, defined peptide tags are designed to incorporate a fixed number (for example, one or more) of a set of specific amino acid(s) in every tag. This design constraint facilitates SILAC measurements. For example, organisms, such as *M. florum* or auxotrophic *E. coli* strains, which are unable to synthesize the specific amino acid(s) can be grown in medium containing the isotopically labeled specific amino acid(s), thereby guaranteeing that each tag incorporates a fixed number of labeled amino acids. The resulting labeled peptide tags are thus easily distinguishable by MS from unlabelled tags because they are shifted by a known, consistent integer number of atomic mass units. This aspect of the present invention can be further expanded to allow labeling of many distinct protein samples, each identified by isotopic variation in the label of one or more of the specific, incorporated amino acids. With this technique it is possible to compare the proteomes of many organisms simultaneously, each grown under different conditions, or each having a different genome and/or plasmid complement.

To obtain absolute quantitative protein levels in samples, the AQUA strategy can be employed in which known concentrations of synthetic, stable isotope labeled peptides are spiked into experimental samples prior to MS analysis to serve as internal standards [Kirkpatrick, 2005]. The AQUA strategy can also be facilitated by the inclusion of a fixed number (for example, one or more) of a set of specific amino acid(s) in every tag. This design constraint guarantees that each tag has one or more labeled amino acids. Those labeled amino acids are the only ones that need to be specially prepared and used in the synthesis of the labeled peptide collection, thus dramatically reducing the cost of peptide synthesis.

Each of these methods of quantification by MS is compatible with the present peptide tagging approach. A peptide tag set with sufficiently uniform ionization efficiencies and minimal ion suppression effects allows for label-free quantitation. Alternatively, it is possible to deliberately design the peptide tags to be compatible with SILAC experiments by ensuring that the peptide tags resolve uniquely not only from each other but also from tags that have been shifted by an integer number of AMU due to the cell being grown in heavy media. Finally, for a predefined set of peptide tags, it is possible to include synthesized, labeled peptide standards in each experiment for easy absolute quantitation. Thus, a plurality of isotopically labeled peptides corresponding to the peptide tags used in the engineered cell can be provided, for use as standards for absolute mass spectrometry quantification.

Computer Software Tools and Processing Devices

In one aspect, a computer program product for designing one or more, or a plurality of peptide tags for an engineered cell is provided. The program can reside on a hardware computer readable storage medium and having a plurality of instructions which, when executed by a processor, cause the processor to perform operations. The operations can include selecting one or more, or a set of amino acid sequences having 3-25, 5-15 or 8-10 or up to 40 amino acids, for introducing into an organism one or more tags for protein(s) of interest and without affecting a function of the protein(s) of interest. Such amino acid sequence or sequence set can each have a unique mass relative to proteolytic products of the background proteome endogenous to the organism; the amino acid sequence or sequence set can also include a proteolytic cleavage site or protease recognition sequence such that the amino acid sequence(s) can be released from the protein(s) of interest upon proteolysis; and the amino acid sequence(s) can be uniquely resolvable from other peptide tags in the set at an absolute mass resolution of a mass spectrometer instrument used.

The program can further optimize the peptide tag sequences for quantitative analysis by mass spectrometry. In certain embodiments, the program can be used to design a plurality of peptide tags that have uniform ionization efficiency, minimize ion suppression effects between tags, have detectable charge state with unique mass to charge ratios at the resolution of the instrument used and are detectable by the mass spectrometer instrument used. The plurality of peptide tags can further be designed to contain a fixed number of a specified set of amino acids (one or more) to facilitate isotopic labeling of either a set of corresponding synthetic peptide standards or of the peptide tags themselves via growth in a medium containing isotopically labeled versions of the specific amino acids. Similarly, the plurality of peptide tags can further be designed to omit undesirable amino acids, such as those amino acids that are prone to derivatization in downstream analysis.

The program can further optimize the peptide tag sequences for separation and isolation from the rest of the proteome. In certain embodiments, the program can select a protease having longer than 4, 5, or 6 amino acid recognition site to minimize overlap of the amino acid sequence with the cleavage products from the background proteome. The plurality of peptide tags can be further designed to elute at different times from a liquid chromatography column or migrate differently during capillary electrophoresis. The plurality of peptide tags can be further designed to be purified or enriched from the background proteome by an affinity chromatography step through the inclusion of an affinity tag sequence.

In some aspects of the invention, another computer program product is provided for designing genetic components for an engineered cell. The program can reside on a hardware computer readable storage medium and having a plurality of instructions which, when executed by a processor, cause the processor to perform operations. In some embodiments, the operations can include but is not limited to one of the following: avoiding a codon that is not translated in the organism; avoiding a sequence that is cut by a native restriction system in the organism, or deleting the native restriction system therefrom; recoding all stop codons as TAA; eliminating key restriction sites so that the genetic components are compatible with a widely used assembly standard; avoiding direct or inverted repeats, high GC content regions, high AT content regions, or nucleotide homopolymers that can make the genetic components difficult to synthesize via commercial gene synthesis; avoiding transposon insertion sites that would make the part vulnerable to mutation; avoiding incidental regulatory motifs, RNase cleavage sites or RNA secondary structure elements that would lead to unpredictable gene regulation effects; designing operons to minimize spurious transcriptional or translational initiation; eliminating undesirable proteolytic cleavage sites in expressed proteins; and eliminating sequences in expressed proteins that may lead to spurious protein binding during affinity purification. The organism can be *M. florum* in an embodiment, where the codon that is not translated is CGG, and the sequence that is cut by the native restriction system is GATC. The widely used assembly standard can be BioBrick assembly standard 10 [Knight, 2003; Knight, 2007].

As discussed herein, some embodiments of the present invention allow for the measurement of key molecular species in the cell, including, but not limited to, the genome, RNA, and proteins, in a more user friendly and more routinely performable process. Only by making measurement of cell state routine will it be possible to ultimately develop the predictive forward design tools needed for synthetic biology. The generation of such datasets while iterating around the design-build-test cycle, may require software tools to visualize and interpret such data in order to understand the impact of engineered systems on cell state (i.e., debugging tools) and use that data to inform the next iteration of design. The measurement technologies described herein can facilitate a range of CAD tools to leverage the data produced.

For example, a data analysis workflow can include the following:

Input a model or representation of the engineered cell into the software tool. Such a representation might be mechanistic and include all known gene products and their interactions, such as via mass action kinetics. Alternatively, for some applications it may be useful to represent certain parts of the organism as modules with defined inputs, outputs and transfer functions.

Input the measurement data into the software tool. Since RNA-seq has been used previously for quantitative analysis, it is possible to use existing instrument software tools to convert the raw data into quantitative RNA levels in standard formats that can be imported for further analysis. Similarly, the software should be able to translate the data from the MS instrument into quantitative protein levels. Some of this analysis can be done with currently available software. However, the use of defined peptide tags can simplify the analysis and enable additional analysis. In certain embodiments, the software, given the library of peptide tags used, can automatically preserve data corresponding to the tags and discard any data collected on peptides from the background proteome. The software can further distinguish between isotopic variants of the peptide tags, either to separate multiplexed samples or to distinguish peptides from experimental samples from added reference standards. The levels of particular proteins of interest might further be corrected based on previously measured ionization efficiencies and/or proteolytic cleavage efficiencies of their corresponding peptide tag. A significant advantage of using peptide tags is that the software can determine with some confidence not only which proteins of interest are present in the sample and at what levels but also which proteins of interest are below the detection threshold. In conventional mass spectrometry analysis, it can be difficult to determine whether a protein is not detected because it is not present in the sample or because of ion suppression or ionization effects.

The software tool can then cluster the data on RNA and protein levels and find correlations with particular metabolic functions. A key advantage of having multiple Omics datasets is the ability to control for the noise and inherent measurement bias that plagues many computational analyses of biological systems. For example, if a particular host gene changes expression at both the RNA and protein level only when the engineered system is present, then with high confidence it can be concluded that the engineered system impacts that host gene. As a second example, if a change is identified in abundance of the gene products of several genes associated with reduction and oxidation of energy carriers, then it might be inferred that the engineered system is having a significant impact on host redox balance.

Compare the measured data to benchmark data sets. As repeated measurements of the same or similar organisms can be made across experiments using the same or similar library of peptide tags, this data can be used as a baseline to identify significant changes in particular gene products.

Various implementations of the systems and techniques described here can be realized in digital electronic circuitry, integrated circuitry, specially designed ASICs (application-specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device. Such computer programs (also known as programs, software, software applications or code) may include machine instructions for a programmable processor, and may be implemented in any form of programming language, including high-level procedural and/or object-oriented programming languages, and/or in assembly/machine languages. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

A computer program may, in some embodiments, be stored on a computer readable storage medium. A computer readable storage medium stores computer data, which data can include computer program code that is executed and/or interpreted by a computer system or processor. By way of example, and not limitation, a computer readable medium may comprise computer readable storage media, for tangible or fixed storage of data, or communication media for transient interpretation of code-containing signals. Computer readable storage media, may refer to physical or tangible storage (as opposed to signals) and may include without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Figure 5:
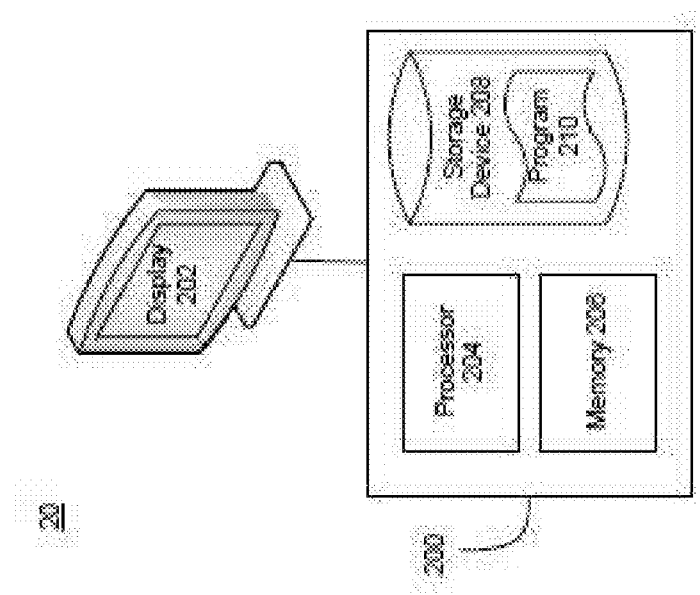
FIG. 5 illustrates a block diagram of a computing architecture.

FIG. 5 shows a block diagram of a generic processing architecture, which may execute software applications and processes. Computer processing device 200 may be coupled to display 202 for graphical output. Processor 204 may be a computer processor capable of executing software. Typical examples of processor 204 are general-purpose computer processors (such as Intel® or AMD® processors), ASICs, microprocessors, any other type of processor, or the like. Processor 204 may be coupled to memory 206, which may be a volatile memory (e.g. RAM) storage medium for storing instructions and/or data while processor 204 executes. Processor 204 may also be coupled to storage device 208, which may be a non-volatile storage medium such as a hard drive, FLASH drive, tape drive, DVDROM, or similar device. Program 210 may be a computer program containing instructions and/or data, and may be stored on storage device 208 and/or in memory 206, for example. In a typical scenario, processor 204 may load some or all of the instructions and/or data of program 210 into memory 206 for execution.

Program 210 may be a computer program capable of performing the processes and functions described above. Program 210 may include various instructions and subroutines, which, when loaded into memory 206 and executed by processor 204 cause processor 204 to perform various operations, some or all of which may effectuate the methods, processes, and/or functions associated with the presently disclosed embodiments.

Although not shown, computer processing device 200 may include various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 200.

EXAMPLES

The examples below are provided herein for illustrative purposes and are not intended to be restrictive.

Table 2 provides a summary of SEQ ID NOs:1-98 disclosed herein.

TABLE 2

| SEQ ID NO | Sequences. Name |
|---|---|
| SEQ ID 1 | Peptide tag 17696 |
| SEQ ID 2 | Peptide tag 17697 |
| SEQ ID 3 | Peptide tag 17698 |
| SEQ ID 4 | Peptide tag 17699 |
| SEQ ID 5 | Peptide tag 17700 |
| SEQ ID 6 | Peptide tag 17701 |
| SEQ ID 7 | Peptide tag 17702 |
| SEQ ID 8 | Peptide tag 17689 |
| SEQ ID 9 | Peptide tag 17690 |
| SEQ ID 10 | Peptide tag 17691 |
| SEQ ID 11 | Peptide tag 17692 |
| SEQ ID 12 | Peptide tag 17693 |
| SEQ ID 13 | Peptide tag 17694 |
| SEQ ID 14 | Peptide tag 17695 |
| SEQ ID 15 | Peptide tag 17710 |
| SEQ ID 16 | Peptide tag 17711 |
| SEQ ID 17 | Peptide tag 17712 |
| SEQ ID 18 | Peptide tag 17713 |
| SEQ ID 19 | Peptide tag 17714 |
| SEQ ID 20 | Peptide tag 17715 |
| SEQ ID 21 | Peptide tag 17716 |
| SEQ ID 22 | Peptide tag 17703 |
| SEQ ID 23 | Peptide tag 17704 |
| SEQ ID 24 | Peptide tag 17705 |
| SEQ ID 25 | Peptide tag 17706 |
| SEQ ID 26 | Peptide tag 17707 |
| SEQ ID 27 | Peptide tag 17708 |
| SEQ ID 28 | Peptide tag 17709 |
| SEQ ID 29 | Peptide tag 17724 |
| SEQ ID 30 | Peptide tag 17725 |
| SEQ ID 31 | Peptide tag 17726 |
| SEQ ID 32 | Peptide tag 17727 |
| SEQ ID 33 | Peptide tag 17728 |
| SEQ ID 34 | Peptide tag 17729 |
| SEQ ID 35 | Peptide tag 17730 |
| SEQ ID 36 | Peptide tag 17717 |
| SEQ ID 37 | Peptide tag 17718 |
| SEQ ID 38 | Peptide tag 17719 |
| SEQ ID 39 | Peptide tag 17720 |
| SEQ ID 40 | Peptide tag 17721 |
| SEQ ID 41 | Peptide tag 17722 |
| SEQ ID 42 | Peptide tag 17723 |
| SEQ ID 43 | Tag 26165 |
| SEQ ID 44 | Tag 26166 |
| SEQ ID 45 | Tag 19362 |
| SEQ ID 46 | Tag 19363 |
| SEQ ID 47 | Tag 26167 |
| SEQ ID 48 | Tag 19365 |
| SEQ ID 49 | Tag 26168 |
| SEQ ID 50 | Tag 26169 |
| SEQ ID 51 | Tag 26170 |
| SEQ ID 52 | Tag 19369 |
| SEQ ID 53 | Tag 19370 |

TABLE 2-continued

| SEQ ID NO | Sequences. Name |
|---|---|
| SEQ ID 54 | Tag 26171 |
| SEQ ID 55 | Tag 19372 |
| SEQ ID 56 | Tag 26172 |
| SEQ ID 57 | Tag 26173 |
| SEQ ID 58 | Tag 26174 |
| SEQ ID 59 | Tag 19376 |
| SEQ ID 60 | Tag 19377 |
| SEQ ID 61 | Tag 26175 |
| SEQ ID 62 | Tag 19379 |
| SEQ ID 63 | Tag 26176 |
| SEQ ID 64 | Tag 26177 |
| SEQ ID 65 | Tag 26178 |
| SEQ ID 66 | Tag 26179 |
| SEQ ID 67 | Tag 26180 |
| SEQ ID 68 | Tag 26181 |
| SEQ ID 69 | Tag 26182 |
| SEQ ID 70 | Tag 26183 |
| SEQ ID 71 | Tag 26184 |
| SEQ ID 72 | Tag 26185 |
| SEQ ID 73 | Tag 26186 |
| SEQ ID 74 | Tag 26187 |
| SEQ ID 75 | Tag 26188 |
| SEQ ID 76 | Tag 26189 |
| SEQ ID 77 | Tag 26190 |
| SEQ ID 78 | Tag 26191 |
| SEQ ID 79 | Tag 26192 |
| SEQ ID 80 | Tag 26193 |
| SEQ ID 81 | Tag 26194 |
| SEQ ID 82 | Tag 26195 |
| SEQ ID 83 | Tag 26196 |
| SEQ ID 84 | Tag 26197 |
| SEQ ID 85 | Plasmid 18158 |
| SEQ ID 86 | Plasmid 18162 |
| SEQ ID 87 | Plasmid 18165 |
| SEQ ID 88 | Plasmid 18598 |
| SEQ ID 89 | Plasmid 18600 |
| SEQ ID 90 | Plasmid 18597 |
| SEQ ID 91 | Plasmid 18602 |
| SEQ ID 92 | Plasmid 19631 |
| SEQ ID 93 | Plasmid 19642 |
| SEQ ID 94 | Plasmid 19711 |
| SEQ ID 95 | Plasmid 19633 |
| SEQ ID 96 | Plasmid 19823 |
| SEQ ID 97 | Plasmid 20465 |
| SEQ ID 98 | Plasmid 20469 |

Example 1

Design of Peptide Tag Sets

A set of unique peptide sequences were designed based on the known LC-MS standards angiotensin I, angiotensin II, leu enkephalin, vasoactive intestinal peptide, glu-fibrinogen, bradykinin and ACTH (Table 3).

TABLE 3

Unique peptide sequences derived from known LC-MS standards.

| Source standard | Unique peptide sequence | Mono-isotopic mass | M/Z of +2 | M/Z of +3 | Favored charge state |
|---|---|---|---|---|---|
| angiotensin I | DRVYIHPFHL | 1296.68 | 648.84 | 432.89 | +3 > +2 |
| angiotensin II | DRVYIHPF | 1045.54 | 523.27 | 349.18 | +2 |
| leu enkephalin | YGGFL | 556.27 | 278.64 | 186.09 | +2 |

TABLE 3-continued

Unique peptide sequences derived from known LC-MS standards.

| Source standard | Unique peptide sequence | Mono-isotopic mass | M/Z of +2 | M/Z of +3 | Favored charge state |
|---|---|---|---|---|---|
| vasoactive intestinal peptide | HSDAVFTDNTR | 1425.46 | 713.23 | 475.82 | +3 > +2 |
| glu-fibrinogen | EGVNDNEEGFFSAR | 1569.65 | 785.33 | 523.88 | +2 |
| bradykinin | RPPGFSP | 756.39 | 378.70 | 252.80 | +2 |
| ACTH | RPVKVYPNGAEDESAEAFPLEF | 2464.19 | 1232.60 | 822.06 | +2, +3, +4 |

For each unique peptide sequence derived from a different LC-MS standard, the peptide sequence, monoisotopic mass, mass to charge ratio (M/Z) for the +2 and +3 charge states and the favored charge state are listed.

Peptide tags were designed by combining the unique peptide sequences listed in Table 3 with the cleavage recognition site of GE's PreScission protease so that the tags would be separable from the associated protein of interest. Tags were designed to be positioned on either the N- or C-terminus of the protein of interest (Table 4).

TABLE 4

Intact peptide tags sequences.

| Name | Complete peptide tag sequence | Position |
|---|---|---|
| 17696 | MDRVYIHPFHLLEVLFQ↓GP | N-terminus |
| 17697 | MDRVYIHPFLEVLFQ↓GP | N-terminus |
| 17698 | MYGGFLLEVLFQ↓GP | N-terminus |
| 17699 | MHSDAVFTDNTRLEVLFQ↓GP | N-terminus |
| 17700 | MEGVNDNEEGFFSARLEVLFQ↓GP | N-terminus |
| 17701 | MRPPGFSPLEVLFQ↓GP | N-terminus |
| 17702 | MRPVKVYPNGAEDESAEAFPLEFLEVLFQ↓GP | N-terminus |
| 17689 | LEVLFQ↓GPDRVYIHPFHL | C-terminus |
| 17690 | LEVLFQ↓GPDRVYIHPF | C-terminus |
| 17691 | LEVLFQ↓GPYGGFL | C-terminus |
| 17692 | LEVLFQ↓GPHSDAVFTDNTR | C-terminus |
| 17693 | LEVLFQ↓GPEGVNDNEEGFFSAR | C-terminus |
| 17694 | LEVLFQ↓GPRPPGFSP | C-terminus |
| 17695 | LEVLFQ↓GPRPVKVYPNGAEDESAEAFPLEF | C-terminus |

For convenience, each peptide tag is referenced by a unique identifier (Name) and each intact peptide tag sequence design is shown. For each peptide tag, the protease cleavage site is indicated by ↓. Peptide tags were designed to be positioned either on the N- or C-terminus of the protein of interest as indicated.

Cleaved peptide tag sequences were analyzed for their monoisotopic mass, mass to charge ratio in different charge states. Additionally, cleaved sequences were analyzed using the STEPP software from Pacific Northwest national Laboratory which uses support vector machine techniques to compute an observability score for MS analysis. The STEPP software can compute both a probability score and an SVM score for analyzed sequences. Peptides with larger (more positive) SVM scores are more likely to be detectable via MS. Results for a set of peptide tags are shown (Error! Reference source not found.).

TABLE 5

Computational analysis of cleaved peptide tags sequences.

| Name | Mono-isotopic mass | M/Z of +2 | M/Z of +3 | M/Z of +4 | Probability | SVM score |
|---|---|---|---|---|---|---|
| 17696 | 3151.51 | 1576.26 | 1051.17 | 788.63 | 0.204 | -0.259 |
| 17697 | 2901.37 | 1451.19 | 967.79 | 726.09 | 0.271 | -0.199 |
| 17698 | 2411.11 | 1206.06 | 804.37 | 603.53 | 0.832 | 0.249 |
| 17699 | 3117.41 | 1559.21 | 1039.80 | 780.10 | 0.444 | -0.071 |
| 17700 | 3425.51 | 1713.26 | 1142.50 | 857.13 | 0.560 | 0.009 |
| 17701 | 2612.23 | 1306.62 | 871.41 | 653.81 | 0.426 | -0.083 |
| 17702 | 4320.03 | 2160.52 | 1440.68 | 1080.76 | 0.241 | -0.224 |
| 17689 | 2445.14 | 1223.07 | 815.71 | 612.04 | 0.416 | -0.090 |
| 17690 | 2195.00 | 1098.00 | 732.33 | 549.50 | 0.473 | -0.051 |
| 17691 | 1704.74 | 852.87 | 568.91 | 426.94 | 0.874 | 0.309 |
| 17692 | 2411.04 | 1206.02 | 804.35 | 603.51 | 0.633 | 0.063 |
| 17693 | 2719.14 | 1360.07 | 907.05 | 680.54 | 0.745 | 0.155 |
| 17694 | 1905.86 | 953.43 | 635.95 | 477.22 | 0.567 | 0.015 |
| 17695 | 3613.66 | 1807.33 | 1205.22 | 904.17 | 0.466 | -0.055 |

For each peptide tag (referenced by a unique Name), the cleaved peptide sequence was analyzed for its monoisotopic mass, mass to charge (M/Z) ratio for the +2, +3 and +4 charge states. The probability and SVM scores generated by the STEPP software are also shown.

To facilitate enrichment and purification of peptide tags from their parent proteins and the background proteome via affinity purification, an alternative set of peptide tags were designed that include an affinity tag sequence (Table 6). Candidate affinity tags evaluated included FLAG tag, Myc tag, HA tag, and Strep tag. As described above, peptide tags were designed to be positioned either on the N- or C-terminus and cleaved peptide sequences were analyzed computationally both for their expected mass to charge ratio in different charge states and for their observability via MS analysis using the STEPP software. In general, those peptide tag designs that include either a Myc or HA affinity tag have are high scoring than those that include a FLAG or Strep tag and thus are preferable peptide tag designs.

TABLE 6

Intact peptide tags sequences that include an affinity tag.

| Name | Complete peptide tag sequence | Position | Probability | SVM score |
|---|---|---|---|---|
| | Includes FLAG tag | | | |
| | MDYKDDDDKDRVYIHPFHLLEVLGQ↓GP | N- | 0.204 | -0.259 |
| | MDYKDDDDKDRVYIHPFLEVLGQ↓GP | N- | 0.271 | -0.199 |
| | MDYKDDDDKYGGFLLEVLGQ↓GP | N- | 0.832 | 0.249 |
| | MDYKDDDDKHSDAVFTDNTRLEVLGQ↓GP | N- | 0.444 | -0.071 |
| | MDYKDDDDKEGVNDNEEGFFSARLEVLGQ↓GP | N- | 0.560 | 0.009 |
| | MDYKDDDDKRPPGFSPLEVLGQ↓GP | N- | 0.426 | -0.083 |
| | MDYKDDDDKRPVKVYPNGAEDESAEAFPLEFLEVLGQ↓GP | N- | 0.241 | -0.224 |
| | LEVLGQ↓GPDRVYIHPFHLDYKDDDDK | C- | 0.416 | -0.090 |
| | LEVLGQ↓GPDRVYIHPFDYKDDDDK | C- | 0.473 | -0.051 |
| | LEVLGQ↓GPYGGFLDYKDDDDK | C- | 0.874 | 0.309 |
| | LEVLGQ↓GPHSDAVFTDNTRDYKDDDDK | C- | 0.633 | 0.063 |
| | LEVLGQ↓GPEGVNDNEEGFFSARDYKDDDDK | C- | 0.745 | 0.155 |
| | LEVLGQ↓GPRPPGFSPDYKDDDDK | C- | 0.567 | 0.015 |
| | LEVLGQ↓GPRPVKVYPNGAEDESAEAFPLEFDYKDDDDK | C- | 0.466 | -0.055 |
| | Includes Myc tag | | | |
| 17710 | MEQKLISEEDLDRVYIHPFHLLEVLGQ↓GP | N- | 0.301 | -0.174 |
| 17711 | MEQKLISEEDLDRVYIHPFLEVLGQ↓GP | N- | 0.434 | -0.077 |
| 17712 | MEQKLISEEDLYGGFLLEVLGQ↓GP | N- | 0.970 | 0.573 |
| 17713 | MEQKLISEEDLHSDAVFTDNTRLEVLGQ↓GP | N- | 0.617 | 0.050 |
| 17714 | MEQKLISEEDLEGVNDNEEGFFSARLEVLGQ↓GP | N- | 0.712 | 0.126 |
| 17715 | MEQKLISEEDLRPPGFSPLEVLGQ↓GP | N- | 0.762 | 0.171 |
| 17716 | MEQKLISEEDLRPVKVYPNGAEDESAEAFPLEFLEVLGQ↓GP | N- | 0.319 | -0.161 |
| 17703 | LEVLGQ↓GPDRVYIHPFHLEQKLISEEDL | C- | 0.712 | 0.126 |
| 17704 | LEVLGQ↓GPDRVYIHPFEQKLISEEDL | C- | 0.866 | 0.297 |
| 17705 | LEVLGQ↓GPYGGFLEQKLISEEDL | C- | 1.000 | 1.124 |
| 17706 | LEVLGQ↓GPHSDAVFTDNTREQKLISEEDL | C- | 0.909 | 0.374 |
| 17707 | LEVLGQ↓GPEGVNDNEEGFFSAREQKLISEEDL | C- | 0.911 | 0.379 |
| 17708 | LEVLGQ↓GPRPPGFSPEQKLISEEDL | C- | 0.931 | 0.427 |
| 17709 | LEVLGQ↓GPRPVKVYPNGAEDESAEAFPLEFEQKLISEEDL | C- | 0.599 | 0.038 |
| | Includes HA tag | | | |
| 17724 | MYPYDVPDYADRVYIHPFHLLEVLGQ↓GP | N- | 0.758 | 0.168 |
| 17725 | MYPYDVPDYADRVYIHPFLEVLGQ↓GP | N- | 0.848 | 0.270 |
| 17726 | MYPYDVPDYAYGGFLLEVLGQ↓GP | N- | 0.984 | 0.680 |
| 17727 | MYPYDVPDYAHSDAVFTDNTRLEVLGQ↓GP | N- | 0.935 | 0.438 |
| 17728 | MYPYDVPDYAEGVNDNEEGFFSARLEVLGQ↓GP | N- | 0.938 | 0.445 |
| 17729 | MYPYDVPDYARPPGFSPLEVLGQ↓GP | N- | 0.946 | 0.471 |
| 17730 | MYPYDVPDYARPVKVYPNGAEDESAEAFPLEFLEVLGQ↓GP | N- | 0.625 | 0.056 |
| 17717 | LEVLGQ↓GPDRVYIHPFHLYPYDVPDYA | C- | 0.925 | 0.410 |
| 17718 | LEVLGQ↓GPDRVYIHPFYPYDVPDYA | C- | 0.954 | 0.500 |
| 17719 | LEVLGQ↓GPYGGFLYPYDVPDYA | C- | 0.996 | 0.877 |
| 17720 | LEVLGQ↓GPHSDAVFTDNTRYPYDVPDYA | C- | 0.990 | 0.750 |
| 17721 | LEVLGQ↓GPEGVNDNEEGFFSARYPYDVPDYA | C- | 0.990 | 0.749 |
| 17722 | LEVLGQ↓GPRPPGFSPYPYDVPDYA | C- | 0.975 | 0.609 |
| 17723 | LEVLGQ↓GPRPVKVYPNGAEDESAEAFPLEFYPYDVPDYA | C- | 0.854 | 0.279 |
| | Includes Strep tag | | | |
| | MAWRHPQFGGDRVYIHPFHLLEVLGQ↓GP | N- | 0.022 | -0.631 |
| | MAWRHPQFGGDRVYIHPFLEVLGQ↓GP | N- | 0.020 | -0.640 |
| | MAWRHPQFGGYGGFLLEVLGQ↓GP | N- | 0.463 | -0.057 |
| | MAWRHPQFGGHSDAVFTDNTRLEVLGQ↓GP | N- | 0.026 | -0.604 |
| | MAWRHPQFGGEGVNDNEEGFFSARLEVLGQ↓GP | N- | 0.083 | -0.424 |
| | MAWRHPQFGGRPPGFSPLEVLGQ↓GP | N- | 0.092 | -0.406 |
| | MAWRHPQFGGRPVKVYPNGAEDESAEAFPLEFLEVLGQ↓GP | N- | 0.018 | -0.660 |
| | LEVLGQ↓GPDRVYIHPFHLAWRHPQFGG | C- | 0.090 | -0.410 |
| | LEVLGQ↓GPDRVYIHPFAWRHPQFGG | C- | 0.102 | -0.389 |

TABLE 6-continued

Intact peptide tags sequences that include an affinity tag.

| Name | Complete peptide tag sequence | Position | Probability | SVM score |
|------|-------------------------------|----------|-------------|-----------|
| | LEVLGQ↓GPYGGFLAWRHPQFGG | C- | 0.774 | 0.183 |
| | LEVLGQ↓GPHSDAVFTDNTRAWRHPQFGG | C- | 0.163 | -0.304 |
| | LEVLGQ↓GPEGVNDNEEGFFSARAWRHPQFGG | C- | 0.307 | -0.170 |
| | LEVLGQ↓GPRPPGFSPAWRHPQFGG | C- | 0.293 | -0.180 |
| | LEVLGQ↓GPRPVKVYPNGAEDESAEAFPLEFAWRHPQFGG | C- | 0.061 | -0.473 |

As an alternative design strategy, a set of intact peptide tag sequence designs that include an affinity tag to facilitate enrichment/purification of the tags from the background proteome are shown. For each peptide tag, the protease cleavage site is indicated by ↓. Peptide tags were designed to be positioned either on the N- or C-terminus of the protein of interest as indicated. Computed probability and SVM scores by the STEPP software for each cleaved peptide sequence are listed. Since peptide tag designs that include a Myc or HA tag showed generally higher scores than tags that included a FLAG or Strep tag, only those tags were assigned unique Names.

Example 2

Construction of a Set of Tagged Proteins

Figure 7:
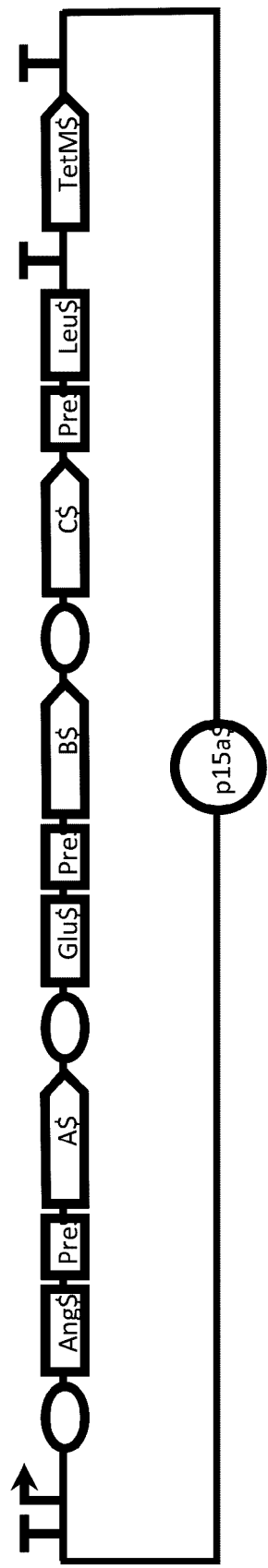
FIG. 7 illustrates a schematic of an exemplary plasmid design for testing utility of peptide tags for detection of the associated protein of interest according to one embodiment of the invention. Each icon represents a different genetic element as follows: right line arrow: promoter; oval: ribosome binding site; rectangles: peptide tags; T: terminator; circle: plasmid replication origin. Abbreviations are as follows: Ang: genetic element encoding peptide sequence derived from angiotensin I peptide standard; Pre: genetic element encoding protease recognition site from GE's PreScission protease; A: protein coding gene of interest A; Glu: genetic element encoding peptide sequence derived from glu-fibrinogen standard; B: protein coding gene of interest B; C: protein coding gene of interest C: Leu, genetic element encoding peptide sequence derived from leu enkephalin standard; TetM: tetracycline resistance marker.
Figure 8B:
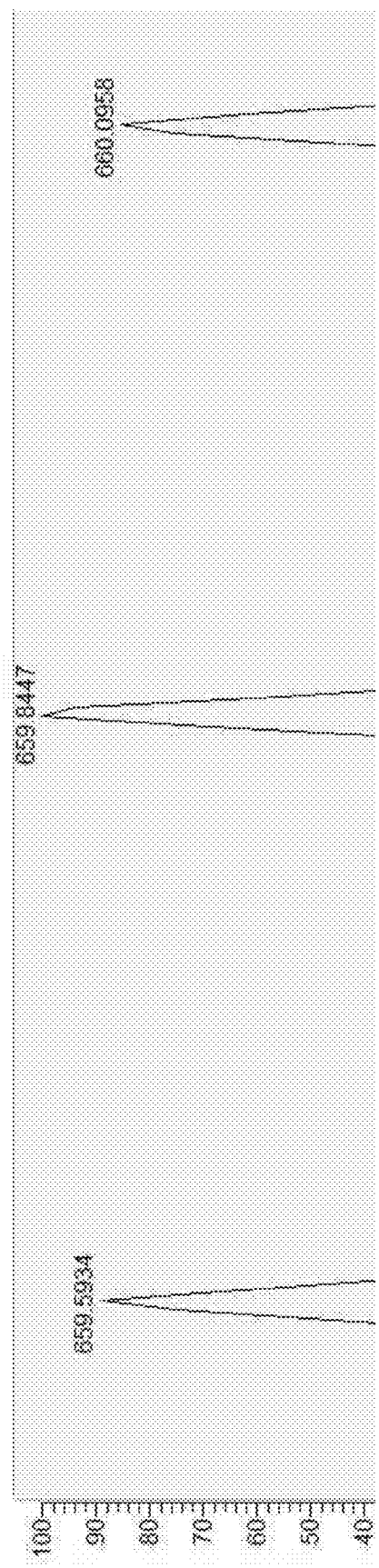
FIG. 8 depicts experimentally measured MS spectra of 5 different peptide tags isolated from E. coli cultures according to one embodiment of the invention. For each spectra, the y axis denotes relative abundance and the x axis denotes the mass to charge ratio (m/z). Multiple tags are shown including peptide tag 17710 (+4 charge state) [A], peptide tag 17703 (+4 charge state) [B], peptide tag 17696 (+3 charge state) [C], peptide tag 17700 (+3 charge state) [D] and peptide tag 17691 (+2 charge state) [E]. Peptide tag identifiers correspond to Table 4 and Table 6.
Figure 8C:
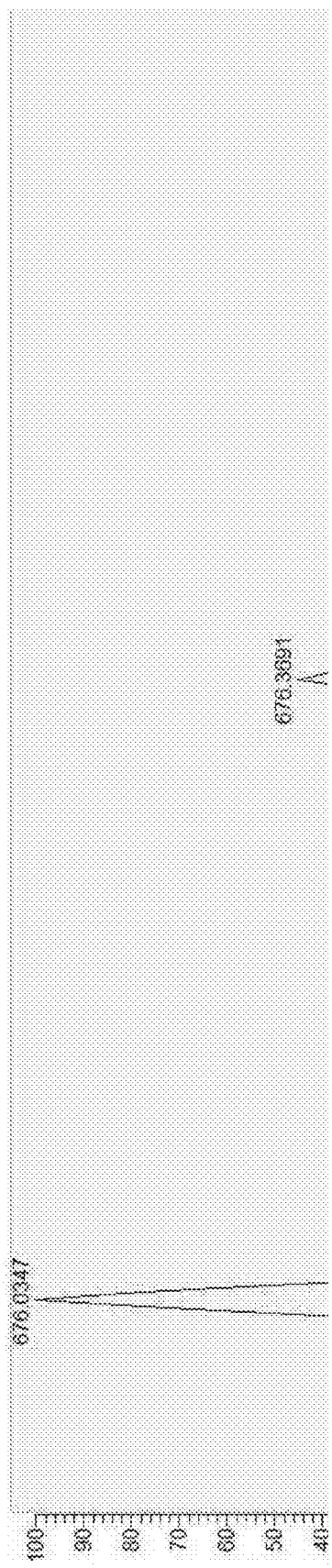
Figure 8D:
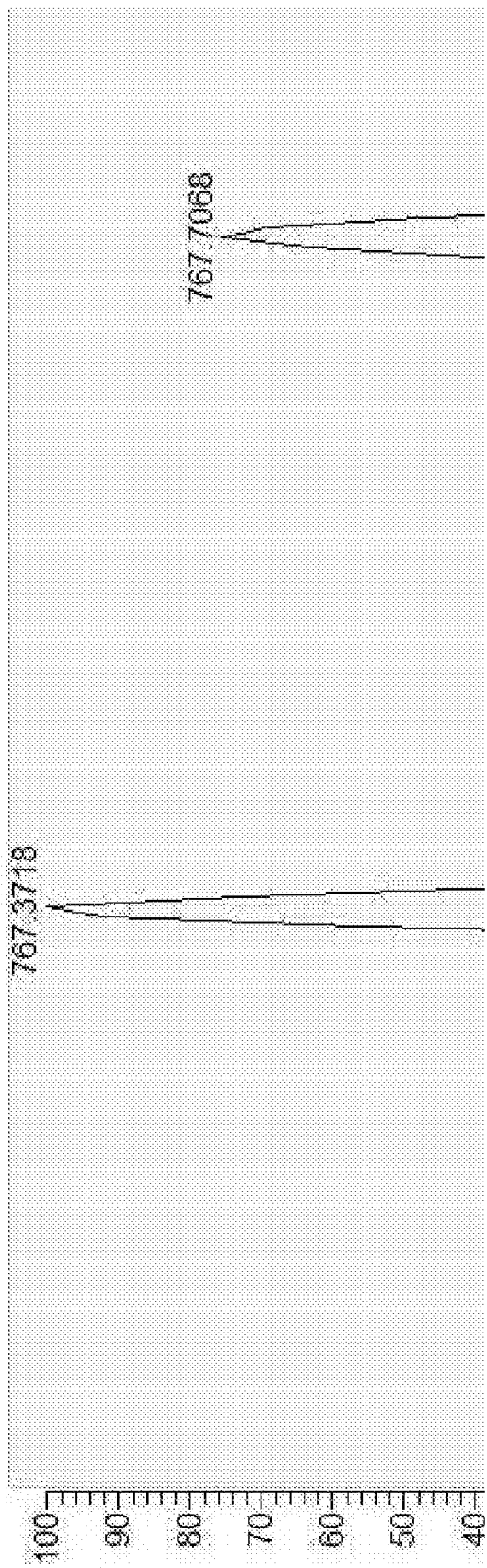
Figure 8E:
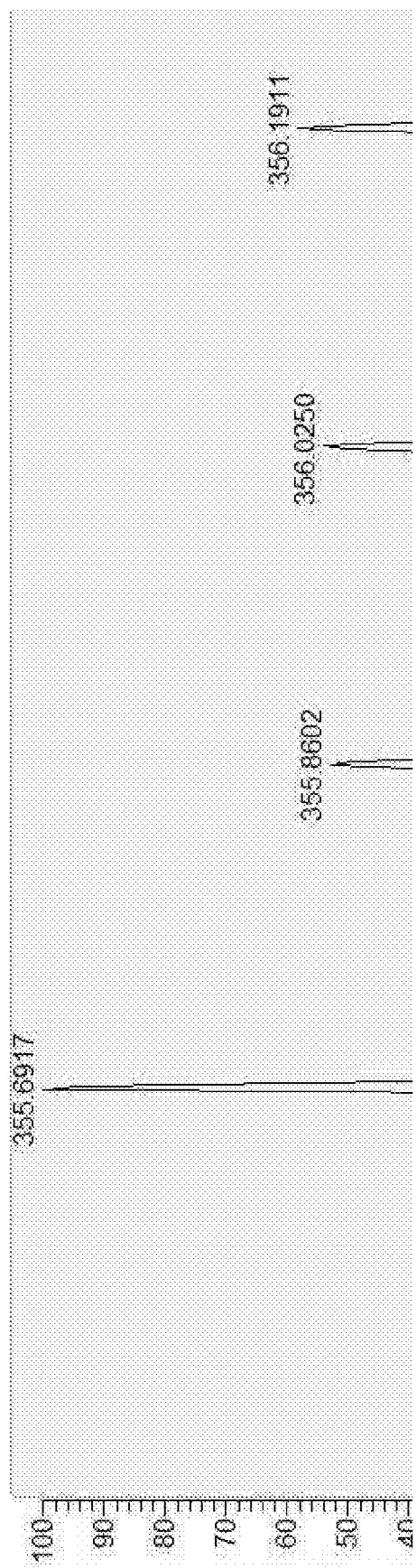

Plasmids comprising a medium copy number replication origin, tetracycline resistance marker and between 1-3 codon-optimized protein encoding genes under the control of a constitutive promoter were constructed using DNA assembly methods described in WO/2010/070295. A schematic of a three gene plasmid is shown (FIG. 7). Each gene of interest included either an N-terminal or C-terminal tag from the peptide tag set described in Example 1. DNA sequences encoding each of the peptide tags are listed (SEQ ID NOs 43-84). The resulting plasmids (SEQ ID NOs 85-98) were transformed into E. coli using standard plasmid transformation techniques. As a negative control, a protein expression plasmid expressing an untagged protein was also constructed.

Cultures propagating each of the plasmids were inoculated from glycerol stocks and grown overnight in a 24-well plate with fresh LB media supplemented with 10-15 µg/ml tetracycline at 37° C. Experimental samples for LC-MS analysis were then prepared using methods described in Example 4 or Example 5, as appropriate.

Example 3

Transposon-Mediated Insertion of Tagged Proteins into M. florum

Transposon constructs were isolated from containing plasmids (SEQ ID NOs 85-98) either by PCR with 5' phosphorylated primer 4005 (5' ctgtctcttatacacatct 3'), or by cutting at the PvuII restriction enzyme site, to form a 5' phosphorylated linear double stranded transposon fragment. As a negative control, a transposon construct derived from a protein expression plasmid expressing an untagged protein was also constructed. All transposon fragments were flanked on both ends by inverted repeats of the 19 bp transposon end sequence. DNA was adjusted to 100 ng/µl concentration in TE.

Transposomes were formed by incubating 2 µl of transposon DNA with 2 µl of glycerol and 4 µl of Tn5 transposase (Epicentre) for 1 hour at 37° C., followed by incubation at 4° C. overnight and freezing at -80° C. indefinitely.

M. florum cells were grown to mid exponential phase (slight color change in phenol red medium), pelleted at 8000×g for 30 minutes, resuspended in EP buffer (272 mM sucrose, 8 mM HEPES, pH 7.5). After similar centrifugation, the pellet is resuspended in 1/10th volume of EP buffer and used or frozen at -80° C. indefinitely.

Cells were transformed by mixing 2 µl of transposomes with 50 µl of prepared cells, placing them in a 1 mm electroporation cuvette, and subjecting them to a pulse of 1.2 kv, 200 ohms, 50 ufd, for a resulting time constant of 6.2 ms. Following electroporation, the cells were resuspended in 1 ml of mycoplasma medium and allowed to grow without selection for 1.5 hours (no shaking) Following incubation, the cells were either plated on mycoplasma medium containing 15 µg/ml tetracycline, or 1 µl of a 15 mg/ml solution was added to the 1 ml culture. Plates or liquid samples were grown for 1 day. Colonies were picked from plates into liquid culture for outgrowth. Liquid cultures exhibiting growth were plated on Tet containing plates to isolate single colonies, followed by outgrowth.

Liquid cultures were used to prepare genomic DNA using the Zymo gDNA kit, following the manufacturer's instructions. Resulting DNA was sequenced directly on an ABI 3730 using primer 5075 (5' ataccttgccgcatatttattaactcc 3'), matching a location on the transposon insert. The sequence read was used to locate the transposon insertion site by locating the end of the transposon and matching the remaining sequence with the M. florum genome (Genbank accession NC_006055) using BLAST. A list of successful transposon insertions into M. florum is provided (Table 7).

TABLE 7

Transposon insertion locations.

| Transposon source (plasmid name) | Insertion location | Orientation |
|---|---|---|
| 18600 | 71569 | reverse |
| 18602 | 91088 | forward |
| 18158 | 515413 | reverse |
| 19642 | 155477 | forward |
| 18165 | 379025 | forward |

For each successfully inserted transposon construct, the source plasmid from which the transposon construct was derived, genomic insertion location and transposon orientation in the M. florum genome are listed.

Example 4

Size-Based Fractionation of Peptide Tags from Cell Lysates

M. florum or E. coli cultures expressing tagged proteins were pelleted at 4° C. The pellet was broken up and washed in either ice cold PBS (*E. coli*) or EP buffer (8 mM HEPES, pH 7.5, 272 mM sucrose, for *M. florum*) via pipetting and vortexing. Cells were re-pelleted and lysed under fully denaturing conditions in 1 mL of 8 M urea on ice for 15 minutes with intermittent vortexing. Lysates contained 1-2 mg of total protein. Lysates were then reduced with 10 mM DTT at 56° C. for one hour.

To prepare for specific cleavage of reporter tags, lysates were size fractionated on a spin column to desalt and eliminate excess DTT. To retain intact tagged proteins and additionally eliminate some natively occurring peptides, a membrane insert with a size cutoff of 10,000 Da was used (Amicon). Lysates were spun through the membrane at 7,500×g for 25 minutes at 4° C. The retained, concentration fraction was resuspended in cleavage buffer (20 mM Tris HCl buffer, pH 7.6, 30 mM NaCl, 1 mM DTT) to a final volume of 1 mL. 24 µg of HRV3C protease (AG Scientific) was added to each sample, and samples were incubated for 16 hours at 4° C. on a rotator.

Digested samples were then size fractionated to collect cleaved reporter tags. Digests were spun on a 10,000 Da cutoff membrane at 7,500×g for 25 minutes at 4° C. Flow-through was collected and loaded onto a Sep Pak C18 Plus cartridge for desalting (Waters). Samples were washed with 0.1% acetic acid and then eluted with 90% acetonitrile in 0.1% acetic acid. Organic solvent was eliminated by concentrating samples on either a speed vacuum centrifuge or with a nitrogen drier. Concentrated samples were then resuspended in 0.1% acetic acid at a final volume of 150 µL. Samples were then analyzed by MS as described in Example 6.

Example 5

Immunoprecipitation-Based Enrichment of Peptide Tags from Cell Lysates

*M. florum* or *E. coli* cultures expressing tagged proteins were pelleted at 4° C. The pellet was broken up and washed in either ice cold PBS (*E. coli*) or EP buffer (8 mM HEPES, pH 7.5, 272 mM sucrose, for *M. florum*) via pipetting and vortexing. Cells were re-pelleted and lysed under fully denaturing conditions in 1 mL of 8 M urea on ice for 15 minutes with intermittent vortexing. Lysates contained 1-2 mg of total protein. Lysates were then reduced with 10 mM DTT at 56° C. for one hour.

To prepare for specific cleavage of reporter tags, lysates were size fractionated on a spin column to desalt and eliminate excess DTT. To retain intact tagged proteins and additionally eliminate some natively occurring peptides, a membrane insert with a size cutoff of 10,000 Da was used (Amicon). Lysates were spun through the membrane at 7,500×g for 25 minutes at 4° C. The retained, concentration fraction was resuspended in cleavage buffer (20 mM Tris HCl buffer, pH 7.6, 30 mM NaCl, 1 mM DTT) to a final volume of 1 mL. 24 µg of HRV3C protease (AG Scientific) was added to each sample, and samples were incubated for 16 hours at 4° C. on a rotator.

During tag cleavage, affinity tag specific antibodies were conjugated to either Protein A or Protein G preblocked agarose beads (Millipore). For instance, 20 µg each of anti-c-Myc monoclonal antibodies (Cell Signaling Technologies and Abgent) were incubated with 60 µL of Protein A agarose bead slurry for 12 hours in IP buffer (0.3% NP-40, 100 mM Tris HCl, pH 7.4). Beads were then washed in IP buffer and pelleted for sample addition. Digested samples were brought up to 1.5 mL total volume in IP buffer and added to the conjugated beads. Samples were incubated with IP beads for 8 hours at 4° C. on a rotator. Beads were then pelleted and washed four times in 400 µL of rinse buffer (100 mM Tris HCL, pH 7.4) at 4° C. on a rotator. Captured peptides were then eluted by incubating the beads for 30 minutes at room temp in 70 µL of elution buffer (100 mM glycine, pH 2.5). Beads were pelleted, and the eluate was brought to 0.1% acetic acid. Samples were then analyzed by MS as described in Example 6.

Example 6

MS Analysis of Peptide Tags from Cell Lysates

Figure 9:
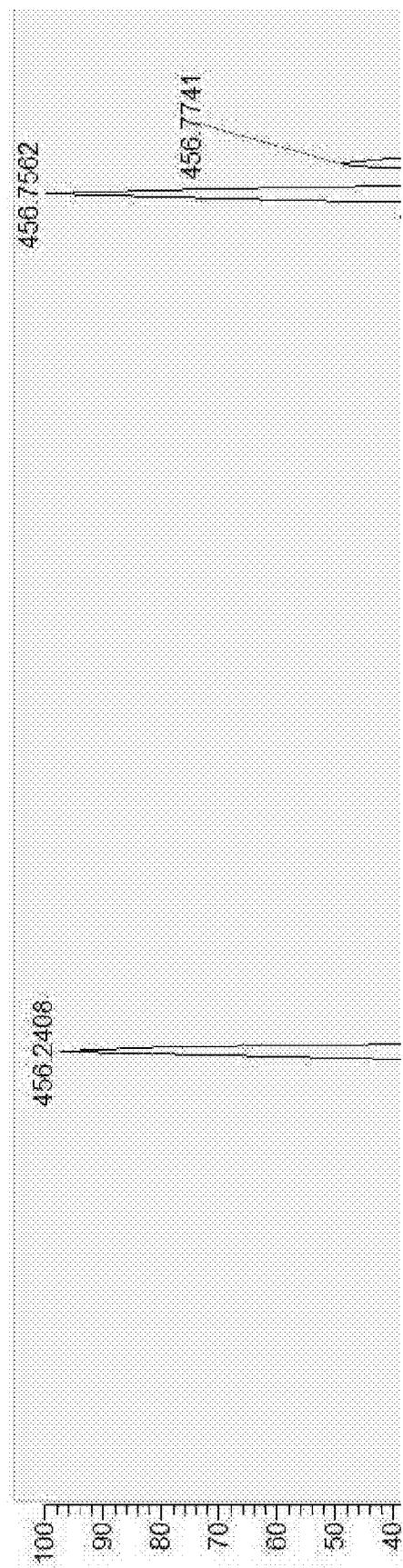
FIG. 9 depicts experimentally measured MS spectra of peptide tag 17694 (+2 charge state) isolated from an M. florum culture. Peptide tag identifier corresponds to Table 4.

10 µl of each experimental sample prepared as described in either Example 4 or Example 5 were autosampled using an Accela Open AS system with a refrigerated sample stack, and loaded and washed on a 200 µM ID guard column containing 3 cm of 5 um Proteoprep C18 resin (New Objective). After washing, the guard column was brought inline with an analytical column with 10 cm of 5 um Proteoprep C18 resin and an integrated 15 µM Picofrit nano-ESI tip (New Objective). Electrospray was established at 2000 volts to introduce peptide for full scan detection and MS/MS fragmentation on a hybrid quadrupole Orbitrap mass spectrometer (Q-Exactive, Thermo Scientific). Peptides were sequentially eluted using a binary reverse phase HPLC gradient, with a weak solvent of 0.2 M acetic acid in ultrapure water, and a strong solvent of 80% acetonitrile, 0.2 M acetic acid in ultrapure water. Total gradients between 10 and 40 minutes were successfully tested. Column resolving power and sensitivity was tested using the standards angiotensin I and vasoactive intestinal peptide prior to sample loading and elution. 300 ms full scans were performed at resolution 70,000 to obtain high-resolution, accurate mass scans of the intact reporter tags precursors, which were tracked via extracted ion chromatograms and targeted for MS/MS fragmentation via nitrogen collision induced (HCD) fragmentation to confirm peptide sequences. MS spectra for a selection of experimentally detected peptide tags from *E. coli* cell cultures expressing tagged proteins are shown (FIG. 8). MS spectra for an experimentally detected peptide tag from an *M. florum* culture expressing a tagged protein is shown (FIG. 9).

Figure 10:
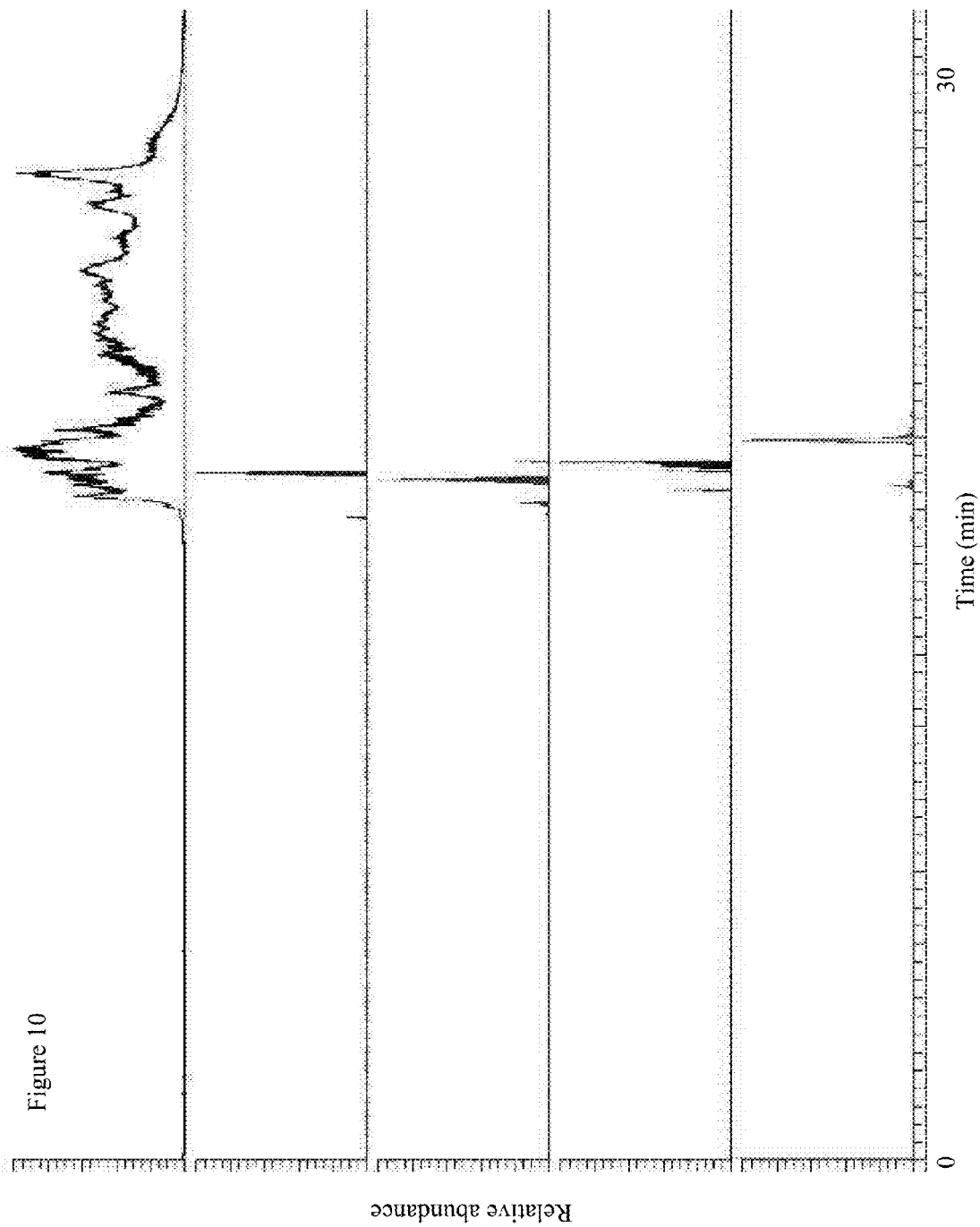
FIG. 10 depicts the total ion chromatogram (TIC) and extracted ion chromatogram (XIC) for four peptide reporter tags detected in the same run are shown, demonstrating multiplexed detection of tags from the same lysate. Proteins were digested with GE's Prescission protease, and then subjected to size fractionation (10,000 MW cutoff) and desalting before detection via reverse phase nano-ESI LC-MS on a high resolution, accurate mass mass spectrometer (Q-Exactive, Thermo Scientific). After the TIC at top, XIC traces are shown from top to bottom tracking the exact masses of the C-terminal peptide tag 17692 (+3 charge state, 472.8883 m/z), N-terminal peptide tag 17696 (+4, 540.5238 m/z), N-terminal peptide tag 17700 (+4, 431.9618 m/z), and N-terminal peptide tag 17700 with an unprocessed methionine (+4, 464.9999). Retention times denoting the sequential elution of each tag during the LC gradient are denoted at each XIC peak.
Figure 11:
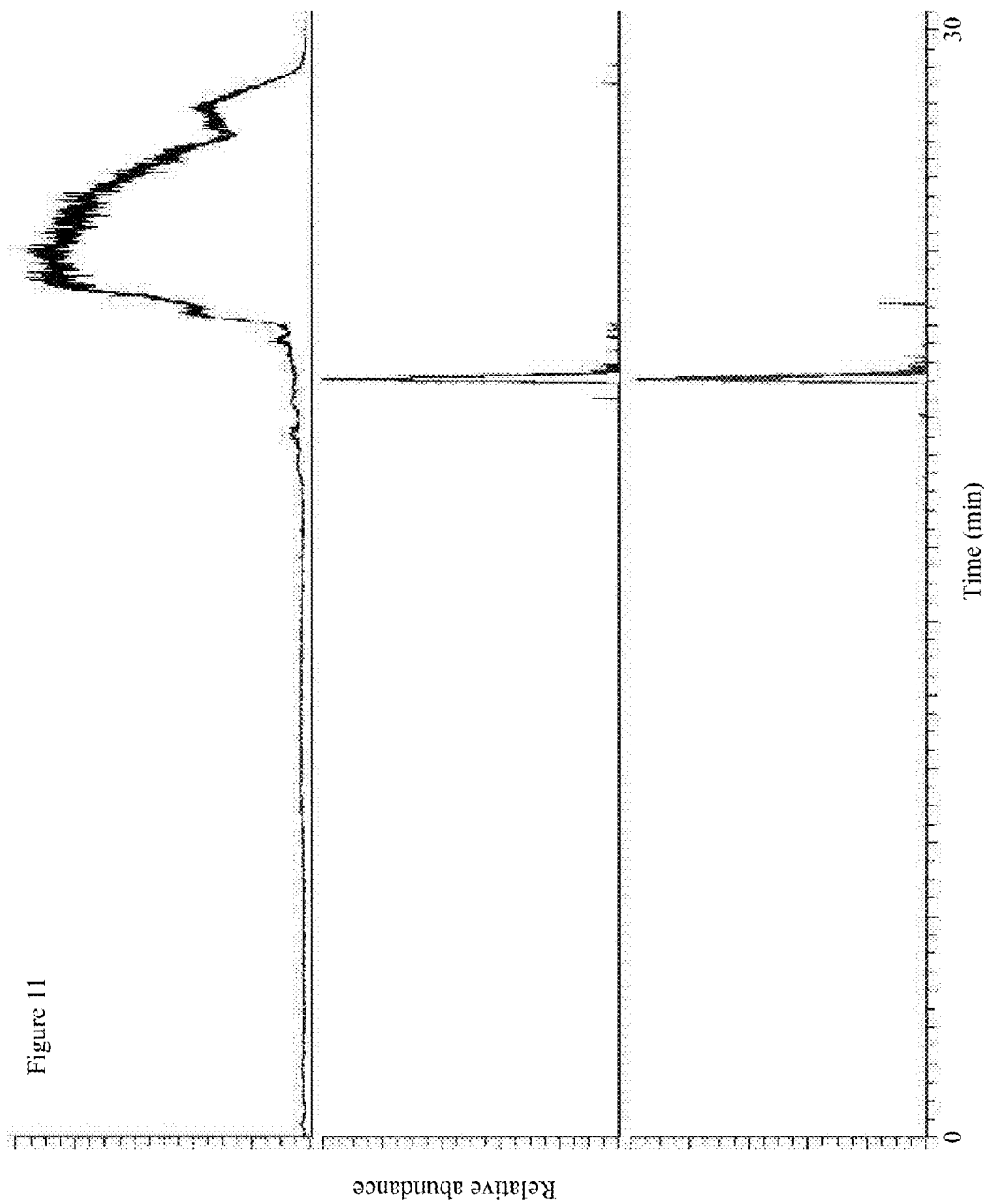
FIG. 11 depicts the total ion chromatogram (TIC) and extracted ion chromatogram (XIC) of two charge states of the C-terminal peptide tag 17703, which includes a c-Myc affinity tag. Proteins were digested with the Precission protease, and then purified via immunoprecipitation with an anti-c-Myc antibody on Protein A agarose beads. Captured peptide tags were washed and eluted to an LC precolumn, washed and then detected via reverse phase LC-MS. XIC traces of the exact masses of the +4 (659.5933 m/z) and +5 (527.8761 m/z) charge states show coelution, thereby providing additional confirmation of tag identity and the opportunity for selection of the charge state in the clean scan region for quantitation.

Using the methods described herein, it is possible to detect multiple peptide tags, each with detectable charge state with a unique mass to charge ratio, in a single MS scan (FIG. 10). As further evidence that peptide tags serve as unique, consistent identifiers of the parent protein, two different charge states of peptide tag 17703 are shown to co-elute during liquid chromatography (FIG. 11).

Other Embodiments

The examples have focused on redesigning *E. coli* and *M. florum* to be easier to measure. *E. coli* is a well-understood, industrial host that is commonly used in genetic engineering and molecular biology. *M. florum* offers an attractive chassis for synthetic biology research efforts because of its small number of gene components, its fast growth, its safety and its genetic tractability. Nevertheless, the key concept of facilitating routine quantitative proteome analysis by coupling introduction of genetically-encoded peptide tags onto every protein in the genome to hardware design is extensible to other, more complex organisms such as other prokaryotic or eukaryotic single cell organisms such as *S. cerevisiae*, plant cells or cell lines, mammalian cells or cell lines, or insect cells or cell lines.

Aspects of the present invention can also be included in an integrated system or kit for cell state quantification. For example, a kit including the engineered cell as discussed herein and use instructions thereof can be provided. A kit including a set of isotopically labeled synthetic peptides at defined concentrations corresponding to the library of peptide tags as discussed herein for use as quantitative reference standards and use instructions thereof can also be provided. As a second example, an integrated system including the engineered cell as discussed herein and a mass spectrometry instrument and associated analysis software customized for tag detection, identification and quantitation and use instructions thereof can also be provided. As a third example, a kit including oligonucleotides encoding each of the designed peptide tags can be provided.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EQUIVALENTS

The present invention provides among other things novel methods and systems for synthetic biology. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

REFERENCES CITED

Allam A B, Reyes L, Assad-Garcia N, Glass J I, Brown M B. Targeted homologous recombination in *Mycoplasma mycoides* subsp. *capri* is enhanced by inclusion of heterologous recA. Appl Environ Microbiol. 2010 Aug. 27.

Bennett B D, Yuan J, Kimball E H, Rabinowitz J D. Absolute quantitation of intracellular metabolite concentrations by an isotope ratio-based approach. Nat. Protoc. 2008; 3(8): 1299-311.

Bondarenko, P. V. and Chelius, D., (2002). Quantitative profiling of proteins in complex mixtures using liquid chromatography and mass spectrometry. J Proteome Res 1, 317-323.

Chan L Y, Kosuri S, Endy D. Refactoring bacteriophage T7. Mol Syst Biol. 2005; 1:2005.0018.

Chang A, Scheer M, Grote A, Schomburg I, Schomburg D. BRENDA, AMENDA and FRENDA the enzyme information system: new content and tools in 2009. Nucleic Acids Res. 2009 January; 37 (Database issue):D588-92.

Cech N B, Enke C G. Relating electrospray ionization response to nonpolar character of small peptides. Anal Chem. 2000 Jul. 1; 72(13):2717-23.

Cech N B, Krone J R, Enke C G. Predicting electrospray response from chromatographic retention time. Anal Chem. 2001 Jan. 15; 73(2):208-13.

Cottingham, K. Overcoming ionization suppression in electrospray. Anal Chem. 2006 78, 5239.

Datta S, Costantino N, Zhou X, Court D L. Identification and analysis of recombineering functions from Gram-negative and Gram-positive bacteria and their phages. Proc Natl Acad Sci USA. 2008 Feb. 5; 105(5):1626-31.

Deutsch E W, Lam H, Aebersold R. PeptideAtlas: a resource for target selection for emerging targeted proteomics workflows. EMBO Rep. 2008 May; 9(5):429-34.

Ellis H M, Yu D, DiTizio T, Court D L. High efficiency mutagenesis, repair, and engineering of chromosomal DNA using single-stranded oligonucleotides. Proc Natl Acad Sci USA. 2001 Jun. 5; 98(12):6742-6.

Ficarro, S. B., Zhang, Y., Lu, Y., Moghimi, A. R., Askenazi, M., Hyatt, E., Smith, E. D., Boyer, L., Schlaeger, T. M., Luckey, C. J., et al. (2009). Improved electrospray ionization efficiency compensates for diminished chromatographic resolution and enables proteomics analysis of tyrosine signaling in embryonic stem cells. Anal Chem 81, 3440-3447.

Frahm J L, Bori I D, Comins D L, Hawkridge A M, Muddimana D C. Achieving augmented limits of detection for peptides with hydrophobic alkyl tags. Anal Chem. 2007 Jun. 1; 79(11):3989-95.

French C T, Lao P, Loraine A E, Matthews B T, Yu H, Dybvig K. Large-scale transposon mutagenesis of *Mycoplasma* pulmonis. Mol. Microbiol. 2008 July; 69(1):67-76.

Fusaro V A, Mani D R, Mesirov J P, Can S A. Prediction of high-responding peptides for targeted protein assays by mass spectrometry. Nat. Biotechnol. 2009 27, 190-198.

Gibbons J G, Janson E M, Hittinger C T, Johnston M, Abbot P, Rokas A. Benchmarking next-generation transcriptome sequencing for functional and evolutionary genomics. Mol Biol Evol. 2009 December; 26(12):2731-44.

Gibson D G, Benders G A, Andrews-Pfannkoch C, Denisova E A, Baden-Tillson H, Zaveri J, Stockwell T B, Brownley A, Thomas D W, Algire M A, Merryman C, Young L, Noskov V N, Glass J I, Venter J C, Hutchison C A 3rd, Smith H O. Complete chemical synthesis, assembly, and cloning of a *Mycoplasma genitalium* genome. Science. 2008 Feb. 29; 319(5867):1215-20.

Gibson D G, Benders G A, Axelrod K C, Zaveri J, Algire M A, Moodie M, Montague M G, Venter J C, Smith H O, Hutchison C A 3rd. One-step assembly in yeast of 25 overlapping DNA fragments to form a complete synthetic *Mycoplasma genitalium* genome. Proc Natl Acad Sci USA. 2008b December 23; 105(51):20404-9.

Gibson D G, Glass J I, Lartigue C, Noskov V N, Chuang R Y, Algire M A, Benders G A, Montague M G, Ma L, Moodie M M, Merryman C, Vashee S, Krishnakumar R, Assad-Garcia N, Andrews-Pfannkoch C, Denisova E A, Young L, Qi Z Q, Segall-Shapiro T H, Calvey C H, Parmar P P, Hutchison C A 3rd, Smith H O, Venter J C. Creation of a bacterial cell controlled by a chemically synthesized genome. Science. 2010 Jul. 2; 329(5987):52-6.

Glass J I, Assad-Garcia N, Alperovich N, Yooseph S, Lewis M R, Maruf M, Hutchison C A 3rd, Smith H O, Venter J C. Essential genes of a minimal bacterium. Proc Natl Acad Sci USA. 2006 Jan. 10; 103(2):425-30.

Güell M, van Noort V, Yus E, Chen W H, Leigh-Bell J, Michalodimitrakis K, Yamada T, Arumugam M, Doerks T, Kühner S, Rode M, Suyama M, Schmidt S, Gavin A C, Bork P, Serrano L. Transcriptome complexity in a genome-reduced bacterium. Science. 2009 Nov. 27; 326 (5957):1268-71.

Hackett K, Whitcomb R F. Cultivation of *Spiroplasmas* in undefined and defined media. Molecular and Diagnostic Procedures in Mycoplasmology: Volume I, Molecular Characterization. Razin S, Tully J G (eds.) San Diego, Academic Press, 1995. pp. 41-53.

Jewett M C, Forster A C. Update on designing and building minimal cells. Curr Opin Biotechnol. 2010 October; 21(5):697-703.

Kast P. pKSS—a second-generation general purpose cloning vector for efficient positive selection of recombinant clones. Gene. 1994 Jan. 28; 138 (1-2):109-14.

King R, Bonfiglio R, Fernandez-Metzler C, Miller-Stein C, Olah T. Mechanistic investigation of ionization suppression in electrospray ionization. J Am Soc Mass Spectrom. 2000 11, 942-950.

Kirkpatrick D S, Gerber S A, Gygi S P. The absolute quantification strategy: a general procedure for the quantification of proteins and post-translational modifications. Methods 2005 35, 265-273.

Kiyonami R, Schoen A, Prakash A, Peterman S, Zabrouskov V, Picotti P, Aebersold R, Huhmer A, Domon B. Increased selectivity, analytical precision, and throughput in targeted proteomics. Mol Cell Proteomics. 2010 Sep. 10.

Knight T. Idempotent Vector Design for Standard Assembly of Biobricks. DOI: 1721.1/21168.

Knight T. BBF RFC10: Draft Standard for BioBrick™ biological parts. DOI: 1721.1/45138.

Kühner S, van Noort V, Betts M J, Leo-Macias A, Batisse C, Rode M, Yamada T, Maier T, Bader S, Beltran-Alvarez P, Castaño-Diez D, Chen W H, Devos D, Güell M, Norambuena T, Racke I, Rybin V, Schmidt A, Yus E, Aebersold R, Herrmann R, Böttcher B, Frangakis A S, Russell R B, Serrano L, Bork P, Gavin A C. Proteome organization in a genome-reduced bacterium. Science. 2009 Nov. 27; 326(5957):1235-40.

Kuster B, Schirle M, Mallick P, Aebersold R. Scoring proteomes with proteotypic peptide probes. Nat Rev Mol Cell Biol. 2005 July; 6(7):577-83.

Lartigue C, Vashee S, Algire M A, Chuang R Y, Benders G A, Ma L, Noskov V N, Denisova E A, Gibson D G, Assad-Garcia N, Alperovich N, Thomas D W, Merryman C, Hutchison C A 3rd, Smith H O, Venter J C, Glass J I. Creating bacterial strains from genomes that have been cloned and engineered in yeast. Science. 2009 Sep. 25; 325(5948):1693-6.

Mallick P, Schirle M, Chen S S, Flory M R, Lee H, Martin D, Ranish J, Raught B, Schmitt R, Werner T, Kuster B, Aebersold R. Computational prediction of proteotypic peptides for quantitative proteomics. Nat. Biotechnol. 2007 January; 25(1):125-31.

Muyrers J P, Zhang Y, Benes V, Testa G, Rientjes J M, Stewart A F. ET recombination: DNA engineering using homologous recombination in *E. coli*. Methods Mol. Biol. 2004; 256:107-21.

Nagalakshmi U, Wang Z, Waern K, Shou C, Raha D, Gerstein M, Snyder M. The transcriptional landscape of the yeast genome defined by RNA sequencing. Science. 2008 Jun. 6; 320(5881):1344-9.

Oliver H F, Orsi R H, Ponnala L, Keich U, Wang W, Sun Q, Cartinhour S W, Filiatrault M J, Wiedmann M, Boor K J. Deep RNA sequencing of *L. monocytogenes* reveals overlapping and extensive stationary phase and sigma B-dependent transcriptomes, including multiple highly transcribed noncoding RNAs. BMC Genomics. 2009 Dec. 30; 10:641.

Ong S E, Blagoev B, Kratchmarova I, Kristensen D B, Steen H, Pandey A, Mann M. Stable isotope labeling by amino acids in cell culture, SILAC, as a simple and accurate approach to expression proteomics. Mol Cell Proteomics. 2002 May; 1(5):376-86.

Ong S E, Mann M. Stable isotope labeling by amino acids in cell culture for quantitative proteomics. Methods Mol. Biol. 2007; 359:37-52.

Pavelka, N., Fournier, M. L., Swanson, S. K., Pelizzola, M., Ricciardi-Castagnoli, P., Florens, L., and Washburn, M. P. (2008). Statistical similarities between transcriptomics and quantitative shotgun proteomics data. Mol Cell Proteomics 7, 631-644.

Picotti P, Bodenmiller B, Mueller L N, Domon B, Aebersold R. Full dynamic range proteome analysis of *S. cerevisiae* by targeted proteomics. Cell. 2009 Aug. 21; 138(4):795-806.

Pósfai G, Plunkett G 3rd, Fehér T, Frisch D, Keil G M, Umenhoffer K, Kolisnychenko V, Stahl B, Sharma S S, de Arruda M, Burland V, Harcum S W, Blattner F R. Emergent properties of reduced-genome *Escherichia coli*. Science. 2006 May 19; 312(5776):1044-6.

Reznikoff W S, Goryshin I Y, Jendrisak J J. Tn5 as a molecular genetics tool: In vitro transposition and the coupling of in vitro technologies with in vivo transposition. Methods Mol. Biol. 2004; 260:83-96.

Suthers P F, Dasika M S, Kumar V S, Denisov G, Glass J I, Maranas C D. A genome-scale metabolic reconstruction of *Mycoplasma genitalium*, iPS 189. PLoS Comput Biol. 2009 February; 5 (2):e1000285.

Sharan S K, Thomason L C, Kuznetsov S G, Court D L. Recombineering: a homologous recombination-based method of genetic engineering. Nat. Protoc. 2009; 4(2): 206-23.

Swingle B, Markel E, Costantino N, Bubunenko M G, Cartinhour S, Court D L. Oligonucleotide recombination in Gram-negative bacteria. Mol. Microbiol. 2010 January; 75(1):138-48.

Vickers C E, Blank L M, Kromer J O. Grand Challenge Commentary: Chassis cells for industrial biochemical production. Nat Chem. Biol. 2010 December; 6(12):875-7.

Wang H H, Isaacs F J, Carr P A, Sun Z Z, Xu G, Forest C R, Church G M. Programming cells by multiplex genome engineering and accelerated evolution. Nature. 2009 Aug. 13; 460(7257):894-8.

Webb-Robertson, B. J., Cannon, W. R., Oehmen, C. S., Shah, A. R., Gurumoorthi, V., Lipton, M. S., and Waters, K. M. A support vector machine model for the prediction of proteotypic peptides for accurate mass and time proteomics. Bioinformatics. 2010 26, 1677-1683.

Wienkoop S, Weiss J, May P, Kempa S, Irgang S, Recuenco-Munoz L, Pietzke M, Schwemmer T, Rupprecht J, Egelhofer V, Weckwerth W. Targeted proteomics for *Chlamydomonas reinhardtii* combined with rapid subcellular protein fractionation, metabolomics and metabolic flux analyses. Mol. Biosyst. 2010 Jun. 18; 6(6):1018-31.

Wolters D A, Washburn M P, Yates J R, 3rd. An automated multidimensional protein identification technology for shotgun proteomics. Anal Chem. 2001 73, 5683-5690.

Yuan J, Bennett B D, Rabinowitz J D. Kinetic flux profiling for quantitation of cellular metabolic fluxes. Nat. Protoc. 2008; 3(8):1328-40.

Yus E, Maier T, Michalodimitrakis K, van Noort V, Yamada T, Chen W H, Wodke J A, Güell M, Martínez S, Bourgeois R, Kühner S, Raineri E, Letunic I, Kalinina O V, Rode M, Herrmann R, Gutiérrez-Gallego R, Russell R B, Gavin A C, Bork P, Serrano L. Impact of genome reduction on bacterial metabolism and its regulation. Science. 2009 Nov. 27; 326(5957):1263-8.

Zhang W, Li F, Nie L. Integrating multiple 'omics' analysis for microbial biology: application and methodologies. Microbiology. 2010 February; 156 (Pt 2):287-301.

---

What is claimed is:

1. An engineered cell expressing a plurality of proteins of interest, the cell comprising a plurality of predefined, synthetic oligonucleotides introduced into the genome of the cell,
   wherein each of the plurality of oligonucleotides encodes a unique peptide tag for a predetermined protein of interest, wherein each unique peptide tag is designed to have a different quantitatively measurable value than one another,
   wherein the engineered cell expresses at least 3 tagged proteins of interest, each engineered to fuse to its corresponding unique peptide tag, and
   wherein each unique peptide tag is capable of being released from its corresponding predetermined protein of interest via proteolytic cleavage.

2. The engineered cell of claim 1, wherein the cell is a prokaryotic or eukaryotic single cell organism, a plant cell or cell line, a mammalian cell or cell line, or an insect cell or cell line.

3. The engineered cell of claim 1, wherein the cell is *Mesoplasma florum, Escherichia coli, Saccharomyces cerevisiae* or a mammalian cell line.

4. The engineered cell of claim 1, wherein each unique peptide tag is non-deleterious for functionality of its predetermined protein of interest.

5. The engineered cell of claim 1, wherein the unique peptide tags are capable of being released from their corresponding predetermined proteins of interest upon cleavage by one or more proteolytic enzymes.

6. The engineered cell of claim 1, wherein the unique peptide tags comprise an affinity tag to facilitate affinity purification of the peptide tags.

7. The engineered cell of claim 1, wherein the quantitatively measurable value is measurable via mass spectrometry.

8. The engineered cell of claim 1, wherein the unique peptide tags are separable from one another by chromatography, capillary electrophoresis or combination thereof.

9. The engineered cell of claim 1, wherein the engineered cell further comprises mutations of the genome where nonessential proteins have been modified or eliminated.

10. A method for engineering a cell, comprising:
    selecting a plurality of, at least 3 proteins of interest as subject for quantification; and
    modifying the genome of the cell such that a plurality of predetermined peptide tags are engineered onto the plurality of predetermined proteins of interest, wherein each of the plurality of predetermined peptide tags is designed to be unique to each predetermined protein of interest, separable from each predetermined protein of interest, and have a unique quantitatively measurable value than one another.

11. The method of claim 10, wherein the quantitatively measurable value is measured via mass spectrometry.

12. The method of claim 10, further comprising introducing mutations into the genome of the cell to modify or eliminate nonessential proteins, to remove background cleavage sites of a proteolytic enzyme, to remove spurious background affinity tag sites or any combinations thereof.

13. The engineered cell of claim 1, wherein the unique peptide tag is selected from a library of peptide tags each designed to have a detectable charge state with a unique mass to charge ratio,
    wherein the peptide tags have the same ionization efficiencies;
    wherein the peptide tags have minimal ion suppression;
    wherein the peptide tags comprise amino acids selected from a predetermined set of amino acids; and
    wherein the peptide tags comprise a proteolytic cleavage site.

14. The engineered cell of claim 13, wherein the peptide tags each have up to 40 amino acids selected from a predetermined set of amino acids.

15. The engineered cell of claim 13, wherein the peptide tags are designed to be engineered onto a plurality of proteins of interest in the cell, and are designed to be unique to each protein of interest in the cell.

16. The engineered cell of claim 13, wherein the peptide tags each further comprise an affinity tag.

17. The engineered cell of claim 13, wherein the peptide tags each have a fixed number of instances of each of a preselected set of one or more amino acids to facilitate isotopic labeling.

18. The engineered cell of claim 13, wherein the peptide tags are separable by chromatography, by capillary electrophoresis or combinations thereof.

19. The engineered cell of claim 13, wherein the peptide tags are capable of being enriched or purified from the background proteome by affinity purification.

20. The engineered cell of claim 1, wherein the peptide tag is used to detect a protein that is otherwise not detected due to ion suppression or ionization effects.

21. The method of claim 10, further comprising detecting a protein that is otherwise not detected due to ion suppression or ionization effects.

22. The engineered cell of claim 1, wherein the unique peptide tag is selected from a library of peptide tags each designed to have a detectable charge state with a unique mass to charge ratio.

23. The method of claim 10, wherein each predetermined peptide tag is selected from a library of peptide tags each designed to have a detectable charge state with a unique mass to charge ratio.

* * * * *

SEQUENCE LISTING

```
<160> NUMBER OF SEQ ID NOS: 98

<210> SEQ ID NO 1
<211> LENGTH: 19
<212> TYPE: PRT
<213> ORGANISM: Artificial Sequence
<220> FEATURE:
<223> OTHER INFORMATION: synthetic construct

<400> SEQUENCE: 1

Met Asp Arg Val Tyr Ile His Pro Phe His Leu Leu Glu Val Leu Phe
1               5                   10                  15

Gln Gly Pro

<210> SEQ ID NO 2
<211> LENGTH: 17
<212> TYPE: PRT
<213> ORGANISM: Artificial Sequence
<220> FEATURE:
<223> OTHER INFORMATION: Synthetic construct

<400> SEQUENCE: 2

Met Asp Arg Val Tyr Ile His Pro Phe Leu Glu Val Leu Phe Gln Gly
1               5                   10                  15

Pro

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Met Tyr Gly Gly Phe Leu Leu Glu Val Leu Phe Gln Gly Pro
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Met His Ser Asp Ala Val Phe Thr Asp Asn Thr Arg Leu Glu Val Leu
1               5                   10                  15

Phe Gln Gly Pro
            20
```

```
<210> SEQ ID NO 5
<211> LENGTH: 23
<212> TYPE: PRT
<213> ORGANISM: Artificial Sequence
<220> FEATURE:
<223> OTHER INFORMATION: Synthetic Construct

<400> SEQUENCE: 5

Met Glu Gly Val Asn Asp Asn Glu Glu Gly Phe Phe Ser Ala Arg Leu
1               5                   10                  15

Glu Val Leu Phe Gln Gly Pro
            20

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6

Met Arg Pro Pro Gly Phe Ser Pro Leu Glu Val Leu Phe Gln Gly Pro
1               5                   10                  15

<210> SEQ ID NO 7
<211> LENGTH: 31
<212> TYPE: PRT
<213> ORGANISM: Artificial Sequence
<220> FEATURE:
<223> OTHER INFORMATION: Synthetic Construct

<400> SEQUENCE: 7

Met Arg Pro Val Lys Val Tyr Pro Asn Gly Ala Glu Asp Glu Ser Ala
1               5                   10                  15

Glu Ala Phe Pro Leu Glu Phe Leu Glu Val Leu Phe Gln Gly Pro
            20                  25                  30

<210> SEQ ID NO 8
<211> LENGTH: 18
<212> TYPE: PRT
<213> ORGANISM: Artificial Sequence
<220> FEATURE:
<223> OTHER INFORMATION: Synthetic Construct

<400> SEQUENCE: 8

Leu Glu Val Leu Phe Gln Gly Pro Asp Arg Val Tyr Ile His Pro Phe
1               5                   10                  15

His Leu

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct

<400> SEQUENCE: 9

Leu Glu Val Leu Phe Gln Gly Pro Asp Arg Val Tyr Ile His Pro Phe
1               5                   10                  15

<210> SEQ ID NO 10
<211> LENGTH: 13
<212> TYPE: PRT
<213> ORGANISM: Artificial Sequence
<220> FEATURE:
```

```
<223> OTHER INFORMATION: Synthetic Construct

<400> SEQUENCE: 10

Leu Glu Val Leu Phe Gln Gly Pro Tyr Gly Gly Phe Leu
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Synthetic Construct

<400> SEQUENCE: 11

Leu Glu Val Leu Phe Gln Gly Pro His Ser Asp Ala Val Phe Thr Asp
1               5                   10                  15

Asn Thr Arg

<210> SEQ ID NO 12
<211> LENGTH: 22
<212> TYPE: PRT
<213> ORGANISM: Artificial Sequence
<220> FEATURE:
<223> OTHER INFORMATION: Synthetic Construct

<400> SEQUENCE: 12

Leu Glu Val Leu Phe Gln Gly Pro Glu Gly Val Asn Asp Asn Glu Glu
1               5                   10                  15

Gly Phe Phe Ser Ala Arg
            20

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Leu Glu Val Leu Phe Gln Gly Pro Arg Pro Pro Gly Phe Ser Pro
1               5                   10                  15

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct

<400> SEQUENCE: 14

Leu Glu Val Leu Phe Gln Gly Pro Arg Pro Val Lys Val Tyr Pro Asn
1               5                   10                  15

Gly Ala Glu Asp Glu Ser Ala Glu Ala Phe Pro Leu Glu Phe
            20                  25                  30

<210> SEQ ID NO 15
<211> LENGTH: 29
<212> TYPE: PRT
<213> ORGANISM: Artificial Sequence
<220> FEATURE:
<223> OTHER INFORMATION: Synthetic Construct

<400> SEQUENCE: 15

Met Glu Gln Lys Leu Ile Ser Glu Glu Asp Leu Asp Arg Val Tyr Ile
1               5                   10                  15
```

His Pro Phe His Leu Glu Val Leu Gly Gln Gly Pro
            20                  25

<210> SEQ ID NO 16
<211> LENGTH: 27
<212> TYPE: PRT
<213> ORGANISM: Artificial Sequence
<220> FEATURE:
<223> OTHER INFORMATION: Synthetic Construct

<400> SEQUENCE: 16

Met Glu Gln Lys Leu Ile Ser Glu Glu Asp Leu Asp Arg Val Tyr Ile
1               5                   10                  15

His Pro Phe Leu Glu Val Leu Gly Gln Gly Pro
            20                  25

<210> SEQ ID NO 17
<211> LENGTH: 24
<212> TYPE: PRT
<213> ORGANISM: Artificial Sequence
<220> FEATURE:
<223> OTHER INFORMATION: Synthetic Construct

<400> SEQUENCE: 17

Met Glu Gln Lys Leu Ile Ser Glu Glu Asp Leu Tyr Gly Gly Phe Leu
1               5                   10                  15

Leu Glu Val Leu Gly Gln Gly Pro
            20

<210> SEQ ID NO 18
<211> LENGTH: 30
<212> TYPE: PRT
<213> ORGANISM: Artificial Sequence
<220> FEATURE:
<223> OTHER INFORMATION: Synthetic Construct

<400> SEQUENCE: 18

Met Glu Gln Lys Leu Ile Ser Glu Glu Asp Leu His Ser Asp Ala Val
1               5                   10                  15

Phe Thr Asp Asn Thr Arg Leu Glu Val Leu Gly Gln Gly Pro
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: Synthetic Construct

<400> SEQUENCE: 19

Met Glu Gln Lys Leu Ile Ser Glu Glu Asp Leu Glu Gly Val Asn Asp
1               5                   10                  15

Asn Glu Glu Gly Phe Phe Ser Ala Arg Leu Glu Val Leu Gly Gln Gly
            20                  25                  30

Pro

<210> SEQ ID NO 20
<211> LENGTH: 26
<212> TYPE: PRT
<213> ORGANISM: Artificial Sequence
<220> FEATURE:
<223> OTHER INFORMATION: Synthetic Construct

<400> SEQUENCE: 20

```
Met Glu Gln Lys Leu Ile Ser Glu Glu Asp Leu Arg Pro Pro Gly Phe
1               5                   10                  15

Ser Pro Leu Glu Val Leu Gly Gln Gly Pro
            20                  25
```

<210> SEQ ID NO 21
<211> LENGTH: 41
<212> TYPE: PRT
<213> ORGANISM: Artificial Sequence
<220> FEATURE:
<223> OTHER INFORMATION: Synthetic Construct

<400> SEQUENCE: 21

```
Met Glu Gln Lys Leu Ile Ser Glu Glu Asp Leu Arg Pro Val Lys Val
1               5                   10                  15

Tyr Pro Asn Gly Ala Glu Asp Glu Ser Ala Glu Ala Phe Pro Leu Glu
                20                  25                  30

Phe Leu Glu Val Leu Gly Gln Gly Pro
            35                  40
```

<210> SEQ ID NO 22
<211> LENGTH: 28
<212> TYPE: PRT
<213> ORGANISM: Artificial Sequence
<220> FEATURE:
<223> OTHER INFORMATION: Synthetic Construct

<400> SEQUENCE: 22

```
Leu Glu Val Leu Gly Gln Gly Pro Asp Arg Val Tyr Ile His Pro Phe
1               5                   10                  15

His Leu Glu Gln Lys Leu Ile Ser Glu Glu Asp Leu
                20                  25
```

<210> SEQ ID NO 23
<211> LENGTH: 26
<212> TYPE: PRT
<213> ORGANISM: Artificial Sequence
<220> FEATURE:
<223> OTHER INFORMATION: Synthetic Construct

<400> SEQUENCE: 23

```
Leu Glu Val Leu Gly Gln Gly Pro Asp Arg Val Tyr Ile His Pro Phe
1               5                   10                  15

Glu Gln Lys Leu Ile Ser Glu Glu Asp Leu
                20                  25
```

<210> SEQ ID NO 24
<211> LENGTH: 23
<212> TYPE: PRT
<213> ORGANISM: Artificial Sequence
<220> FEATURE:
<223> OTHER INFORMATION: Synthetic Construct

<400> SEQUENCE: 24

```
Leu Glu Val Leu Gly Gln Gly Pro Tyr Gly Gly Phe Leu Glu Gln Lys
1               5                   10                  15

Leu Ile Ser Glu Glu Asp Leu
            20
```

<210> SEQ ID NO 25
<211> LENGTH: 29
<212> TYPE: PRT
<213> ORGANISM: Artificial Sequence

```
<220> FEATURE:
<223> OTHER INFORMATION: Synthetic Construct

<400> SEQUENCE: 25

Leu Glu Val Leu Gly Gln Gly Pro His Ser Asp Ala Val Phe Thr Asp
1               5                   10                  15

Asn Thr Arg Glu Gln Lys Leu Ile Ser Glu Glu Asp Leu
            20                  25

<210> SEQ ID NO 26
<211> LENGTH: 32
<212> TYPE: PRT
<213> ORGANISM: Artificial Sequence
<220> FEATURE:
<223> OTHER INFORMATION: Synthetic Construct

<400> SEQUENCE: 26

Leu Glu Val Leu Gly Gln Gly Pro Glu Gly Val Asn Asp Asn Glu Glu
1               5                   10                  15

Gly Phe Phe Ser Ala Arg Glu Gln Lys Leu Ile Ser Glu Glu Asp Leu
            20                  25                  30

<210> SEQ ID NO 27
<211> LENGTH: 25
<212> TYPE: PRT
<213> ORGANISM: Artificial Sequence
<220> FEATURE:
<223> OTHER INFORMATION: Synthetic Construct

<400> SEQUENCE: 27

Leu Glu Val Leu Gly Gln Gly Pro Arg Pro Pro Gly Phe Ser Pro Glu
1               5                   10                  15

Gln Lys Leu Ile Ser Glu Glu Asp Leu
            20                  25

<210> SEQ ID NO 28
<211> LENGTH: 40
<212> TYPE: PRT
<213> ORGANISM: Artificial Sequence
<220> FEATURE:
<223> OTHER INFORMATION: Synthetic Construct

<400> SEQUENCE: 28

Leu Glu Val Leu Gly Gln Gly Pro Arg Pro Val Lys Val Tyr Pro Asn
1               5                   10                  15

Gly Ala Glu Asp Glu Ser Ala Glu Ala Phe Pro Leu Glu Phe Glu Gln
            20                  25                  30

Lys Leu Ile Ser Glu Glu Asp Leu
        35                  40

<210> SEQ ID NO 29
<211> LENGTH: 28
<212> TYPE: PRT
<213> ORGANISM: Artificial Sequence
<220> FEATURE:
<223> OTHER INFORMATION: Synthetic Construct

<400> SEQUENCE: 29

Met Tyr Pro Tyr Asp Val Pro Asp Tyr Ala Asp Arg Val Tyr Ile His
1               5                   10                  15

Pro Phe His Leu Leu Glu Val Leu Gly Gln Gly Pro
            20                  25
```

```
<210> SEQ ID NO 30
<211> LENGTH: 26
<212> TYPE: PRT
<213> ORGANISM: Artificial Sequence
<220> FEATURE:
<223> OTHER INFORMATION: Synthetic Construct

<400> SEQUENCE: 30

Met Tyr Pro Tyr Asp Val Pro Asp Tyr Ala Asp Arg Val Tyr Ile His
1               5                   10                  15

Pro Phe Leu Glu Val Leu Gly Gln Gly Pro
            20                  25

<210> SEQ ID NO 31
<211> LENGTH: 23
<212> TYPE: PRT
<213> ORGANISM: Artificial Sequence
<220> FEATURE:
<223> OTHER INFORMATION: Synthetic Construct

<400> SEQUENCE: 31

Met Tyr Pro Tyr Asp Val Pro Asp Tyr Ala Tyr Gly Gly Phe Leu Leu
1               5                   10                  15

Glu Val Leu Gly Gln Gly Pro
            20

<210> SEQ ID NO 32
<211> LENGTH: 29
<212> TYPE: PRT
<213> ORGANISM: Artificial Sequence
<220> FEATURE:
<223> OTHER INFORMATION: Synthetic Construct

<400> SEQUENCE: 32

Met Tyr Pro Tyr Asp Val Pro Asp Tyr Ala His Ser Asp Ala Val Phe
1               5                   10                  15

Thr Asp Asn Thr Arg Leu Glu Val Leu Gly Gln Gly Pro
            20                  25

<210> SEQ ID NO 33
<211> LENGTH: 32
<212> TYPE: PRT
<213> ORGANISM: Artificial Sequence
<220> FEATURE:
<223> OTHER INFORMATION: Synthetic Construct

<400> SEQUENCE: 33

Met Tyr Pro Tyr Asp Val Pro Asp Tyr Ala Glu Gly Val Asn Asp Asn
1               5                   10                  15

Glu Glu Gly Phe Phe Ser Ala Arg Leu Glu Val Leu Gly Gln Gly Pro
            20                  25                  30

<210> SEQ ID NO 34
<211> LENGTH: 25
<212> TYPE: PRT
<213> ORGANISM: Artificial Sequence
<220> FEATURE:
<223> OTHER INFORMATION: Synthetic Construct

<400> SEQUENCE: 34

Met Tyr Pro Tyr Asp Val Pro Asp Tyr Ala Arg Pro Pro Gly Phe Ser
1               5                   10                  15

Pro Leu Glu Val Leu Gly Gln Gly Pro
            20                  25
```

```
<210> SEQ ID NO 35
<211> LENGTH: 40
<212> TYPE: PRT
<213> ORGANISM: Artificial Sequence
<220> FEATURE:
<223> OTHER INFORMATION: Synthetic Construct

<400> SEQUENCE: 35

Met Tyr Pro Tyr Asp Val Pro Asp Tyr Ala Arg Pro Val Lys Val Tyr
1               5                   10                  15

Pro Asn Gly Ala Glu Asp Glu Ser Ala Glu Ala Phe Pro Leu Glu Phe
            20                  25                  30

Leu Glu Val Leu Gly Gln Gly Pro
        35                  40

<210> SEQ ID NO 36
<211> LENGTH: 27
<212> TYPE: PRT
<213> ORGANISM: Artificial Sequence
<220> FEATURE:
<223> OTHER INFORMATION: Synthetic Construct

<400> SEQUENCE: 36

Leu Glu Val Leu Gly Gln Gly Pro Asp Arg Val Tyr Ile His Pro Phe
1               5                   10                  15

His Leu Tyr Pro Tyr Asp Val Pro Asp Tyr Ala
            20                  25

<210> SEQ ID NO 37
<211> LENGTH: 25
<212> TYPE: PRT
<213> ORGANISM: Artificial Sequence
<220> FEATURE:
<223> OTHER INFORMATION: Synthetic Construct

<400> SEQUENCE: 37

Leu Glu Val Leu Gly Gln Gly Pro Asp Arg Val Tyr Ile His Pro Phe
1               5                   10                  15

Tyr Pro Tyr Asp Val Pro Asp Tyr Ala
            20                  25

<210> SEQ ID NO 38
<211> LENGTH: 22
<212> TYPE: PRT
<213> ORGANISM: Artificial Sequence
<220> FEATURE:
<223> OTHER INFORMATION: Synthetic Construct

<400> SEQUENCE: 38

Leu Glu Val Leu Gly Gln Gly Pro Tyr Gly Gly Phe Leu Tyr Pro Tyr
1               5                   10                  15

Asp Val Pro Asp Tyr Ala
            20

<210> SEQ ID NO 39
<211> LENGTH: 28
<212> TYPE: PRT
<213> ORGANISM: Artificial Sequence
<220> FEATURE:
<223> OTHER INFORMATION: Synthetic Construct

<400> SEQUENCE: 39

Leu Glu Val Leu Gly Gln Gly Pro His Ser Asp Ala Val Phe Thr Asp
1               5                   10                  15
```

Asn Thr Arg Tyr Pro Tyr Asp Val Pro Asp Tyr Ala
            20                  25

<210> SEQ ID NO 40
<211> LENGTH: 31
<212> TYPE: PRT
<213> ORGANISM: Artificial Sequence
<220> FEATURE:
<223> OTHER INFORMATION: Synthetic Construct

<400> SEQUENCE: 40

Leu Glu Val Leu Gly Gln Gly Pro Gly Val Asn Asp Asn Glu Glu
1               5                   10                  15

Gly Phe Phe Ser Ala Arg Tyr Pro Tyr Asp Val Pro Asp Tyr Ala
            20                  25                  30

<210> SEQ ID NO 41
<211> LENGTH: 24
<212> TYPE: PRT
<213> ORGANISM: Artificial Sequence
<220> FEATURE:
<223> OTHER INFORMATION: Synthetic Construct

<400> SEQUENCE: 41

Leu Glu Val Leu Gly Gln Gly Pro Arg Pro Pro Gly Phe Ser Pro Tyr
1               5                   10                  15

Pro Tyr Asp Val Pro Asp Tyr Ala
            20

<210> SEQ ID NO 42
<211> LENGTH: 39
<212> TYPE: PRT
<213> ORGANISM: Artificial Sequence
<220> FEATURE:
<223> OTHER INFORMATION: Synthetic Construct

<400> SEQUENCE: 42

Leu Glu Val Leu Gly Gln Gly Pro Arg Pro Val Lys Val Tyr Pro Asn
1               5                   10                  15

Gly Ala Glu Asp Glu Ser Ala Glu Ala Phe Pro Leu Glu Phe Tyr Pro
            20                  25                  30

Tyr Asp Val Pro Asp Tyr Ala
        35

<210> SEQ ID NO 43
<211> LENGTH: 57
<212> TYPE: DNA
<213> ORGANISM: Artificial Sequence
<220> FEATURE:
<223> OTHER INFORMATION: Synthetic Construct

<400> SEQUENCE: 43
atggaccgtg tatatattca ccctttttcat ttattagaag tacttttcca aggtcca        57

<210> SEQ ID NO 44
<211> LENGTH: 51
<212> TYPE: DNA
<213> ORGANISM: Artificial Sequence
<220> FEATURE:
<223> OTHER INFORMATION: Synthetic Construct

<400> SEQUENCE: 44
atggaccgtg tatatattca cccttttta gaagtacttt tccaaggtcc a        51

<210> SEQ ID NO 45
<211> LENGTH: 42
<212> TYPE: DNA
<213> ORGANISM: Artificial Sequence
<220> FEATURE:
<223> OTHER INFORMATION: Synthetic Construct

<400> SEQUENCE: 45
atgtacggag gttttctttt agaagtactt ttccaaggtc ca           42

<210> SEQ ID NO 46
<211> LENGTH: 60
<212> TYPE: DNA
<213> ORGANISM: Artificial Sequence
<220> FEATURE:
<223> OTHER INFORMATION: Synthetic Construct

<400> SEQUENCE: 46
atgcatagtg atgctgtatt tacagataac actcgtttag aagtactttt ccaaggtcca    60

<210> SEQ ID NO 47
<211> LENGTH: 69
<212> TYPE: DNA
<213> ORGANISM: Artificial Sequence
<220> FEATURE:
<223> OTHER INFORMATION: Synthetic Construct

<400> SEQUENCE: 47
atggagggag taaacgataa tgaggaaggt ttctttagtg ctcgtttaga agtacttttc    60
caaggtcca                                                             69

<210> SEQ ID NO 48
<211> LENGTH: 48
<212> TYPE: DNA
<213> ORGANISM: Artificial Sequence
<220> FEATURE:
<223> OTHER INFORMATION: Synthetic Construct

<400> SEQUENCE: 48
atgcgtccac ctggatttag tcctttagaa gtacttttcc aaggtcca    48

<210> SEQ ID NO 49
<211> LENGTH: 93
<212> TYPE: DNA
<213> ORGANISM: Artificial Sequence
<220> FEATURE:
<223> OTHER INFORMATION: Synthetic Construct

<400> SEQUENCE: 49
atgcgtcctg taaaagtata cccaaatgga gctgaggatg aaagtgcaga ggcttttcct    60
ttagaatttt tagaagtact tttccaaggt cca                                  93

<210> SEQ ID NO 50
<211> LENGTH: 87
<212> TYPE: DNA
<213> ORGANISM: Artificial Sequence
<220> FEATURE:
<223> OTHER INFORMATION: Synthetic Construct

<400> SEQUENCE: 50
atggaacaaa aacttatttc agaggaagac ttagaccgtg tatatattca ccctttcat     60 ttattagaag tacttttcca aggtcca                                         87

```
<210> SEQ ID NO 51
<211> LENGTH: 81
<212> TYPE: DNA
<213> ORGANISM: Artificial Sequence
<220> FEATURE:
<223> OTHER INFORMATION: Synthetic Construct

<400> SEQUENCE: 51
atggaacaaa aacttatttc agaggaagac ttagaccgtg tatatattca cccttttta      60 gaagtacttt tccaaggtcc a                                                81

<210> SEQ ID NO 52
<211> LENGTH: 72
<212> TYPE: DNA
<213> ORGANISM: Artificial Sequence
<220> FEATURE:
<223> OTHER INFORMATION: Synthetic Construct

<400> SEQUENCE: 52
atggaacaaa aacttatttc agaggaagac ttatacggag gttttctttt agaagtactt      60
ttccaaggtc ca                                                          72

<210> SEQ ID NO 53
<211> LENGTH: 90
<212> TYPE: DNA
<213> ORGANISM: Artificial Sequence
<220> FEATURE:
<223> OTHER INFORMATION: Synthetic Construct

<400> SEQUENCE: 53
atggaacaaa aacttatttc agaggaagac ttacatagtg atgctgtatt tacagataac      60
actcgtttag aagtactttt ccaaggtcca                                       90

<210> SEQ ID NO 54
<211> LENGTH: 99
<212> TYPE: DNA
<213> ORGANISM: Artificial Sequence
<220> FEATURE:
<223> OTHER INFORMATION: Synthetic Construct

<400> SEQUENCE: 54
atggaacaaa aacttatttc agaggaagac ttagagggag taaacgataa tgaggaaggt      60
ttctttagtg ctcgtttaga agtactttc caaggtcca                             99

<210> SEQ ID NO 55
<211> LENGTH: 78
<212> TYPE: DNA
<213> ORGANISM: Artificial Sequence
<220> FEATURE:
<223> OTHER INFORMATION: Synthetic Construct

<400> SEQUENCE: 55
atggaacaaa aacttatttc agaggaagac ttacgtccac ctggatttag tcctttagaa      60
gtacttttcc aaggtcca                                                    78

<210> SEQ ID NO 56
<211> LENGTH: 84
<212> TYPE: DNA
<213> ORGANISM: Artificial Sequence
<220> FEATURE:
<223> OTHER INFORMATION: Synthetic Construct

<400> SEQUENCE: 56
```

```
atgtatcctt acgacgttcc agactatgca gaccgtgtat atattcaccc ttttcattta    60
ttagaagtac ttttccaagg tcca                                           84

<210> SEQ ID NO 57
<211> LENGTH: 78
<212> TYPE: DNA
<213> ORGANISM: Artificial Sequence
<220> FEATURE:
<223> OTHER INFORMATION: Synthetic Construct

<400> SEQUENCE: 57
atgtatcctt acgacgttcc agactatgca gaccgtgtat atattcaccc tttttagaa    60 gtacttttcc aaggtcca                                                  78

<210> SEQ ID NO 58
<211> LENGTH: 69
<212> TYPE: DNA
<213> ORGANISM: Artificial Sequence
<220> FEATURE:
<223> OTHER INFORMATION: Synthetic Construct

<400> SEQUENCE: 58
atgtatcctt acgacgttcc agactatgca tacggaggtt ttcttttaga agtacttttc    60
caaggtcca                                                            69

<210> SEQ ID NO 59
<211> LENGTH: 87
<212> TYPE: DNA
<213> ORGANISM: Artificial Sequence
<220> FEATURE:
<223> OTHER INFORMATION: Synthetic Construct

<400> SEQUENCE: 59
atgtatcctt acgacgttcc agactatgca catagtgatg ctgtatttac agataacact    60
cgtttagaag tacttttcca aggtcca                                        87

<210> SEQ ID NO 60
<211> LENGTH: 96
<212> TYPE: DNA
<213> ORGANISM: Artificial Sequence
<220> FEATURE:
<223> OTHER INFORMATION: Synthetic Construct

<400> SEQUENCE: 60
atgtatcctt acgacgttcc agactatgca gagggagtaa acgataatga ggaaggtttc    60
tttagtgctc gtttagaagt acttttccaa ggtcca                              96

<210> SEQ ID NO 61
<211> LENGTH: 75
<212> TYPE: DNA
<213> ORGANISM: Artificial Sequence
<220> FEATURE:
<223> OTHER INFORMATION: Synthetic Construct

<400> SEQUENCE: 61
atgtatcctt acgacgttcc agactatgca cgtccacctg gatttagtcc tttagaagta    60
cttttccaag gtcca                                                     75

<210> SEQ ID NO 62
<211> LENGTH: 120
<212> TYPE: DNA
<213> ORGANISM: Artificial Sequence
```

<220> FEATURE:
<223> OTHER INFORMATION: Synthetic Construct

<400> SEQUENCE: 62
atgtatcctt acgacgttcc agactatgca cgtcctgtaa aagtataccc aaatggagct    60
gaggatgaaa gtgcagaggc ttttccttta gaatttttag aagtactttt ccaaggtcca    120

<210> SEQ ID NO 63
<211> LENGTH: 57
<212> TYPE: DNA
<213> ORGANISM: Artificial Sequence
<220> FEATURE:
<223> OTHER INFORMATION: Synthetic Construct

<400> SEQUENCE: 63
ttagaagtac ttttccaagg tccagaccgt gtatatattc ccctttcca tttataa    57

<210> SEQ ID NO 64
<211> LENGTH: 51
<212> TYPE: DNA
<213> ORGANISM: Artificial Sequence
<220> FEATURE:
<223> OTHER INFORMATION: Synthetic Construct

<400> SEQUENCE: 64
ttagaagtac ttttccaagg tccagaccgt gtatatattc cccttttta a    51

<210> SEQ ID NO 65
<211> LENGTH: 42
<212> TYPE: DNA
<213> ORGANISM: Artificial Sequence
<220> FEATURE:
<223> OTHER INFORMATION: Synthetic Construct

<400> SEQUENCE: 65
ttagaagtac ttttccaagg tccatacgga ggttttcttt aa    42

<210> SEQ ID NO 66
<211> LENGTH: 60
<212> TYPE: DNA
<213> ORGANISM: Artificial Sequence
<220> FEATURE:
<223> OTHER INFORMATION: Synthetic Construct

<400> SEQUENCE: 66
ttagaagtac ttttccaagg tccacatagt gatgctgtat ttacagataa cactcgttaa    60

<210> SEQ ID NO 67
<211> LENGTH: 69
<212> TYPE: DNA
<213> ORGANISM: Artificial Sequence
<220> FEATURE:
<223> OTHER INFORMATION: Synthetic Construct

<400> SEQUENCE: 67
ttagaagtac ttttccaagg tccagaggga gtaaacgata atgaggaagg tttctttagt    60
gctcgttaa    69

<210> SEQ ID NO 68
<211> LENGTH: 48
<212> TYPE: DNA
<213> ORGANISM: Artificial Sequence
<220> FEATURE:
<223> OTHER INFORMATION: Synthetic Construct

<400> SEQUENCE: 68
ttagaagtac ttttccaagg tccacgtcca cctggattta gtccttaa          48

<210> SEQ ID NO 69
<211> LENGTH: 93
<212> TYPE: DNA
<213> ORGANISM: Artificial Sequence
<220> FEATURE:
<223> OTHER INFORMATION: Synthetic Construct

<400> SEQUENCE: 69
ttagaagtac ttttccaagg tccacgtcct gtaaaagtat acccaaatgg agctgaggat    60
gaaagtgcag aggcttttcc tttagaattt taa                                 93

<210> SEQ ID NO 70
<211> LENGTH: 87
<212> TYPE: DNA
<213> ORGANISM: Artificial Sequence
<220> FEATURE:
<223> OTHER INFORMATION: Synthetic Construct

<400> SEQUENCE: 70
ttagaagtac ttttccaagg tccagaccgt gtatatattc acccttttca tttagaacaa    60
aaacttattt cagaggaaga cttataa                                        87

<210> SEQ ID NO 71
<211> LENGTH: 81
<212> TYPE: DNA
<213> ORGANISM: Artificial Sequence
<220> FEATURE:
<223> OTHER INFORMATION: Synthetic Construct

<400> SEQUENCE: 71
ttagaagtac ttttccaagg tccagaccgt gtatatattc accctttga acaaaaactt     60 atttcagagg aagacttata a                                              81

<210> SEQ ID NO 72
<211> LENGTH: 72
<212> TYPE: DNA
<213> ORGANISM: Artificial Sequence
<220> FEATURE:
<223> OTHER INFORMATION: Synthetic Construct

<400> SEQUENCE: 72
ttagaagtac ttttccaagg tccatacgga ggttttcttg aacaaaaact tatttcagag    60
gaagacttat aa                                                        72

<210> SEQ ID NO 73
<211> LENGTH: 90
<212> TYPE: DNA
<213> ORGANISM: Artificial Sequence
<220> FEATURE:
<223> OTHER INFORMATION: Synthetic Construct

<400> SEQUENCE: 73
ttagaagtac ttttccaagg tccacatagt gatgctgtat ttacagataa cactcgtgaa    60
caaaaactta tttcagagga agacttataa                                     90

<210> SEQ ID NO 74
<211> LENGTH: 99
<212> TYPE: DNA
<213> ORGANISM: Artificial Sequence

```
<220> FEATURE:
<223> OTHER INFORMATION: Synthetic Construct

<400> SEQUENCE: 74
ttagaagtac ttttccaagg tccagaggga gtaaacgata atgaggaagg tttctttagt      60
gctcgtgaac aaaaacttat ttcagaggaa gacttataa                             99

<210> SEQ ID NO 75
<211> LENGTH: 78
<212> TYPE: DNA
<213> ORGANISM: Artificial Sequence
<220> FEATURE:
<223> OTHER INFORMATION: Synthetic Construct

<400> SEQUENCE: 75
ttagaagtac ttttccaagg tccacgtcca cctggattta gtcctgaaca aaaacttatt      60
tcagaggaag acttataa                                                   78

<210> SEQ ID NO 76
<211> LENGTH: 123
<212> TYPE: DNA
<213> ORGANISM: Artificial Sequence
<220> FEATURE:
<223> OTHER INFORMATION: Synthetic Construct

<400> SEQUENCE: 76
ttagaagtac ttttccaagg tccacgtcct gtaaaagtat acccaaatgg agctgaggat      60
gaaagtgcag aggcttttcc tttagaattt gaacaaaaac ttatttcaga ggaagactta     120
taa                                                                   123

<210> SEQ ID NO 77
<211> LENGTH: 84
<212> TYPE: DNA
<213> ORGANISM: Artificial Sequence
<220> FEATURE:
<223> OTHER INFORMATION: Synthetic Construct

<400> SEQUENCE: 77
ttagaagtac ttttccaagg tccagaccgt gtatatattc ccctttttca tttatatcct      60
tacgacgttc cagactatgc ataa                                            84

<210> SEQ ID NO 78
<211> LENGTH: 78
<212> TYPE: DNA
<213> ORGANISM: Artificial Sequence
<220> FEATURE:
<223> OTHER INFORMATION: Synthetic Construct

<400> SEQUENCE: 78
ttagaagtac ttttccaagg tccagaccgt gtatatattc cccttttta tccttacgac       60 gttccagact atgcataa                                                   78

<210> SEQ ID NO 79
<211> LENGTH: 69
<212> TYPE: DNA
<213> ORGANISM: Artificial Sequence
<220> FEATURE:
<223> OTHER INFORMATION: Synthetic Construct

<400> SEQUENCE: 79
ttagaagtac ttttccaagg tccatacgga ggttttcttt atccttacga cgttccagac      60
```

```
<210> SEQ ID NO 80
<211> LENGTH: 87
<212> TYPE: DNA
<213> ORGANISM: Artificial Sequence
<220> FEATURE:
<223> OTHER INFORMATION: Synthetic Construct

<400> SEQUENCE: 80
ttagaagtac ttttccaagg tccacatagt gatgctgtat ttacagataa cactcgttat    60
ccttacgacg ttccagacta tgcataa                                        87

<210> SEQ ID NO 81
<211> LENGTH: 96
<212> TYPE: DNA
<213> ORGANISM: Artificial Sequence
<220> FEATURE:
<223> OTHER INFORMATION: Synthetic Construct

<400> SEQUENCE: 81
ttagaagtac ttttccaagg tccagaggga gtaaacgata atgaggaagg tttctttagt    60
gctcgttatc cttacgacgt tccagactat gcataa                              96

<210> SEQ ID NO 82
<211> LENGTH: 75
<212> TYPE: DNA
<213> ORGANISM: Artificial Sequence
<220> FEATURE:
<223> OTHER INFORMATION: Synthetic Construct

<400> SEQUENCE: 82
ttagaagtac ttttccaagg tccacgtcca cctggattta gtccttatcc ttacgacgtt    60
ccagactatg cataa                                                     75

<210> SEQ ID NO 83
<211> LENGTH: 120
<212> TYPE: DNA
<213> ORGANISM: Artificial Sequence
<220> FEATURE:
<223> OTHER INFORMATION: Synthetic Construct

<400> SEQUENCE: 83
ttagaagtac ttttccaagg tccacgtcct gtaaaagtat acccaaatgg agctgaggat    60
gaaagtgcag aggcttttcc tttagaattt tatccttacg acgttccaga ctatgcataa   120

<210> SEQ ID NO 84
<211> LENGTH: 4965
<212> TYPE: DNA
<213> ORGANISM: Artificial Sequence
<220> FEATURE:
<223> OTHER INFORMATION: Synthetic Construct

<400> SEQUENCE: 84
cagctgtctc ttatacacat ctcacagcta acaccacgtc gtccctatct gctgccctag    60
gtctatgagt ggttgctgga taactttacg ggcatgcata aggctcgtat aatatattca   120
gggagaccac aacggtttcc ctctacaaat aattttgttt aactttgcct cacacaggaa   180
agtactagat ggatcgtgta tatattcacc cttttcattt attagaagta cttttccaag   240
gtccaatggc tagtagtgag gatataatca aagagtttat gcgttttaaa gttcacatgg   300
aaggttcagt aaacggacat gaatttgaaa ttgagggaga aggagagggt cgtccgtacg   360
```

```
aaggtacaca aacagcaaag ttaaaagtaa caaaaggagg acctttacca tttgcatggg    420
atattctttc tccacaattt atgtatggta gtaaagcgta tgttaaacac ccggcagata    480
taccagacta tttaaagttg agttttccgg aaggattcaa atgggaacgt gttatgaatt    540
ttgaagatgg tggtgttgtt acagttactc aagatagtag cttacaggat ggtgaattta    600
tttacaaagt aaaattacgt ggtactaact tcccgagcga tggtccagta atgcaaaaga    660
aaactatggg atgggaggct agttctgaac gtatgtatcc tgaagacggt gctttaaaag    720
gagaaattaa acaacgtttg aaacttaaag atggtggaca ctacgatgca gaagttaaaa    780
ctacatataa agctaaaaag cctgttcagc ttccgggtgc ttataatgtg aatataaaat    840
tagatatcac aagtcataac gaagattata ctattgttga acagtatgaa agagcagaag    900
gaagacattc tacaggagca gcctaaccag gcatcaaata aaacgaaagg ctcagtcgaa    960
agactgggcc tttcgtttta tctgttgttt gtcggtgaac gctctctact agagtcacac   1020
tggctcacct tcgggtgggc ctttctgcgt ttatagccgg ccagtctaca tgtactcttt   1080
ttgataaaaa attggagatt cctttacaaa tatgctctta cgtgctatta tttaagtgac   1140
tatttaaaag gagttaataa atatgcggca aggtattctt aaataaactg tcaatttgat   1200
agcgggaaca ataattaga tgtcctttt taggagggct tagttttttg tacccagttt   1260
aagaatacct ttatcatgtg attctaaagt atccagagaa tatctgtatg ctttgtatac   1320
ctatggttat gcataaaaat cccggtgata aaagtattta tcactgggat tttatgccc    1380 ttttgggttt ttgaatggag gaatactaga tgaaaatcat aaatatcggt gtattagctc   1440
acgttgatgc aggaaaaaca acattaactg aatcactttt atataactct ggtgcaatta   1500
ctgaacttgg ttcagtagat aaaggtacta ctcgtactga taatacatta ttagaacgtc   1560
aacgtggaat cacaattcaa acaggtatca catcttttca atgggaaaat acaaaagtaa   1620
atattataga tacacctgga cacatggatt ccttgcaga agtataccgt agtctttcag   1680
tattagatgg tgctatttta cttatcagcg ctaaagatgg agttcaagct caaactcgta   1740
tcttatttca cgcattacgt aaaatgggta ttccaacaat tttctttata aacaaaattg   1800
accaaaacgg aattgattta agtacagttt atcaagatat caaagaaaaa ctttctgctg   1860
aaatcgttat taaacaaaaa gttgaattat acccaaacgt ttgcgtaaca aattttactg   1920
aatcagaaca atgggataca gttatagaag gtaatgatga tttattagaa aaatacatgt   1980
caggtaaatc attagaagca ttagaattag aacaagaaga agtattcgt ttccaaaact    2040 gttctttatt ccctttatac catggaagcg ctaaagtaa cataggtatt gataacttaa    2100
ttgaagttat tactaacaaa ttttattctt caactcatcg tgggccttct gaattatgcg   2160
gtaacgtttt caaaattgaa tatacaaaaa acgtcaacg tttagcttat atacgtcttt    2220
atagtggtgt tttacattta cgtgatagtg ttcgtgttag tgaaaagaa aagattaaag    2280 ttacagaaat gtatacttct attaacggtg aattatgcaa aattgaccgt gcatattcag   2340
gtgaaattgt aattttacaa aacgaatttc ttaaacttaa tagtgtactt ggtgacacaa   2400
aacttttacc acaacgtaag aaaattgaaa atccacaccc attacttcaa acaacagtag   2460
aaccaagcaa acctgaacaa cgtgaaatgc ttttagatgc tcttttagaa attagtgact   2520
ctgacccact tttacgttac tatgtagatt ctactactca tgaaattatt cttttctttcc   2580 ttggtaaagt tcaaatggaa gttatttctg cattattaca agaaaaatat catgttgaaa   2640
tcgaattaaa agaacctact gtaatttata tggaacgtcc attaaaaaat gctgaatata   2700
```

-continued

```
caattcatat tgaagttcca ccaaatccat tttgggcttc tattggtctt tctgtttctc      2760
cacttccact tggtagcgga atgcaatatg aaagtagcgt aagtttaggt tatcttaatc      2820
aaagtttcca aaacgcagtt atggaaggta ttcgttacgg ttgcgaacaa ggtttatacg      2880
gttggaatgt tacagactgc aaaatctgtt ttaagtatgg actttactat tcacctgtat      2940
caacacctgc tgactttcgt atgcttgcac caattgtttt agaacaagtt ttaaagaaag      3000
ctggaactga acttttagaa ccataccttt cttttaaaat ctatgcacca caagaatact      3060
taagtcgtgc ttataacgat gcacctaaat actgtgctaa tattgttgat actcaattaa      3120
agaacaacga agtaatttta agcggagaaa ttcctgcacg ttgtattcaa gaatatcgta      3180
gtgatttaac attttttcact aatggacgtt ctgtttgctt aactgaatta aaaggttatc      3240
```

```
atgttactac tggtgaacct gtatgccaac cacgtcgtcc taatagtcgt attgataaag      3300
ttcgttatat gttcaacaaa atcacataat aaaaaaaaaa accccgcccc tgacagggcg      3360 gggtttttt tttagttagt tagagatgtg tataagagac agctggccat ggaatagact      3420
ggatggaggc ggataaagtt gcaggaccac ttctgcgctc ggcccttccg gctggctggt      3480
ttattgctga taaatctgga gccggtgagc gtgggtctcg cggtatcatt gcagcactgg      3540
ggccagatgg taagccctcc cgtatcgtag ttatctacac gacggggagt caggcaacta      3600
tggatgaacg aaatagacag atcgctgaga taggtgcctc actgattaag cattggtaac      3660
tgtcagacca agtttactca tatatacttt agattgattt aaaacttcat ttttaattta      3720
aaaggatcta ggtgaagatc cttttttgata atctcatgac caaaatccct taacgtgagt      3780
tttcgttcca ctgagcgtca gaccccttaa taagatgatc ttcttgagat cgttttggtc      3840
tgcgcgtaat ctcttgctct gaaaacgaaa aaaccgcctt gcagggcggt ttttcgaagg      3900
ttctctgagc taccaactct ttgaaccgag gtaactggct tggaggagcg cagtcaccaa      3960
aacttgtcct ttcagtttag ccttaaccgg cgcatgactt caagactaac tcctctaaat      4020
caattaccag tggctgctgc cagtggtgct tttgcatgtc tttccgggtt ggactcaaga      4080
cgatagttac cggataaggc gcagcggtcg gactgaacgg ggggttcgtg catacagtcc      4140
agcttggagc gaactgccta cccggaactg agtgtcaggc gtggaatgag acaaacgcgg      4200
ccataacagc ggaatgacac cggtaaaccg aaaggcagga acaggagagc gcacgaggga      4260
gccgccaggg gaaacgcctg gtatctttat agtcctgtcg ggtttcgcca ccactgattt      4320
gagcgtcaga tttcgtgatg cttgtcaggg gggcggagcc tatggaaaaa cggctttgcc      4380
gcggccctct cacttccctg ttaagtatct tcctggcatc ttccaggaaa tctccgcccc      4440
gttcgtaagc catttccgct cgccgcagtc gaacgaccga gcgtagcgag tcagtgagcg      4500
aggaagcgga atatatcctg tatcacatat tctgctgacg caccggtgca gcctttttc       4560 tcctgccaca tgaagcactt cactgacacc ctcatcagtg ccaacatagt aagccagtat      4620
acactccgct agcgctgagg tctgcctcgt gaagaaggtg ttgctgactc ataccaggcc      4680
tgaatcgccc catcatccag ccagaaagtg agggagccac ggttgatgag agctttgttg      4740
taggtggacc agttggtgat tttgaacttt tgctttgcca cggaacggtc tgcgttgtcg      4800
ggaagatgcg tgatctgatc cttcaactca gcaaaagttc gatttattca acaaagccac      4860
gttgtgtctc aaaatctctg atgttacatt gcacaagata aaaatatatc atcatgaaca      4920
ataaaactgt ctgcttacat aaacagtaat acaaggggtg ttgcc                     4965
```

<210> SEQ ID NO 85
<211> LENGTH: 4977

<212> TYPE: DNA
<213> ORGANISM: Artificial Sequence
<220> FEATURE:
<223> OTHER INFORMATION: Synthetic Construct

<400> SEQUENCE: 85

```
cagctgtctc ttatacacat ctcacagcta acaccacgtc gtccctatct gctgccctag      60
gtctatgagt ggttgctgga taactttacg ggcatgcata aggctcgtat aatatattca     120
gggagaccac aacggtttcc ctctacaaat aattttgttt aactttgcct cacacaggaa     180
agtactagat ggagggagta aacgataatg aagagggttt ctttagtgct cgtttagaag     240
tacttttcca aggtccaatg gctagtagta aggatatataa caaagagttt atgcgtttta     300
aagttcacat ggaaggttca gtaaacggac atgaatttga aattgaggga aaggagagg     360
gtcgtccgta cgaaggtaca caaacagcaa agttaaaagt aacaaaagga ggacctttac     420
catttgcatg ggatattctt tctccacaat ttatgtatgg tagtaaagcg tatgttaaac     480
acccggcaga tataccagac tatttaaagt tgagttttcc ggaaggattc aaatgggaac     540
gtgttatgaa ttttgaagat ggtggtgttg ttacagttac tcaagatagt agcttacagg     600
atggtgaatt tatttacaaa gtaaaattac gtggtactaa cttcccgagc gatggtccag     660
taatgcaaaa gaaaactatg ggatgggagg ctagttctga acgtatgtat cctgaagacg     720
gtgctttaaa aggagaaatt aaacaacgtt gaaacttaa agatggtgga cactacgatg     780
cagaagttaa aactacatat aaagctaaaa agcctgttca gcttccgggt gcttataatg     840
tgaatataaa attagatatc acaagtcata cgaagatta tactattgtt gaacagtatg     900
aaagagcaga aggaagacat tctacaggag cagcctaacc aggcatcaaa taaaacgaaa     960
ggctcagtcg aaagactggg cctttcgttt tatctgttgt ttgtcggtga acgctctcta    1020
ctagagtcac actggctcac cttcgggtgg gcctttctgc gtttatagcc ggccagtcta    1080
catgtactct ttttgataaa aaattggaga ttcctttaca aatatgctct tacgtgctat    1140
tatttaagtg actatttaaa aggagttaat aaatatgcgg caaggtattc ttaaataaac    1200
tgtcaatttg atagcgggaa caaataatta gatgtccttt tttaggaggg cttagtttt    1260
tgtacccagt ttaagaatac ctttatcatg tgattctaaa gtatccagag aatatctgta    1320
tgctttgtat acctatggtt atgcataaaa atcccggtga taaaagtatt tatcactggg    1380
atttttatgc ccttttgggt ttttgaatgg aggaatacta gatgaaaatc ataaatatcg    1440
gtgtattagc tcacgttgat gcaggaaaaa caacattaac tgaatcactt ttatataact    1500
ctggtgcaat tactgaactt ggttcagtag ataaggtac tactcgtact gataatacat    1560
tattagaacg tcaacgtgga atcacaattc aaacaggtat cacatctttt caatgggaaa    1620
atacaaaagt aaatattata gatacacctg gacacatgga tttccttgca gaagtatacc    1680
gtagtctttc agtattagat ggtgctattt tacttatcag cgctaaagat ggagttcaag    1740
ctcaaactcg tatcttattt cacgcattac gtaaatggg tattccaaca attttcttta    1800
taaacaaaat tgaccaaaac ggaattgatt taagtacagt ttatcaagat atcaaagaaa    1860
aactttctgc tgaaatcgtt attaaacaaa aagttgaatt atacccaaac gtttgcgtaa    1920
caaattttac tgaatcagaa caatgggata cagttataga aggtaatgat gatttattag    1980
aaaaatacat gtcaggtaaa tcattagaag cattagaatt agaacaagaa gaaagtattc    2040
gtttccaaaa ctgttcttta ttccctttat accatggaag cgctaaaagt aacataggta    2100
ttgataactt aattgaagtt attactaaca aattttattc ttcaactcat cgtgggcctt    2160
```

```
ctgaattatg cggtaacgtt ttcaaaattg aatatacaaa aaaacgtcaa cgtttagctt    2220
atatacgtct ttatagtggt gttttacatt tacgtgatag tgttcgtgtt agtgaaaaag    2280
aaaagattaa agttacagaa atgtatactt ctattaacgg tgaattatgc aaaattgacc    2340
gtgcatattc aggtgaaatt gtaattttac aaaacgaatt tcttaaactt aatagtgtac    2400
ttggtgacac aaaacttta ccacaacgta agaaaattga aatccacac ccattacttc      2460
aaacaacagt agaaccaagc aaacctgaac aacgtgaaat gcttttagat gctcttttag    2520
aaattagtga ctctgaccca cttttacgtt actatgtaga ttctactact catgaaatta    2580
ttctttcttt ccttggtaaa gttcaaatgg aagttatttc tgcattatta caagaaaaat    2640
atcatgttga aatcgaatta aaagaaccta ctgtaattta tatggaacgt ccattaaaaa    2700
atgctgaata tacaattcat attgaagttc accaaatcc attttgggct tctattggtc     2760
tttctgtttc tccacttcca cttggtagcg gaatgcaata tgaaagtagc gtaagtttag    2820
gttatcttaa tcaaagtttc caaaacgcag ttatggaagg tattcgttac ggttgcgaac    2880
aaggtttata cggttggaat gttacagact gcaaaatctg ttttaagtat ggactttact    2940
attcacctgt atcaacacct gctgactttc gtatgcttgc accaattgtt ttagaacaag    3000
ttttaaagaa agctggaact gaactttag aaccatacct ttcttttaaa atctatgcac      3060
cacaagaata cttaagtcgt gcttataacg atgcacctaa atactgtgct aatattgttg    3120
atactcaatt aaagaacaac gaagtaattt taagcggaga aattcctgca cgttgtattc    3180
aagaatatcg tagtgattta acatttttca ctaatggacg ttctgtttgc ttaactgaat    3240
taaaaggtta tcatgttact actggtgaac ctgtatgcca accacgtcgt cctaatagtc    3300
gtattgataa agttcgttat atgttcaaca aaatcacata taaaaaaaa aaaccccgcc     3360
cctgacaggg cggggttttt ttttagtta gttagagatg tgtataagag acagctggcc     3420
atggaataga ctggatggag gcggataaag ttgcaggacc acttctgcgc tcggcccttc    3480
cggctggctg gttattgct gataaatctg gagccggtga gcgtgggtct cgcggtatca      3540
ttgcagcact ggggccagat ggtaagccct cccgtatcgt agttatctac acgacgggga    3600
gtcaggcaac tatggatgaa cgaaatagac agatcgctga gataggtgcc tcactgatta    3660
agcattggta actgtcagac caagtttact catatatact ttagattgat ttaaaacttc    3720
atttttaatt taaaggatc taggtgaaga tccttttga taatctcatg accaaaatcc       3780
cttaacgtga gttttcgttc cactgagcgt cagaccccct aataagatga tcttcttgag    3840
atcgttttgg tctgcgcgta atctcttgct ctgaaaacga aaaaccgcc ttgcagggcg      3900
gtttttcgaa ggttctctga ctaccaact cttttgaaccg aggtaactgg cttggaggag     3960
cgcagtcacc aaaacttgtc ctttcagttt agccttaacc ggcgcatgac ttcaagacta    4020
actcctctaa atcaattacc agtggctgct gccagtggtg cttttgcatg tctttccggg    4080
ttggactcaa gacgatagtt accggataag gcgcagcggt cggactgaac ggggggttcg    4140
tgcatacagt ccagcttgga gcgaactgcc tacccggaac tgagtgtcag gcgtggaatg    4200
agacaaacgc ggccataaca gcggaatgac accggtaaac cgaaaggcag gaacaggaga    4260
gcgcacgagg gagccgccag gggaaacgcc tggtatcttt atagtcctgt cgggtttcgc    4320
caccactgat ttgagcgtca gatttcgtga tgcttgtcag ggggcggag cctatggaaa     4380
aacggctttg ccgcggccct ctcacttccc tgttaagtat cttcctggca tcttccagga    4440
aatctccgcc ccgttcgtaa gccatttccg ctcgccgcag tcgaacgacc gagcgtagcg    4500
agtcagtgag cgaggaagcg gaatatatcc tgtatcacat attctgctga cgcaccggtg    4560
```

```
cagccttttt tctcctgcca catgaagcac ttcactgaca ccctcatcag tgccaacata    4620
gtaagccagt atacactccg ctagcgctga ggtctgcctc gtgaagaagg tgttgctgac    4680
tcataccagg cctgaatcgc cccatcatcc agccagaaag tgagggagcc acggttgatg    4740
agagctttgt tgtaggtgga ccagttggtg attttgaact tttgctttgc cacggaacgg    4800
tctgcgttgt cgggaagatg cgtgatctga tccttcaact cagcaaaagt tcgatttatt    4860
caacaaagcc acgttgtgtc tcaaaatctc tgatgttaca ttgcacaaga taaaaatata    4920
tcatcatgaa caataaaact gtctgcttac ataaacagta atacaagggg tgttgcc       4977
```

<210> SEQ ID NO 86
<211> LENGTH: 4992
<212> TYPE: DNA
<213> ORGANISM: Artificial Sequence
<220> FEATURE:
<223> OTHER INFORMATION: Synthetic Construct

<400> SEQUENCE: 86

```
cagctgtctc ttatacacat ctcacagcta acaccacgtc gtccctatct gctgccctag      60
gtctatgagt ggttgctgga taactttacg ggcatgcata aggctcgtat aatatattca     120
gggagaccac aacggtttcc ctctacaaat aattttgttt aacttttcac acaggaaagt     180
actagatgga acaaaaactt atttcagagg aagacttaga tcgtgtatat attcacccttt    240 ttcatttatt agaagtactt ttccaaggtc caatggctag tagtgaggat ataatcaaag     300
agtttatgcg ttttaaagtt cacatggaag gttcagtaaa cggacatgaa tttgaaattg     360
agggagaagg agagggtcgt ccgtacgaag gtacacaaac agcaaagtta aaagtaacaa     420
aaggaggacc tttaccattt gcatgggata ttctttctcc acaatttatg tatggtagta     480
aagcgtatgt taaacacccg gcagatatac cagactattt aaagttgagt tttccggaag     540
gattcaaatg ggaacgtgtt atgaattttg aagatggtgg tgttgttaca gttactcaag     600
atagtagctt acaggatggt gaatttattt acaaagtaaa attacgtggt actaacttcc     660
cgagcgatgg tccagtaatg caaaagaaaa ctatgggatg ggaggctagt tctgaacgta     720
tgtatcctga agacggtgct ttaaaaggag aaattaaaca acgtttgaaa cttaaagatg     780
gtggacacta cgatgcagaa gttaaaacta catataaagc taaaaagcct gttcagcttc     840
cgggtgctta taatgtgaat ataaaattag atatcacaag tcataacgaa gattatacta     900
ttgttgaaca gtatgaaaga gcagaaggaa gacattctac aggagcagcc taaccaggca     960
tcaaataaaa cgaaaggctc agtcgaaaga ctgggccttt cgttttatct gttgtttgtc    1020
ggtgaacgct ctctactaga gtcacactgg ctcaccttcg ggtgggcctt tctgcgttta    1080
tagccggcca gtctacatgt actcttttg ataaaaaatt ggagattcct ttacaaatat     1140
gctcttacgt gctattattt aagtgactat ttaaaggag ttaataaata tgcggcaagg     1200
tattcttaaa taaactgtca atttgatagc gggaacaaat aattagatgt cctttttag     1260 gagggcttag ttttttgtac ccagtttaag aatacccttta tcatgtgatt ctaaagtatc    1320
cagagaatat ctgtatgctt tgtataccta tggttatgca taaaaatccc ggtgataaaa    1380
gtatttatca ctgggatttt tatgcccttt tgggtttttg aatggaggaa actagatgaa    1440
aaatcataaa tatcggtgta ttagctcacg ttgatgcagg aaaaacaaca ttaactgaat    1500
cacttttata taactctggt gcaattactg aacttggttc agtagataaa ggtactactc    1560
gtactgataa tacattatta gaacgtcaac gtggaatcac aattcaaaca ggtatcacat    1620
```

```
cttttcaatg ggaaaataca aaagtaaata ttatagatac acctggacac atggatttcc    1680
ttgcagaagt ataccgtagt ctttcagtat tagatggtgc tattttactt atcagcgcta    1740
aagatggagt tcaagctcaa actcgtatct tatttcacgc attacgtaaa atgggtattc    1800
caacaatttt ctttataaac aaaattgacc aaaacggaat tgatttaagt acagtttatc    1860
aagatatcaa agaaaaactt tctgctgaaa tcgttattaa acaaaaagtt gaattatacc    1920
caaacgtttg cgtaacaaat tttactgaat cagaacaatg ggatacagtt atagaaggta    1980
atgatgattt attagaaaaa tacatgtcag gtaaatcatt agaagcatta gaattagaac    2040
aagaagaaag tattcgtttc caaaactgtt ctttattccc tttataccat ggaagcgcta    2100
aaagtaacat aggtattgat aacttaattg aagttattac taacaaattt tattcttcaa    2160
ctcatcgtgg gcctctgaa ttatgcggta acgttttcaa aattgaatat acaaaaaaac    2220
gtcaacgttt agcttatata cgtctttata gtggtgtttt acatttacgt gatagtgttc    2280
gtgttagtga aaagaaaag attaaagtta cagaaatgta tacttctatt aacggtgaat    2340
tatgcaaaat tgaccgtgca tattcaggtg aaattgtaat tttacaaaac gaatttctta    2400
aacttaatag tgtacttggt gacacaaaac ttttaccaca acgtaagaaa attgaaaatc    2460
cacacccatt acttcaaaca acagtagaac caagcaaacc tgaacaacgt gaaatgcttt    2520
tagatgctct tttagaaatt agtgactctg acccactttt acgttactat gtagattcta    2580
ctactcatga aattattctt tcttttcctt gtaaagttca aatggaagtt atttctgcat    2640
tattacaaga aaatatcat gttgaaatcg aattaaaaga acctactgta atttatatgg    2700
aacgtccatt aaaaatgct gaatatacaa ttcatattga agttccacca aatccatttt    2760
gggcttctat tggtctttct gtttctccac ttccacttgg tagcggaatg caatatgaaa    2820
gtagcgtaag tttaggttat cttaatcaaa gtttccaaaa cgcagtttatg gaaggtattc    2880 gttacggttg cgaacaaggt ttatacggtt ggaatgttac agactgcaaa atctgttta    2940 agtatggact ttactattca cctgtatcaa cacctgctga ctttcgtatg cttgcaccaa    3000
ttgttttaga acaagtttta aagaaagctg gaactgaact tttagaacca tacctttctt    3060
ttaaaatcta tgcaccacaa gaatacttaa gtcgtgctta taacgatgca cctaaatact    3120
gtgctaatat tgttgatact caattaaaga acaacgaagt aattttaagc ggagaaattc    3180
ctgcacgttg tattcaagaa tatcgtagtg atttaacatt tttcactaat ggacgttctg    3240
tttgcttaac tgaattaaaa ggttatcatg ttactactgg tgaacctgta tgccaaccac    3300
gtcgtcctaa tagtcgtatt gataaagttc gttatatgtt caacaaaatc acataataaa    3360
aaaaaaaacc ccgcccctga cagggcgggg tttttttttt agttagttag agatgtgtat    3420
aagagacagc tggccatgga atagactgga tggaggcgga taaagttgca ggaccacttc    3480
tgcgctcggc ccttccggct ggctggttta ttgctgataa atctggagcc ggtgagcgtg    3540
ggtctcgcgg tatcattgca gcactggggc cagatggtaa gccctcccgt atcgtagtta    3600
tctacacgac ggggagtcag gcaactatgg atgaacgaaa tagacagatc gctgagatag    3660
gtgcctcact gattaagcat tggtaactgt cagaccaagt ttactcatat atactttaga    3720
ttgatttaaa acttcatttt taatttaaaa ggatctaggt gaagatcctt tttgataatc    3780
tcatgaccaa aatcccttaa cgtgagtttt cgttccactg agcgtcagac cccttaataa    3840
gatgatcttc ttgagatcgt tttggtctgc gcgtaatctc ttgctctgaa aacgaaaaaa    3900
ccgccttgca gggcggtttt tcgaaggttc tctgagctac caactctttg aaccgaggta    3960
actggcttgg aggagcgcag tcaccaaaac ttgtcctttc agtttagcct taaccggcgc    4020
```

```
atgacttcaa gactaactcc tctaaatcaa ttaccagtgg ctgctgccag tggtgctttt      4080
gcatgtcttt ccgggttgga ctcaagacga tagttaccgg ataaggcgca gcggtcggac      4140
tgaacggggg gttcgtgcat acagtccagc ttggagcgaa ctgcctaccc ggaactgagt      4200
gtcaggcgtg aatgagaca aacgcggcca taacagcgga atgacaccgg taaaccgaaa       4260
ggcaggaaca ggagagcgca cgagggagcc gccaggggaa acgcctggta tctttatagt      4320
cctgtcgggt ttcgccacca ctgatttgag cgtcagattt cgtgatgctt gtcagggggg      4380
cggagcctat ggaaaaacgg ctttgccgcg ccctctcac ttccctgtta agtatcttcc       4440
tggcatcttc caggaaatct ccgccccgtt cgtaagccat ttccgctcgc cgcagtcgaa      4500
cgaccgagcg tagcgagtca gtgagcgagg aagcggaata tatcctgtat cacatattct      4560
gctgacgcac cggtgcagcc tttttctcc tgccacatga agcacttcac tgacaccctc       4620
atcagtgcca acatagtaag ccagtataca ctccgctagc gctgaggtct gcctcgtgaa      4680
gaaggtgttg ctgactcata ccaggcctga atcgccccat catccagcca gaaagtgagg      4740
gagccacggt tgatgagagc tttgttgtag gtggaccagt tggtgatttt gaacttttgc      4800
tttgccacgg aacggtctgc gttgtcggga agatgcgtga tctgatcctt caactcagca      4860
aaagttcgat ttattcaaca aagccacgtt gtgtctcaaa atctctgatg ttacattgca      4920
caagataaaa atatatcatc atgaacaata aaactgtctg cttacataaa cagtaataca      4980
aggggtgttg cc                                                          4992

<210> SEQ ID NO 87
<211> LENGTH: 4908
<212> TYPE: DNA
<213> ORGANISM: Artificial Sequence
<220> FEATURE:
<223> OTHER INFORMATION: Synthetic Construct

<400> SEQUENCE: 87
cagctgtctc ttatacacat ctcacagcta acaccacgtc gtccctatct gctgccctag        60
gtctatgagt ggttgctgga taactttacg ggcatgcata aggctcgtat aatatattca       120
gggagaccac aacggtttcc ctctacaaat aattttgttt aactttgccc gcgctctccc       180
ccaccaaccc caatttcaca caggaaagta ctagatggct agtagtgagg atataatcaa       240
agagtttatg cgttttaaag ttcacatgga aggttcagta acggacatg aatttgaaat        300 tgagggagaa ggagagggtc gtccgtacga aggtacacaa acagcaaagt taaaagtaac       360
aaaaggagga cctttaccat tgcatggga tattctttct ccacaattta tgtatggtag       420
taaagcgtat gttaaacacc cggcagatat accagactat ttaaagttga gttttccgga      480
aggattcaaa tgggaacgtg ttatgaattt tgaagatggt ggtgttgtta cagttactca      540
agatagtagc ttacaggatg gtgaatttat ttacaaagta aaattacgtg gtactaactt      600
cccgagcgat ggtccagtaa tgcaaaagaa aactatggga tgggaggcta gttctgaacg      660
tatgtatcct gaagacggtg ctttaaaagg agaaattaaa caacgtttga acttaaaga       720 tggtggacac tacgatgcag aagttaaaac tacatataaa gctaaaaagc ctgttcagct      780
tccgggtgct tataatgtga atataaaatt agatatcaca agtcataacg aagattatac      840
tattgttgaa cagtatgaaa gagcagaagg aagacattct acaggagcag ccttagaagt      900
acttttccaa ggtccacata gtgatgctgt atttacagat aacactcgtt aaagagaata      960
taaaaagcca gattattaat ccggcttttt tattatttgc cggccagtct acatgtactc     1020
```

```
tttttgataa aaaattggag attccttac aaatatgctc ttacgtgcta ttatttaagt    1080
gactatttaa aaggagttaa taaatatgcg gcaaggtatt cttaaataaa ctgtcaattt    1140
gatagcggga acaaataatt agatgtcctt ttttaggagg gcttagtttt ttgtacccag    1200
tttaagaata cctttatcat gtgattctaa agtatccaga gaatatctgt atgctttgta    1260
tacctatggt tatgcataaa aatcccggtg ataaaagtat ttatcactgg gattttatg     1320 cccttttggg tttttgaatg gaggaatact agatgaaaat cataaatatc ggtgtattag    1380
ctcacgttga tgcaggaaaa acaacattaa ctgaatcact tttatataac tctggtgcaa    1440
ttactgaact tggttcagta gataaaggta ctactcgtac tgataataca ttattagaac    1500
gtcaacgtgg aatcacaatt caaacaggta tcacatcttt tcaatgggaa aatacaaaag    1560
taaatattat agatacacct ggacacatgg atttccttgc agaagtatac cgtagtcttt    1620
cagtattaga tggtgctatt ttacttatca gcgctaaaga tggagttcaa gctcaaactc    1680
gtatcttatt tcacgcatta cgtaaaatgg gtattccaac aatttccttt ataaacaaaa    1740
ttgaccaaaa cggaattgat ttaagtacag tttatcaaga tatcaaagaa aaactttctg    1800
ctgaaatcgt tattaaacaa aaagttgaat tatacccaaa cgtttgcgta acaaatttta    1860
ctgaatcaga acaatgggat acagttatag aaggtaatga tgatttatta gaaaaataca    1920
tgtcaggtaa atcattagaa gcattagaat tagaacaaga agaaagtatt cgtttccaaa    1980
actgttcttt attcccttta taccatgaa gcgctaaaag taacataggt attgataact    2040
taattgaagt tattactaac aaatttttatt cttcaactca tcgtgggcct tctgaattat    2100
gcggtaacgt tttcaaaatt gaatatacaa aaaaacgtca acgtttagct tatatacgtc    2160
tttatagtgg tgttttacat ttacgtgata gtgttcgtgt tagtgaaaaa gaaaagatta    2220
aagttacaga aatgtatact tctattaacg gtgaattatg caaaattgac cgtgcatatt    2280
caggtgaaat tgtaattta caaaacgaat tcttaaaact taatagtgta cttggtgaca    2340
caaaactttt accacaacgt aagaaaattg aaaatccaca cccattactt caaacaacag    2400
tagaaccaag caaacctgaa caacgtgaaa tgcttttaga tgctcttta gaaattagtg    2460 actctgaccc acttttacgt tactatgtag attctactac tcatgaaatt attctttctt    2520
tccttggtaa agttcaaatg gaagttattt ctgcattatt acaagaaaaa tatcatgttg    2580
aaatcgaatt aaaagaacct actgtaattt atatggaacg tccattaaaa aatgctgaat    2640
atacaattca tattgaagtt ccaccaaatc cattttgggc ttctattggt ctttctgttt    2700
ctccacttcc acttggtagc ggaatgcaat atgaaagtag cgtaagttta ggttatctta    2760
atcaaagttt ccaaaacgca gttatggaag gtattcgtta cggttgcgaa caaggtttat    2820
acggttggaa tgttacagac tgcaaaatct gttttaagta tggactttac tattcacctg    2880
tatcaacacc tgctgacttt cgtatgcttg caccaattgt tttagaacaa gttttaaaga    2940
aagctggaac tgaacttta gaaccatacc tttctttaa aatctatgca ccacaagaat    3000
acttaagtcg tgcttataac gatgcaccta aatactgtgc taatattgtt gatactcaat    3060
taaagaacaa cgaagtaatt ttaagcggag aaattcctgc acgttgtatt caagaatatc    3120
gtagtgattt aacattttc actaatggac gttctgtttg cttaactgaa ttaaaaggtt    3180
atcatgttac tactggtgaa cctgtatgcc aaccacgtcg tcctaatagt cgtattgata    3240
aagttcgtta tatgttcaac aaaatcacat aataaaaaaa aaacccgc ccctgacagg     3300 gcggggtttt tttttagtt agttagagat gtgtataaga gacagctggc catggaatag    3360
actggatgga ggcggataaa gttgcaggac cacttctgcg ctcggccctt ccggctggct    3420
```

```
ggtttattgc tgataaatct ggagccggtg agcgtgggtc tcgcggtatc attgcagcac    3480
tggggccaga tggtaagccc tcccgtatcg tagttatcta cacgacgggg agtcaggcaa    3540
ctatggatga acgaaataga cagatcgctg agataggtgc ctcactgatt aagcattggt    3600
aactgtcaga ccaagtttac tcatatatac tttagattga tttaaaactt cattttaat     3660 ttaaaaggat ctaggtgaag atcctttttg ataatctcat gaccaaaatc ccttaacgtg    3720
agttttcgtt ccactgagcg tcagacccct taataagatg atcttcttga tcgttttg     3780 gtctgcgcgt aatctcttgc tctgaaaacg aaaaaaccgc cttgcagggc ggttttcga    3840 aggttctctg agctaccaac tctttgaacc gaggtaactg gcttggagga gcgcagtcac    3900
caaaacttgt cctttcagtt tagccttaac cggcgcatga cttcaagact aactcctcta    3960
aatcaattac cagtggctgc tgccagtggt gcttttgcat gtctttccgg gttggactca    4020
agacgatagt taccggataa ggcgcagcgg tcggactgaa cggggggttc gtgcatacag    4080
tccagcttgg agcgaactgc ctacccggaa ctgagtgtca ggcgtggaat gagacaaacg    4140
cggccataac agcggaatga caccggtaaa ccgaaaggca ggaacaggag agcgcacgag    4200
ggagccgcca ggggaaacgc ctggtatctt tatagtcctg tcgggtttcg ccaccactga    4260
tttgagcgtc agatttcgtg atgcttgtca gggggcgga gcctatggaa aaacggcttt    4320
gccgcggccc tctcacttcc ctgttaagta tcttcctggc atcttccagg aaatctccgc    4380
cccgttcgta agccatttcc gctcgccgca gtcgaacgac cgagcgtagc gagtcagtga    4440
gcgaggaagc ggaatatatc ctgtatcaca tattctgctg acgcaccggt gcagcctttt    4500
ttctcctgcc acatgaagca cttcactgac accctcatca gtgccaacat agtaagccag    4560
tatacactcc gctagcgctg aggtctgcct cgtgaagaag gtgttgctga ctcataccag    4620
gcctgaatcg ccccatcatc cagccagaaa gtgagggagc cacggttgat gagagctttg    4680
ttgtaggtgg accagttggt gattttgaac ttttgctttg ccacgaacg gtctgcgttg    4740 tcgggaagat gcgtgatctg atccttcaac tcagcaaaag ttcgatttat tcaacaaagc    4800
cacgttgtgt ctcaaaatct ctgatgttac attgcacaag ataaaatat atcatcatga    4860 acaataaaac tgtctgctta cataaacagt aatacaaggg gtgttgcc                4908
```

<210> SEQ ID NO 88
<211> LENGTH: 4896
<212> TYPE: DNA
<213> ORGANISM: Artificial Sequence
<220> FEATURE:
<223> OTHER INFORMATION: Synthetic Construct

<400> SEQUENCE: 88

```
cagctgtctc ttatacacat ctcacagcta acaccacgtc gtccctatct gctgccctag     60
gtctatgagt ggttgctgga taactttacg ggcatgcata aggctcgtat aatatattca    120
gggagaccac aacggtttcc ctctacaaat aattttgttt aactttgccc gcgctctccc    180
ccaccaaccc caatttcaca caggaaagta ctagatggct agtagtgagg atataatcaa    240
agagtttatg cgttttaaag ttcacatgga aggttcagta acggacatg aatttgaaat    300 tgagggagaa ggagagggtc gtccgtacga aggtacacaa acagcaaagt taaaagtaac    360
aaaaggagga cctttaccat ttgcatggga tattctttct ccacaattta tgtatggtag    420
taaagcgtat gttaaacacc cggcagatat accagactt ttaaagttga gttttccgga    480
aggattcaaa tgggaacgtg ttatgaattt tgaagatggt ggtgttgtta cagttactca    540
```

```
agatagtagc ttacaggatg gtgaatttat ttacaaagta aaattacgtg gtactaactt    600
cccgagcgat ggtccagtaa tgcaaaagaa aactatggga tgggaggcta gttctgaacg    660
tatgtatcct gaagacggtg ctttaaaagg agaaattaaa caacgtttga aacttaaaga    720
tggtggacac tacgatgcag aagttaaaac tacatataaa gctaaaaagc ctgttcagct    780
tccgggtgct tataatgtga atataaaatt agatatcaca agtcataacg aagattatac    840
tattgttgaa cagtatgaaa gagcagaagg aagacattct acaggagcag ccttagaagt    900
acttttccaa ggtccacgtc cacctggatt tagtccttaa agagaatata aaaagccaga    960
ttattaatcc ggcttttta ttatttgccg gccagtctac atgtactctt tttgataaaa     1020
aattggagat tcctttacaa atatgctctt acgtgctatt atttaagtga ctatttaaaa    1080
ggagttaata aatatgcggc aaggtattct taaataaact gtcaatttga tagcgggaac    1140
aaataattag atgtcctttt ttaggagggc ttagtttttt gtacccagtt taagaatacc    1200
tttatcatgt gattctaaag tatccagaga atatctgtat gctttgtata cctatggtta    1260
tgcataaaaa tcccggtgat aaaagtattt atcactggga tttttatgcc cttttgggtt    1320
tttgaatgga ggaatactag atgaaaatca taaatatcgg tgtattagct cacgttgatg    1380
caggaaaaac aacattaact gaatcacttt tatataactc tggtgcaatt actgaacttg    1440
gttcagtaga taaggtact actcgtactg ataatacatt attagaacgt caacgtggaa     1500
tcacaattca aacaggtatc acatcttttc aatgggaaaa tacaaaagta atattatag     1560 atacacctgg acacatggat ttccttgcag aagtataccg tagtctttca gtattagatg    1620
gtgctatttt acttatcagc gctaaagatg gagttcaagc tcaaactcgt atcttatttc    1680
acgcattacg taaaatgggt attccaacaa ttttctttat aaacaaaatt gaccaaaacg    1740
gaattgattt aagtacagtt tatcaagata tcaagaaaaa actttctgct gaaatcgtta    1800
ttaaacaaaa agttgaatta tacccaaacg tttgcgtaac aaattttact gaatcagaac    1860
aatgggatac agttatagaa ggtaatgatg atttattaga aaaatacatg tcaggtaaat    1920
cattagaagc attagaatta gaacaagaag aaagtattcg tttccaaaac tgttctttat    1980 tcccttata ccatggaagc gctaaaagta acataggtat tgataactta attgaagtta     2040
ttactaacaa attttattct tcaactcatc gtgggccttc tgaattatgc ggtaacgttt    2100
tcaaaattga atatacaaaa aaacgtcaac gtttagctta tacgtctctt tatagtggtg    2160
ttttacattt acgtgatagt gttcgtgtta gtgaaaaaga aaagattaaa gttacagaaa    2220
tgtatacttc tattaacggt gaattatgca aaattgaccg tgcatattca ggtgaaattg    2280
taattttaca aaacgaattt cttaaactta atagtgtact tggtgacaca aaacttttac    2340
cacaacgtaa gaaaattgaa aatccacacc cattacttca aacaacagta gaaccaagca    2400
aacctgaaca acgtgaaatg cttttagatg ctctttaga aattagtgac tctgacccac     2460
ttttacgtta ctatgtagat tctactactc atgaaattat tctttctttc cttggtaaag    2520
ttcaaatgga agttatttct gcattattac aagaaaaata tcatgttgaa atcgaattaa    2580
aagaacctac tgtaatttat atggaacgtc cattaaaaaa tgctgaatat acaattcata    2640
ttgaagttcc accaaatcca ttttgggctt ctattggtct ttctgtttct ccacttccac    2700
ttggtagcgg aatgcaatat gaaagtagcg taagtttagg ttatcttaat caaagtttcc    2760
aaaacgcagt tatggaaggt attcgttacg gttgcgaaca aggtttatac ggttggaatg    2820
ttacagactg caaaatctgt tttaagtatg gactttacta ttcacctgta tcaacacctg    2880
ctgactttcg tatgcttgca ccaattgttt tagaacaagt tttaaagaaa gctggaactg    2940
```

```
aacttttaga accatacctt tcttttaaaa tctatgcacc acaagaatac ttaagtcgtg    3000
cttataacga tgcacctaaa tactgtgcta atattgttga tactcaatta agaacaacg    3060 aagtaatttt aagcggagaa attcctgcac gttgtattca agaatatcgt agtgatttaa    3120 cattttcac taatggacgt tctgtttgct taactgaatt aaaaggttat catgttacta    3180
ctggtgaacc tgtatgccaa ccacgtcgtc ctaatagtcg tattgataaa gttcgttata    3240
tgttcaacaa aatcacataa taaaaaaaaa aaccccgccc ctgacagggc ggggttttt    3300 ttttagttag ttagagatgt gtataagaga cagctggcca tggaatagac tggatggagg    3360
cggataaagt tgcaggacca cttctgcgct cggcccttcc ggctggctgg tttattgctg    3420
ataaatctgg agccggtgag cgtgggtctc gcggtatcat tgcagcactg gggccagatg    3480
gtaagccctc ccgtatcgta gttatctaca cgacggggag tcaggcaact atggatgaac    3540
gaaatagaca gatcgctgag ataggtgcct cactgattaa gcattggtaa ctgtcagacc    3600
aagtttactc atatatactt tagattgatt taaaacttca ttttaatttt aaaaggatct    3660
aggtgaagat cctttttgat aatctcatga ccaaaatccc ttaacgtgag ttttcgttcc    3720
actgagcgtc agacccctta ataagatgat cttcttgaga tcgttttggt ctgcgcgtaa    3780
tctcttgctc tgaaaacgaa aaaccgcct tgcagggcgg tttttcgaag gttctctgag    3840
ctaccaactc tttgaaccga ggtaactggc ttggaggagc gcagtcacca aaacttgtcc    3900
tttcagttta gccttaaccg cgcatgact tcaagactaa ctcctctaaa tcaattacca    3960
gtggctgctg ccagtggtgc ttttgcatgt ctttccgggt tggactcaag acgatagtta    4020
ccggataagg cgcagcggtc ggactgaacg ggggggttcgt gcatacagtc cagcttggag    4080
cgaactgcct acccggaact gagtgtcagg cgtggaatga cgaaacgcg gccataacag    4140 cggaatgaca ccggtaaacc gaaaggcagg aacaggagag cgcacgaggg agccgccagg    4200
ggaaacgcct ggtatcttta tagtcctgtc gggtttcgcc accactgatt tgagcgtcag    4260
atttcgtgat gcttgtcagg ggggcggagc ctatggaaaa acggctttgc cgcggccctc    4320
tcacttccct gttaagtatc ttcctggcat cttccaggaa atctccgccc cgttcgtaag    4380
ccatttccgc tcgccgcagt cgaacgaccg agcgtagcga gtcagtgagc gaggaagcgg    4440
aatatatcct gtatcacata ttctgctgac gcaccggtgc agcctttttt ctcctgccac    4500
atgaagcact tcactgacac cctcatcagt gccaacatag taagccagta tacactccgc    4560
tagcgctgag gtctgcctcg tgaagaaggt gttgctgact cataccaggc ctgaatcgcc    4620
ccatcatcca gccagaaagt gagggagcca cggttgatga gagctttgtt gtaggtggac    4680
cagttggtga ttttgaactt ttgctttgcc acggaacggt ctgcgttgtc gggaagatgc    4740
gtgatctgat ccttcaactc agcaaaagtt cgatttattc aacaaagcca cgttgtgtct    4800
caaaatctct gatgttacat tgcacaagat aaaaatatat catcatgaac aataaaactg    4860
tctgcttaca taacagtaa tacaagggt gttgcc                              4896
```

<210> SEQ ID NO 89
<211> LENGTH: 4890
<212> TYPE: DNA
<213> ORGANISM: Artificial Sequence
<220> FEATURE:
<223> OTHER INFORMATION: Synthetic Construct

<400> SEQUENCE: 89

```
cagctgtctc ttatacacat ctcacagcta acaccacgtc gtccctatct gctgccctag    60
```

```
gtctatgagt ggttgctgga taactttacg ggcatgcata aggctcgtat aatatattca    120
gggagaccac aacggtttcc ctctacaaat aattttgttt aactttgccc gcgctctccc    180
ccaccaaccc caatttcaca caggaaagta ctagatggct agtagtgagg ataatcaa      240 agagtttatg cgttttaaag ttcacatgga aggttcagta acggacatg aatttgaaat     300 tgagggagaa ggagagggtc gtccgtacga aggtacacaa acagcaaagt taaaagtaac    360
aaaaggagga cctttaccat ttgcatggga tattctttct ccacaattta tgtatggtag    420
taaagcgtat gttaaacacc cggcagatat accagactat ttaaagttga gttttccgga    480
aggattcaaa tgggaacgtg ttatgaattt tgaagatggt ggtgttgtta cagttactca    540
agatagtagc ttacaggatg gtgaatttat ttacaaagta aaattacgtg gtactaactt    600
cccgagcgat ggtccagtaa tgcaaaagaa actatggga tgggaggcta gttctgaacg     660
tatgtatcct gaagacggtg ctttaaaagg agaaattaaa caacgtttga aacttaaaga    720
tggtggacac tacgatgcag aagttaaaac tacatataaa gctaaaaagc ctgttcagct    780
tccgggtgct tataatgtga atataaatt agatatcaca agtcataacg aagattatac     840
tattgttgaa cagtatgaaa gagcagaagg aagacattct acaggagcag ccttagaagt    900
acttttccaa ggtccatacg gaggttttct ttaaagagaa tataaaaagc cagattatta    960
atccggcttt tttattattt gccggccagt ctacatgtac tcttttttgat aaaaaattgg   1020 agattccttt acaaatatgc tcttacgtgc tattatttaa gtgactattt aaaaggagtt    1080
aataaatatg cggcaaggta ttcttaaata aactgtcaat ttgatagcgg gaacaaataa    1140
ttagatgtcc ttttttagga gggcttagtt ttttgtaccc agtttaagaa taccttttatc   1200 atgtgattct aaagtatcca gagaatatct gtatgctttg tataccatg gttatgcata    1260 aaaatcccgg tgataaaagt atttatcact gggattttta tgcccttttg ggttttgaa    1320 tggaggaata ctagatgaaa atcataaata tcggtgtatt agctcacgtt gatgcaggaa    1380
aaacaacatt aactgaatca cttttatata actctggtgc aattactgaa cttggttcag    1440
tagataaagg tactactcgt actgataata cattattaga acgtcaacgt ggaatcacaa    1500
ttcaaacagg tatcacatct tttcaatggg aaaatacaaa agtaaatatt atagatacac    1560
ctggacacat ggatttcctt gcagaagtat accgtagtct ttcagtatta gatggtgcta    1620
ttttacttat cagcgctaaa gatggagttc aagctcaaac tcgtatctta tttcacgcat    1680
tacgtaaaat gggtattcca acaatttttct ttataaacaa aattgaccaa aacggaattg   1740
atttaagtac agtttatcaa gatatcaaag aaaaactttc tgctgaaatc gttattaaac    1800
aaaaagttga attataccca aacgtttgcg taacaaattt tactgaatca gaacaatggg    1860
atacagttat agaaggtaat gatgatttat tagaaaaata catgtcaggt aaatcattag    1920
aagcattaga attagaacaa gaagaaagta ttcgtttcca aaactgttct ttattccctt    1980
tataccatgg aagcgctaaa agtaacatag gtattgataa cttaattgaa gttattacta    2040
acaaatttta ttcttcaact catcgtgggc cttctgaatt atgcggtaac gttttcaaaa    2100
ttgaatatac aaaaaaacgt caacgtttag cttatatacg tctttatagt ggtgttttac    2160
atttacgtga tagtgttcgt gttagtgaaa aagaaaagat taaagttaca gaaatgtata    2220
cttctattaa cggtgaatta tgcaaaattg accgtgcata ttcaggtgaa attgtaattt    2280
tacaaaacga atttcttaaa cttaatagtg tacttggtga cacaaaactt ttaccacaac    2340
gtaagaaaat tgaaaatcca cacccattac ttcaaacaac agtagaacca agcaaacctg    2400
aacaacgtga aatgctttta gatgctcttt tagaaattag tgactctgac ccactttttac   2460
```

```
gttactatgt agattctact actcatgaaa ttattctttc tttccttggt aaagttcaaa    2520
tggaagttat ttctgcatta ttacaagaaa aatatcatgt tgaaatcgaa ttaaaagaac    2580
ctactgtaat ttatatggaa cgtccattaa aaaatgctga atatacaatt catattgaag    2640
ttccaccaaa tccattttgg gcttctattg gtctttctgt ttctccactt ccacttggta    2700
gcggaatgca atatgaaagt agcgtaagtt taggttatct taatcaaagt ttccaaaacg    2760
cagttatgga aggtattcgt tacggttgcg aacaaggttt atacggttgg aatgttacag    2820
actgcaaaat ctgttttaag tatggacttt actattcacc tgtatcaaca cctgctgact    2880
ttcgtatgct tgcaccaatt gttttagaac aagttttaaa gaaagctgga actgaacttt    2940
tagaaccata cctttctttt aaaatctatg caccacaaga atacttaagt cgtgcttata    3000
acgatgcacc taaatactgt gctaatattg ttgatactca attaaagaac aacgaagtaa    3060
tttttaagcgg agaaattcct gcacgttgta ttcaagaata tcgtagtgat ttaacatttt    3120
tcactaatgg acgttctgtt tgcttaactg aattaaaagg ttatcatgtt actactggtg    3180
aacctgtatg ccaaccacgt cgtcctaata gtcgtattga taaagttcgt tatatgttca    3240
acaaaatcac ataataaaaa aaaaaacccc gcccctgaca gggcggggtt ttttttttag    3300
ttagttagag atgtgtataa gagacagctg gccatggaat agactggatg gaggcggata    3360
aagttgcagg accacttctg cgctcggccc ttccggctgg ctggtttatt gctgataaat    3420
ctggagccgg tgagcgtggg tctcgcggta tcattgcagc actggggcca gatggtaagc    3480
cctcccgtat cgtagttatc tacacgacgg ggagtcaggc aactatggat gaacgaaata    3540
gacagatcgc tgagataggt gcctcactga ttaagcattg gtaactgtca gaccaagttt    3600
actcatatat actttagatt gatttaaaac ttcatttta atttaaaagg atctaggtga    3660
agatcctttt tgataatctc atgaccaaaa tcccttaacg tgagttttcg ttccactgag    3720
cgtcagaccc cttaataaga tgatcttctt gagatcgttt tggtctgcgc gtaatctctt    3780
gctctgaaaa cgaaaaaacc gccttgcagg gcggtttttc gaaggttctc tgagctacca    3840
actctttgaa ccgaggtaac tggcttggag gagcgcagtc accaaaactt gtcctttcag    3900
tttagcctta accggcgcat gacttcaaga ctaactcctc taaatcaatt accagtggct    3960
gctgccagtg gtgcttttgc atgtctttcc gggttggact caagacgata gttaccggat    4020
aaggcgcagc ggtcggactg aacggggggt tcgtgcatac agtccagctt ggagcgaact    4080
gcctacccgg aactgagtgt caggcgtgga atgagacaaa cgcggccata acagcggaat    4140
gacaccggta aaccgaaagg caggaacagg agagcgcacg agggagccgc caggggaaac    4200
gcctggtatc tttatagtcc tgtcgggttt cgccaccact gatttgagcg tcagatttcg    4260
tgatgcttgt caggggggcg gagcctatgg aaaaacggct ttgccgcggc cctctcactt    4320
ccctgttaag tatcttcctg gcatcttcca ggaaatctcc gccccgttcg taagccattt    4380
ccgctcgccg cagtcgaacg accgagcgta gcgagtcagt gagcgaggaa gcggaatata    4440
tcctgtatca catattctgc tgacgcaccg gtgcagcctt ttttctcctg ccacatgaag    4500
cacttcactg acaccctcat cagtgccaac atagtaagcc agtatacact ccgctagcgc    4560
tgaggtctgc ctcgtgaaga aggtgttgct gactcatacc aggcctgaat cgccccatca    4620
tccagccaga aagtgaggga gccacggttg atgagagctt tgttgtaggt ggaccagttg    4680
gtgattttga acttttgctt tgccacggaa cggtctgcgt tgtcgggaag atgcgtgatc    4740
tgatccttca actcagcaaa agttcgattt attcaacaaa gccacgttgt gtctcaaaat    4800
```

-continued

| | |
|---|---|
| ctctgatgtt acattgcaca agataaaaat atatcatcat gaacaataaa actgtctgct | 4860 |
| tacataaaca gtaatacaag gggtgttgcc | 4890 |

<210> SEQ ID NO 90
<211> LENGTH: 4935
<212> TYPE: DNA
<213> ORGANISM: Artificial Sequence
<220> FEATURE:
<223> OTHER INFORMATION: Synthetic Construct

<400> SEQUENCE: 90

| | |
|---|---|
| cagctgtctc ttatacacat ctcacagcta acaccacgtc gtccctatct gctgccctag | 60 |
| gtctatgagt ggttgctgga taactttacg ggcatgcata aggctcgtat aatatattca | 120 |
| gggagaccac aacggtttcc ctctacaaat aattttgttt aactttgccc gcgctctccc | 180 |
| ccaccaaccc caatttcaca caggaaagta ctagatggct agtagtgagg atataatcaa | 240 |
| agagtttatg cgttttaaag ttcacatgga aggttcagta aacggacatg aatttgaaat | 300 |
| tgagggagaa ggagagggtc gtccgtacga aggtacacaa acagcaaagt taaaagtaac | 360 |
| aaaaggagga cctttaccat ttgcatggga tattctttct ccacaattta tgtatggtag | 420 |
| taaagcgtat gttaaacacc cggcagatat accagactac ttaaagttga gttttccgga | 480 |
| aggattcaaa tgggaacgtg ttatgaattt tgaagatggt ggtgttgtta cagttactca | 540 |
| agatagtagc ttacaggatg gtgaatttat ttacaaagta aaattacgtg gtactaactt | 600 |
| cccgagcgat ggtccagtaa tgcaaaagaa aactatggga tgggaggcta gttctgaacg | 660 |
| tatgtatcct gaagacggtg ctttaaaagg agaaattaaa caacgtttga acttaaagaa | 720 |
| tggtggacac tacgatgcag aagttaaaac tacatataaa gctaaaaagc ctgttcagct | 780 |
| tccgggtgct tataatgtga atataaaatt agatatcaca agtcataacg aagattatac | 840 |
| tattgttgaa cagtatgaaa gagcagaagg aagacattct acaggagcag ccttagaagt | 900 |
| acttttccaa ggtccagatc gtgtatatat tcacccttt catttagaac aaaaacttat | 960 |
| ttcagaggaa gacttataaa gagaatataa aaagccagat tattaatccg gcttttttat | 1020 |
| tatttgccgg ccagtctaca tgtactcttt ttgataaaaa attggagatt cctttacaaa | 1080 |
| tatgctctta cgtgctatta tttaagtgac tatttaaaag gagttaataa atatgcggca | 1140 |
| aggtattctt aaataaactg tcaatttgat agcgggaaca ataattaga tgtcctttt | 1200 |
| taggagggct tagttttttg tacccagttt aagaatacct ttatcatgtg attctaaagt | 1260 |
| atccagagaa tatctgtatg ctttgtatac ctatggttat gcataaaaat cccggtgata | 1320 |
| aaagtattta tcactgggat ttttatgccc ttttgggttt ttgaatggag gaatactaga | 1380 |
| tgaaaatcat aaatatcggt gtattagctc acgttgatgc aggaaaaaca acattaactg | 1440 |
| aatcactttt atataactct ggtgcaatta ctgaacttgg ttcagtagat aaaggtacta | 1500 |
| ctcgtactga taatacatta ttagaacgtc aacgtggaat cacaattcaa acaggtatca | 1560 |
| catcttttca atgggaaaat acaaaagtaa atattataga tacacctgga cacatggatt | 1620 |
| tccttgcaga agtataccgt agtctttcag tattagatgg tgctatttta cttatcagcg | 1680 |
| ctaaagatgg agttcaagct caaactcgta tcttatttca cgcattacgt aaaatgggta | 1740 |
| ttccaacaat tttctttata aacaaaattg accaaaacgg aattgattta agtacagttt | 1800 |
| atcaagatat caaagaaaaa ctttctgctg aaatcgttat taaacaaaaa gttgaattat | 1860 |
| acccaaacgt ttgcgtaaca aattttactg aatcagaaca atgggataca gttatagaag | 1920 |
| gtaatgatga tttattagaa aaatacatgt caggtaaatc attagaagca ttagaattag | 1980 |

```
aacaagaaga aagtattcgt ttccaaaact gttctttatt ccctttatac catggaagcg    2040
ctaaaagtaa cataggtatt gataacttaa ttgaagttat tactaacaaa ttttattctt    2100
caactcatcg tgggccttct gaattatgcg gtaacgtttt caaaattgaa tatacaaaaa    2160
aacgtcaacg tttagcttat atacgtcttt atagtggtgt tttacattta cgtgatagtg    2220
ttcgtgttag tgaaaagaa aagattaaag ttacagaaat gtatacttct attaacggtg     2280
aattatgcaa aattgaccgt gcatattcag gtgaaattgt aattttacaa aacgaatttc    2340
ttaaacttaa tagtgtactt ggtgacacaa aacttttacc acaacgtaag aaaattgaaa    2400
atccacaccc attacttcaa acaacagtag aaccaagcaa acctgaacaa cgtgaaatgc    2460
ttttagatgc tcttttagaa attagtgact ctgacccact tttacgttac tatgtagatt    2520
ctactactca tgaaattatt ctttctttcc ttggtaaagt tcaaatggaa gttatttctg    2580
cattattaca agaaaaatat catgttgaaa tcgaattaaa agaacctact gtaatttata    2640
tggaacgtcc attaaaaaat gctgaatata caattcatat tgaagttcca ccaaatccat    2700
tttgggcttc tattggtctt tctgtttctc cacttccact tggtagcgga atgcaatatg    2760
aaagtagcgt aagtttaggt tatcttaatc aaagtttcca aaacgcagtt atggaaggta    2820
ttcgttacgg ttgcgaacaa ggtttatacg gttggaatgt tacagactgc aaaatctgtt    2880
ttaagtatgg actttactat tcacctgtat caacacctgc tgactttcgt atgcttgcac    2940
caattgtttt agaacaagtt ttaaagaaag ctggaactga acttttagaa ccataccttt    3000
cttttaaaat ctatgcacca caagaatact taagtcgtgc ttataacgat gcacctaaat    3060
actgtgctaa tattgttgat actcaattaa agaacaacga agtaatttta agcggagaaa    3120
ttcctgcacg ttgtattcaa gaatatcgta gtgatttaac attttcact aatggacgtt      3180 ctgtttgctt aactgaatta aaaggttatc atgttactac tggtgaacct gtatgccaac    3240
cacgtcgtcc taatagtcgt attgataaag ttcgttatat gttcaacaaa atcacataat    3300 aaaaaaaaa accccgcccc tgacagggcg gggttttttt tttagttagt tagagatgtg     3360
tataagagac agctggccat ggaatagact ggatggaggc ggataaagtt gcaggaccac    3420
ttctgcgctc ggcccttccg gctggctggt ttattgctga taaatctgga gccggtgagc    3480
gtgggtctcg cggtatcatt gcagcactgg ggccagatgg taagccctcc cgtatcgtag    3540
ttatctacac gacggggagt caggcaacta tggatgaacg aaatagacag atcgctgaga    3600
taggtgcctc actgattaag cattggtaac tgtcagacca agtttactca tatatacttt    3660
agattgattt aaaacttcat ttttaattta aaaggatcta ggtgaagatc ctttttgata    3720
atctcatgac caaaatccct taacgtgagt tttcgttcca ctgagcgtca gaccccttaa    3780
taagatgatc ttcttgagat cgttttggtc tgcgcgtaat ctcttgctct gaaaacgaaa    3840
aaaccgcctt gcagggcggt ttttcgaagg ttctctgagc taccaactct ttgaaccgag    3900
gtaactggct tggaggagcg cagtcaccaa aacttgtcct ttcagtttag ccttaaccgg    3960
cgcatgactt caagactaac tcctctaaat caattaccag tggctgctgc cagtggtgct    4020
tttgcatgtc tttccgggtt ggactcaaga cgatagttac cggataaggc gcagcggtcg    4080
gactgaacgg ggggttcgtg catacagtcc agcttggagc gaactgccta cccggaactg    4140
agtgtcaggc gtggaatgag acaaacgcgg ccataacagc ggaatgacac cggtaaaccg    4200
aaaggcagga acaggagagc gcacgaggga gccgccaggg gaaacgcctg gtatctttat    4260
agtcctgtcg ggtttcgcca ccactgattt gagcgtcaga tttcgtgatg cttgtcaggg    4320
```

```
gggcggagcc tatggaaaaa cggctttgcc gcggccctct cacttccctg ttaagtatct    4380
tcctggcatc ttccaggaaa tctccgcccc gttcgtaagc catttccgct cgccgcagtc    4440
gaacgaccga gcgtagcgag tcagtgagcg aggaagcgga atatatcctg tatcacatat    4500
tctgctgacg caccggtgca gccttttttc tcctgccaca tgaagcactt cactgacacc    4560
ctcatcagtg ccaacatagt aagccagtat acactccgct agcgctgagg tctgcctcgt    4620
gaagaaggtt ttgctgactc ataccaggcc tgaatcgccc catcatccag ccagaaagtg    4680
agggagccac ggttgatgag agctttgttg taggtggacc agttggtgat tttgaacttt    4740
tgctttgcca cggaacggtc tgcgttgtcg ggaagatgcg tgatctgatc cttcaactca    4800
gcaaaagttc gatttattca acaaagccac gttgtgtctc aaaatctctg atgttacatt    4860
gcacaagata aaaatatatc atcatgaaca ataaaactgt ctgcttacat aaacagtaat    4920 acaagggtg ttgcc                                                      4935

<210> SEQ ID NO 91
<211> LENGTH: 5166
<212> TYPE: DNA
<213> ORGANISM: Artificial Sequence
<220> FEATURE:
<223> OTHER INFORMATION: Synthetic Construct

<400> SEQUENCE: 91
cacagctaac accacgtcgt ccctatctgc tgccctaggt ctatgagtgg ttgctggata      60
actttacggg catgcataag gctcgtataa tatattcagg gagaccacaa cggtttccct     120
ctacaaataa ttttgtttaa cttttcacac aggaaaccta ctagatgtat ccttacgacg     180
ttccagacta tgcacatagt gatgctgtat ttacagataa cactcgttta gaagtacttt     240
tccaaggtcc aatgaacgag aaaaatataa acacagtca aactttatt acttcaaaac     300 ataatataga taaaataatg acaaatataa gattaaatga acatgataat atctttgaaa     360
tcggctcagg aaaaggccat tttaccettg aattagtaaa gaggtgtaat ttcgtaactg     420
ccattgaaat agaccataaa ttatgcaaaa ctacagaaaa taaacttgtt gaccacgata     480
atttccaagt tttaaacaag gatatattgc agtttaaatt tcctaaaaac caatcctata     540
aaatatatgg taatatacct tataacataa gtacggatat aatacgcaaa attgtttttg     600
atagtatagc taatgagatt tatttaatcg tggaatacgg gtttgctaaa agattattaa     660
atacaaaacg ctcattggca ttacttttaa tggcagaagt tgatatttct atattaagta     720
tggttccaag agaatatttt catcctaaac ctaaagtgaa tagctcactt atcagattaa     780
gtagaaaaaa atcaagaata tcacacaaag ataaacaaaa gtataattat ttcgttatga     840
aatgggttaa caaagaatac aagaaaatat ttacaaaaaa tcaatttaac aattccttaa     900
aacatgcagg aattgacgat ttaaacaata ttagctttga acaattctta tctcttttca     960
atagctataa attatttaat aaggcctaac caggcatcaa ataaaacgaa aggctcagtc    1020
gaaagactgg gcctttcgtt ttatctgttg tttgtcggtg aacgctctct actagagtca    1080
cactggctca ccttcgggtg ggcctttctg cgtttatagc cggccagtct acatgtactc    1140
tttttgataa aaaattggag attccttac aaatatgctc ttacgtgcta ttatttaagt    1200
gactatttaa aaggagttaa taaatatgcg gcaaggtatt cttaaataaa ctgtcaattt    1260
gatagcggga acaaataatt agatgtcctt ttttaggagg gcttagtttt ttgtacccag    1320
tttaagaata cctttatcat gtgattctaa agtatccaga gaatatctgt atgctttgta    1380 taccctatggt tatgcataaa aatcccggtg ataaagtat ttatcactgg gattttatg     1440
```

-continued

```
cccttttggg tttttgaatg gaggaatact agatgaaaat cataaatatc ggtgtattag    1500
ctcacgttga tgcaggaaaa acaacattaa ctgaatcact tttatataac tctggtgcaa    1560
ttactgaact tggttcagta gataaaggta ctactcgtac tgataataca ttattagaac    1620
gtcaacgtgg aatcacaatt caaacaggta tcacatcttt tcaatgggaa aatacaaaag    1680
taaatattat agatacacct ggacacatgg atttccttgc agaagtatac cgtagtcttt    1740
cagtattaga tggtgctatt ttacttatca gcgctaaaga tggagttcaa gctcaaactc    1800
gtatcttatt tcacgcatta cgtaaaatgg gtattccaac aattttcttt ataaacaaaa    1860
ttgaccaaaa cggaattgat ttaagtacag tttatcaaga tatcaaagaa aaactttctg    1920
ctgaaatcgt tattaaacaa aaagttgaat tatacccaaa cgtttgcgta acaaattta    1980
ctgaatcaga acaatgggat acagttatag aaggtaatga tgatttatta gaaaaataca    2040
tgtcaggtaa atcattagaa gcattagaat tagaacaaga agaaagtatt cgtttccaaa    2100
actgttcttt attcccttta taccatgaaa gcgctaaaag taacataggt attgataact    2160
taattgaagt tattactaac aaattttatt cttcaactca tcgtgggcct tctgaattat    2220
gcggtaacgt tttcaaaatt gaatatacaa aaaacgtca acgtttagct tatatacgtc    2280
tttatagtgg tgttttacat ttacgtgata gtgttcgtgt tagtgaaaaa gaaaagatta    2340
aagttacaga aatgtatact tctattaacg gtgaattatg caaaattgac cgtgcatatt    2400
caggtgaaat tgtaatttta caaaacgaat ttcttaaact taatagtgta cttggtgaca    2460
caaaactttt accacaacgt aagaaaattg aaaatccaca cccattactt caaacaacag    2520
tagaaccaag caaacctgaa caacgtgaaa tgcttttaga tgctcttta gaaattagtg    2580
actctgaccc acttttacgt tactatgtag attctactac tcatgaaatt attctttctt    2640
tccttggtaa agttcaaatg gaagttattt ctgcattatt acaagaaaaa tatcatgttg    2700
aaatcgaatt aaaagaacct actgtaattt atatggaacg tccattaaaa aatgctgaat    2760
atacaattca tattgaagtt ccaccaaatc catttttggc ttctattggt ctttctgttt    2820
ctccacttcc acttggtagc ggaatgcaat atgaaagtag cgtaagttta ggttatctta    2880
atcaaagttt ccaaaacgca gttatggaag gtattcgtta cggttgcgaa caaggtttat    2940
acggttggaa tgttcagac tgcaaaatct gttttaagta tggactttac tattcacctg    3000
tatcaacacc tgctgacttt cgtatgcttg caccaattgt tttagaacaa gttttaaaga    3060
aagctggaac tgaactttta gaaccatacc tttcttttaa aatctatgca ccacaagaat    3120
acttaagtcg tgcttataac gatgcaccta aatactgtgc taatattgtt gatactcaat    3180
taaagaacaa cgaagtaatt ttaagcggag aaattcctgc acgttgtatt caagaatatc    3240
gtagtgattt aacatttttc actaatggac gttctgtttg cttaactgaa ttaaaaggtt    3300
atcatgttac tactggtgaa cctgtatgcc aaccacgtcg tcctaatagt cgtattgata    3360
aagttcgtta tatgttcaac aaaatcacat aataaaaaa aaacccgc ccctgacagg    3420
gcggggtttt ttttttagtt agttagagat gtgtataaga gacagctggc catggaatag    3480
actggatgga ggcggataaa gttgcaggac cacttctgcg ctcggccctt ccggctggct    3540
ggtttattgc tgataaatct ggagccggtg agcgtgggtc tcgcggtatc attgcagcac    3600
tggggccaga tggtaagccc tcccgtatcg tagttatcta cacgacgggg agtcaggcaa    3660
ctatggatga acgaaataga cagatcgctg agataggtgc ctcactgatt aagcattggt    3720
aactgtcaga ccaagtttac tcatatatac tttagattga tttaaaactt cattttttaat    3780
```

| | |
|---|---|
| ttaaaaggat ctaggtgaag atccttttg ataatctcat gaccaaaatc ccttaacgtg | 3840 |
| agttttcgtt ccactgagcg tcagacccct taataagatg atcttcttga gatcgttttg | 3900 |
| gtctgcgcgt aatctcttgc tctgaaaacg aaaaaaccgc cttgcagggc ggttttttcga | 3960 |
| aggttctctg agctaccaac tctttgaacc gaggtaactg gcttggagga gcgcagtcac | 4020 |
| caaaacttgt cctttcagtt tagccttaac cggcgcatga cttcaagact aactcctcta | 4080 |
| aatcaattac cagtggctgc tgccagtggt gcttttgcat gtcttttccgg gttggactca | 4140 |
| agacgatagt taccggataa ggcgcagcgg tcggactgaa cggggggttc gtgcatacag | 4200 |
| tccagcttgg agcgaactgc ctacccggaa ctgagtgtca ggcgtggaat gagacaaacg | 4260 |
| cggccataac agcggaatga caccggtaaa ccgaaaggca ggaacaggag agcgcacgag | 4320 |
| ggagccgcca ggggaaacgc ctggtatctt tatagtcctg tcgggtttcg ccaccactga | 4380 |
| tttgagcgtc agatttcgtg atgcttgtca gggggcgga gcctatggaa aaacggcttt | 4440 |
| gccgcggccc tctcacttcc ctgttaagta tcttcctggc atcttccagg aaatctccgc | 4500 |
| cccgttcgta agccatttcc gctcgccgca gtcgaacgac cgagcgtagc gagtcagtga | 4560 |
| gcgaggaagc ggaatatatc ctgtatcaca tattctgctg acgcaccggt gcagcctttt | 4620 |
| ttctcctgcc acatgaagca cttcactgac accctcatca gtgccaacat agtaagccag | 4680 |
| tatacactcc gctagcgctg aggtctgcct cgtgaagaag gtgttgctga ctcataccag | 4740 |
| gcctgaatcg ccccatcatc cagccagaaa gtgagggagc cacggttgat gagagctttg | 4800 |
| ttgtaggtgg accagttggt gattttgaac ttttgctttg ccacggaacg gtctgcgttg | 4860 |
| tcgggaagat gcgtgatctg atccttcaac tcagcaaaag ttcgatttat tcaacaaagc | 4920 |
| cacgttgtgt ctcaaaatct ctgatgttac attgcacaag ataaaaatat atcatcatga | 4980 |
| acaataaaac tgtctgctta cataaacagt aatacaaggg gtgttgccca gctgtctctt | 5040 |
| atacacatct ccggcttatc ggtcagtttc acctgattta cgtaaaaacc cgcttcggcg | 5100 |
| ggttttgct tttggagggg cagaaagatg aatgactgtc cacgacgcta tacccaaaag | 5160 |
| aaagcc | 5166 |

<210> SEQ ID NO 92
<211> LENGTH: 4994
<212> TYPE: DNA
<213> ORGANISM: Artificial Sequence
<220> FEATURE:
<223> OTHER INFORMATION: Synthetic Construct

<400> SEQUENCE: 92

| | |
|---|---|
| cagctgtctc ttatacacat ctcacagcta acaccacgtc gtccctatct gctgccctag | 60 |
| gtctatgagt ggttgctgga taactttacg ggcatgcata aggctcgtat gatatattca | 120 |
| gggagaccac aacggtttcc ctctacaaat aattttgttt aactttaaag aggagaaata | 180 |
| ctagatggaa caaaaactta tttcagagga agacttacat agtgatgctg tatttacaga | 240 |
| taacactcgt ttagaagtac ttttccaagg tccaatggct agtagtgagg atataatcaa | 300 |
| agagtttatg cgttttaaag ttcacatgga aggttcagta aacggacatg aatttgaaat | 360 |
| tgagggagaa ggagagggtc gtccgtacga aggtacacaa acagcaaagt taaaagtaac | 420 |
| aaaaggagga cctttaccat tgcatgggga tattctttct ccacaattta tgtatggtag | 480 |
| taaagcgtat gttaaacacc cggcagatat accagactat ttaaagttga gttttccgga | 540 |
| aggattcaaa tgggaacgtg ttatgaattt tgaagatggt ggtgttgtta cagttactca | 600 |
| agatagtagc ttacaggatg gtgaatttat ttacaaagta aaattacgtg gtactaactt | 660 |

```
cccgagcgat ggtccagtaa tgcaaaagaa aactatggga tgggaggcta gttctgaacg    720
tatgtatcct gaagacggtg ctttaaaagg agaaattaaa caacgtttga aacttaaaga    780
tggtggacac tacgatgcag aagttaaaac tacatataaa gctaaaaagc ctgttcagct    840
tccgggtgct tataatgtga atataaaatt agatatcaca agtcataacg aagattatac    900
tattgttgaa cagtatgaaa gagcagaagg aagacattct acaggagcag cctaaccagg    960
catcaaataa aacgaaaggc tcagtcgaaa gactgggcct ttcgttttat ctgttgtttg   1020
tcggtgaacg ctctctacta gagtcacact ggctcacctt cgggtgggcc tttctgcgtt   1080
tataccggc cagtctacat gtactctttt tgataaaaaa ttggagattc ctttacaaat    1140
atgctcttac gtgctattat ttaagtgact atttaaaagg agttaataaa tatgcggcaa   1200
ggtattctta aataaactgt caatttgata gcgggaacaa ataattagat gtccttttt    1260
aggagggctt agttttttgt acccagttta agaatacctt tatcatgtga ttctaaagta   1320
tccagagaat atctgtatgc tttgtatacc tatggttatg cataaaaatc ccggtgataa   1380
aagtatttat cactgggatt tttatgccct tttgggtttt tgaatggagg aatactagat   1440
gaaaatcata aatatcggtg tattagctca cgttgatgca ggaaaaacaa cattaactga   1500
atcactttta tataactctg gtgcaattac tgaacttggt tcagtagata aggtactac    1560
tcgtactgat aatacattat tagaacgtca acgtggaatc acaattcaaa caggtatcac   1620
atcttttcaa tgggaaaata caaagtaaa tattatagat acacctggac acatggattt   1680
ccttgcagaa gtataccgta gtcttttcagt attagatggt gctattttac ttatcagcgc   1740
taaagatgga gttcaagctc aaactcgtat cttatttcac gcattacgta aaatgggtat   1800
tccaacaatt ttctttataa acaaaattga ccaaaacgga attgatttaa gtacagttta   1860
tcaagatatc aaagaaaaac tttctgctga atcgttatt aaacaaaaag ttgaattata   1920
cccaaacgtt tgcgtaacaa attttactga atcagaacaa tgggatacag ttatagaagg   1980
taatgatgat ttattagaaa aatacatgtc aggtaaatca ttagaagcat tagaattaga   2040
acaagaagaa agtattcgtt tccaaaactg ttctttattc cctttatacc atggaagcgc   2100
taaaagtaac ataggtattg ataacttaat tgaagttatt actaacaaat tttattcttc   2160
aactcatcgt gggccttctg aattatgcgg taacgttttc aaaattgaat atacaaaaaa   2220
acgtcaacgt ttagcttata tacgtcttta tagtggtgtt ttacatttac gtgatagtgt   2280
tcgtgttagt gaaaagaaa agattaaagt tacagaaatg tatacttcta ttaacggtga   2340
attatgcaaa attgaccgtg catattcagg tgaaattgta atttacaaa acgaatttct   2400
taaacttaat agtgtacttg gtgacacaaa acttttacca caacgtaaga aaattgaaaa   2460
tccacaccca ttacttcaaa caacagtaga accaagcaaa cctgaacaac gtgaaatgct   2520
tttagatgct ctttttagaaa ttagtgactc tgacccactt ttacgttact atgtagattc   2580
tactactcat gaaattattc tttctttcct tggtaaagtt caaatggaag ttatttctgc   2640
attattacaa gaaaaatatc atgttgaaat cgaattaaaa gaacctactg taatttatat   2700
ggaacgtcca ttaaaaaatg ctgaatatac aattcatatt gaagttccac caaatccatt   2760
ttgggcttct attggtcttt ctgtttctcc acttccactt ggtagcggaa tgcaatatga   2820
aagtagcgta agtttaggtt atcttaatca aagtttccaa aacgcagtta tggaaggtat   2880
tcgttacggt tgcgaacaag gtttatacgg ttggaatgtt acagactgca aaatctgttt   2940
taagtatgga ctttactatt cacctgtatc aacacctgct gactttcgta tgcttgcacc   3000
```

```
aattgtttta gaacaagttt taaagaaagc tggaactgaa cttttagaac catacctttc      3060
ttttaaaatc tatgcaccac aagaatactt aagtcgtgct tataacgatg cacctaaata      3120
ctgtgctaat attgttgata ctcaattaaa gaacaacgaa gtaattttaa gcggagaaat      3180
tcctgcacgt tgtattcaag aatatcgtag tgatttaaca tttttcacta atggacgttc      3240
tgtttgctta actgaattaa aaggttatca tgttactact ggtgaacctg tatgccaacc      3300
acgtcgtcct aatagtcgta ttgataaagt tcgttatatg ttcaacaaaa tcacataata      3360
aaaaaaaaaa ccccgcccct gacagggcgg ggtttttttt ttagttagtt agagatgtgt      3420
ataagagaca gctggccatg gaatagactg gatggaggcg gataaagttg caggaccact      3480
tctgcgctcg gcccttccgg ctggctggtt tattgctgat aaatctggag ccggtgagcg      3540
tgggtctcgc ggtatcattg cagcactggg gccagatggt aagccctccc gtatcgtagt      3600
tatctacacg acggggagtc aggcaactat ggatgaacga atagacaga tcgctgagat      3660 aggtgcctca ctgattaagc attggtaact gtcagaccaa gtttactcat atatacttta      3720
gattgattta aaacttcatt tttaatttaa aaggatctag gtgaagatcc ttttttgataa      3780 tctcatgacc aaaatccctt aacgtgagtt ttcgttccac tgagcgtcag accccttaat      3840
aagatgatct tcttgagatc gttttggtct gcgcgtaatc tcttgctctg aaaacgaaaa      3900
aaccgccttg cagggcggtt tttcgaaggt tctctgagct accaactctt tgaaccgagg      3960
taactggctt ggaggagcgc agtcaccaaa acttgtcctt tcagtttagc cttaaccggc      4020
gcatgacttc aagactaact cctctaaatc aattaccagt ggctgctgcc agtggtgctt      4080
ttgcatgtct ttccgggttg gactcaagac gatagttacc ggataaggcg cagcggtcgg      4140
actgaacggg gggttcgtgc atacagtcca gcttggagcg aactgcctac ccggaactga      4200
gtgtcaggcg tggaatgaga caaacgcggc cataacagcg gaatgacacc ggtaaaccga      4260
aaggcaggaa caggagagcg cacgagggag ccgccagggg aaacgcctgg tatctttata      4320
gtcctgtcgg gtttcgccac cactgatttg agcgtcagat ttcgtgatgc ttgtcagggg      4380
ggcggagcct atggaaaaac ggctttgccg cggccctctc acttccctgt taagtatctt      4440
cctggcatct tccaggaaat ctccgccccg ttcgtaagcc atttccgctc gccgcagtcg      4500
aacgaccgag cgtagcgagt cagtgagcga ggaagcggaa tatatcctgt atcacatatt      4560
ctgctgacgc accggtgcag ccttttttct cctgccacat gaagcacttc actgacaccc      4620
tcatcagtgc caacatagta agccagtata cactccgcta gcgctgaggt ctgcctcgtg      4680
aagaaggtgt tgctgactca taccaggcct gaatcgcccc atcatccagc cagaaagtga      4740
gggagccacg gttgatgaga ctttgttgt aggtggacca gttggtgatt ttgaactttt      4800
gctttgccac ggaacggtct gcgttgtcgg gaagatgcgt gatctgatcc ttcaactcag      4860
caaaagttcg atttattcaa caaagccacg ttgtgtctca aaatctctga tgttacattg      4920
cacaagataa aaatatatca tcatgaacaa taaaactgtc tgcttacata acagtaata      4980 caagggtgt tgcc                                                          4994
```

<210> SEQ ID NO 93
<211> LENGTH: 5046
<212> TYPE: DNA
<213> ORGANISM: Artificial Sequence
<220> FEATURE:
<223> OTHER INFORMATION: Synthetic Construct

<400> SEQUENCE: 93

```
cacagctaac accacgtcgt ccctatctgc tgccctaggt ctatgagtgg ttgctggata        60
```

```
actttacggg catgcataag gctcgtataa tatattcagg gagaccacaa cggtttccct      120
ctacaaataa ttttgtttaa ctttgccggg cccaagttca cttaaaaagg agatcaacaa      180
tgaaagcaat tttcgtactg aaacatctta atcatgcaca ggagactttc taatggctag      240
tagtgaggat ataatcaaag agtttatgcg ttttaaagtt cacatggaag gttcagtaaa      300
cggacatgaa tttgaaattg agggagaagg agagggtcgt ccgtacgaag gtacacaaac      360
agcaaagtta aaagtaacaa aaggaggacc tttaccattt gcatgggata ttctttctcc      420
acaatttatg tatggtagta aagcgtatgt taaacacccg gcagatatac cagactattt      480
aaagttgagt tttccggaag gattcaaatg ggaacgtgtt atgaattttg aagatggtgg      540
tgttgttaca gttactcaag atagtagctt acaggatggt gaatttattt acaaagtaaa      600
attacgtggt actaacttcc cgagcgatgg tccagtaatg caaaagaaaa ctatgggatg      660
ggaggctagt tctgaacgta tgtatcctga agacggtgct ttaaaaggag aaattaaaca      720
acgtttgaaa cttaaagatg gtggacacta cgatgcagaa gttaaaacta catataaagc      780
taaaaagcct gttcagcttc cgggtgctta taatgtgaat ataaaattag atatcacaag      840
tcataacgaa gattatacta ttgttgaaca gtatgaaaga gcagaaggaa gacattctac      900
aggagcagcc ttagaagtac ttttccaagg tccatacgga ggttttcttt aaagagaata      960
taaaaagcca gattattaat ccggcttttt tattatttgc cggccagtct acatgtactc     1020
tttttgataa aaaattggag attcctttac aaatatgctc ttacgtgcta ttatttaagt     1080
gactatttaa aaggagttaa taaatatgcg gcaaggtatt cttaaataaa ctgtcaattt     1140
gatagcggga acaaataatt agatgtcctt ttttaggagg gcttagtttt ttgtacccag     1200
tttaagaata cctttatcat gtgattctaa agtatccaga gaatatctgt atgctttgta     1260
tacctatggt tatgcataaa aatcccggtg ataaaagtat ttatcactgg gattttatg     1320 cccttttggg tttttgaatg gaggaatact agatgaaaat cataaatatc ggtgtattag     1380
ctcacgttga tgcaggaaaa acaacattaa ctgaatcact tttatataac tctggtgcaa     1440
ttactgaact tggttcagta gataaaggta ctactcgtac tgataataca ttattagaac     1500
gtcaacgtgg aatcacaatt caaacaggta tcacatcttt tcaatgggaa aatacaaaag     1560
taaatattat agatacacct ggacacatgg atttccttgc agaagtatac cgtagtcttt     1620
cagtattaga tggtgctatt ttacttatca gcgctaaaga tggagttcaa gctcaaactc     1680
gtatcttatt tcacgcatta cgtaaaatgg gtattccaac aattttcttt ataaacaaaa     1740
ttgaccaaaa cggaattgat ttaagtacag tttatcaaga tatcaaagaa aaactttctg     1800
ctgaaatcgt tattaaacaa aaagttgaat tatacccaaa cgtttgcgta acaaattta      1860 ctgaatcaga acaatgggat acagttatag aaggtaatga tgatttatta gaaaaataca     1920
tgtcaggtaa atcattagaa gcattagaat tagaacaaga agaaagtatt cgtttccaaa     1980
actgttcttt attcccttta taccatggaa gcgctaaaag taacataggt attgataact     2040
taattgaagt tattactaac aaatttttatt cttcaactca tcgtgggcct tctgaattat     2100
gcggtaacgt tttcaaaatt gaatatacaa aaaaacgtca acgtttagct tatatacgtc     2160
tttatagtgg tgttttacat ttacgtgata gtgttcgtgt tagtgaaaaa gaaaagatta     2220
aagttacaga aatgtatact tctattaacg gtgaattatg caaaattgac cgtgcatatt     2280
caggtgaaat tgtaattta caaaacgaat ttcttaaact taatagtgta cttggtgaca     2340
caaacttttt accacaacgt aagaaaattg aaaatccaca cccattactt caaacaacag     2400
```

```
tagaaccaag caaacctgaa caacgtgaaa tgcttttaga tgctctttta gaaattagtg   2460
actctgaccc acttttacgt tactatgtag attctactac tcatgaaatt attctttctt   2520
tccttggtaa agttcaaatg gaagttattt ctgcattatt acaagaaaaa tatcatgttg   2580
aaatcgaatt aaaagaacct actgtaattt atatggaacg tccattaaaa aatgctgaat   2640
atacaattca tattgaagtt ccaccaaatc cattttgggc ttctattggt ctttctgttt   2700
ctccacttcc acttggtagc ggaatgcaat atgaaagtag cgtaagttta ggttatctta   2760
atcaaagttt ccaaaacgca gttatggaag gtattcgtta cggttgcgaa caaggtttat   2820
acggttggaa tgttacagac tgcaaaatct gttttaagta tggactttac tattcacctg   2880
tatcaacacc tgctgacttt cgtatgcttg caccaattgt tttagaacaa gttttaaaga   2940
aagctggaac tgaactttta gaaccatacc tttcttttaa aatctatgca ccacaagaat   3000
acttaagtcg tgcttataac gatgcaccta atactgtgc taatattgtt gatactcaat   3060
taaagaacaa cgaagtaatt ttaagcggag aaattcctgc acgttgtatt caagaatatc   3120
gtagtgattt aacatttttc actaatggac gttctgtttg cttaactgaa ttaaaaggtt   3180
atcatgttac tactggtgaa cctgtatgcc aaccacgtcg tcctaatagt cgtattgata   3240
aagttcgtta tatgttcaac aaaatcacat aataaaaaaa aaaacccgc ccctgacagg   3300
gcggggtttt tttttagtt agttagagat gtgtataaga acagctggc catggaatag   3360
actggatgga ggcggataaa gttgcaggac cacttctgcg ctcggccctt ccggctggct   3420
ggtttattgc tgataaatct ggagccggtg agcgtgggtc tcgcggtatc attgcagcac   3480
tggggccaga tggtaagccc tcccgtatcg tagttatcta cacgacgggg agtcaggcaa   3540
ctatggatga acgaaataga cagatcgctg agataggtgc ctcactgatt aagcattggt   3600
aactgtcaga ccaagtttac tcatatatac tttagattga tttaaaactt catttttaat   3660
ttaaaaggat ctaggtgaag atccttttg ataatctcat gaccaaaatc ccttaacgtg   3720
agttttcgtt ccactgagcg tcagaccccct taataagatg atcttcttga gatcgttttg   3780
gtctgcgcgt aatctcttgc tctgaaaacg aaaaaaccgc cttgcagggc ggttttcga   3840
aggttctctg agctaccaac tctttgaacc gaggtaactg gcttggagga gcgcagtcac   3900
caaaacttgt ccttttcagtt tagccttaac cggcgcatga cttcaagact aactcctcta   3960
aatcaattac cagtggctgc tgccagtggt gcttttgcat gtctttccgg gttggactca   4020
agacgatagt taccggataa ggcgcagcgg tcggactgaa cggggggttc gtgcatacag   4080
tccagcttgg agcgaactgc ctacccgaa ctgagtgtca ggcgtggaat gagacaaacg   4140
cggccataac agcggaatga caccggtaaa ccgaaaggca ggaacaggag agcgcacgag   4200
ggagccgcca ggggaaacgc ctggtatctt tatagtcctg tcgggtttcg ccaccactga   4260
tttgagcgtc agatttcgtg atgcttgtca ggggggcgga gcctatggaa aaacggcttt   4320
gccgcggccc tctcacttcc ctgttaagta tcttcctggc atcttccagg aaatctccgc   4380
cccgttcgta agccatttcc gctcgccgca gtcgaacgac cgagcgtagc gagtcagtga   4440
gcgaggaagc ggaatatatc ctgtatcaca tattctgctg acgcaccggt gcagcctttt   4500
ttctcctgcc acatgaagca cttcactgac accctcatca gtgccaacat agtaagccag   4560
tatacactcc gctagcgctg aggtctgcct cgtgaagaag gtgttgctga ctcataccag   4620
gcctgaatcg ccccatcatc cagccagaaa gtgagggagc cacggttgat gagagctttg   4680
ttgtaggtgg accagttggt gattttgaac ttttgctttg ccacgaacg gtctgcgttg   4740
tcgggaagat gcgtgatctg atccttcaac tcagcaaaag ttcgatttat tcaacaaagc   4800
```

```
cacgttgtgt ctcaaaatct ctgatgttac attgcacaag ataaaaatat atcatcatga    4860
acaataaaac tgtctgctta cataaacagt aatacaaggg gtgttgccca gctgtctctt    4920
atacacatct ccggcttatc ggtcagtttc acctgattta cgtaaaaacc cgcttcggcg    4980 ggttttttgct tttggagggg cagaaagatg aatgactgtc cacgacgcta tacccaaaag    5040
aaagcc                                                                5046
```

<210> SEQ ID NO 94
<211> LENGTH: 4961
<212> TYPE: DNA
<213> ORGANISM: Artificial Sequence
<220> FEATURE:
<223> OTHER INFORMATION: Synthetic Construct

<400> SEQUENCE: 94

```
cagctgtctc ttatacacat ctcacagcta acaccacgtc gtccctatct gctgccctag      60
gtctatgagt ggttgctgga taactttacg ggcatgcata aggctcgtat gatatattca     120
gggagaccac aacggtttcc ctctacaaat aattttgttt aactttaaag aggagaaata     180
ctagatggac cgtgtatata ttcacccttt tcatttatta gaagtacttt tccaaggtcc     240
aatggctagt agtgaggata taatcaaaga gtttatgcgt tttaaagttc acatggaagg     300
ttcagtaaac ggacatgaat tgaaaattga gggagaagga gagggtcgtc cgtacgaagg     360
tacacaaaca gcaaagttaa aagtaacaaa aggaggacct ttaccatttg catgggatat     420
tctttctcca caatttatgt atggtagtaa agcgtatgtt aaacacccgg cagatatacc     480
agactatttt aagttgagtt ttccggaagg attcaaatgg gaacgtgtta tgaattttga     540
agatggtggt gttgttacag ttactcaaga tagtagctta caggatggtg aatttattta     600
caaagtaaaa ttacgtggta ctaacttccc gagcgatggt ccagtaatgc aaaagaaaac     660
tatgggatgg gaggctagtt ctgaacgtat gtatcctgaa gacggtgctt taaaaggaga     720
aattaaacaa cgtttgaaac ttaaagatgg tggacactac gatgcagaag ttaaaactac     780
atataaagct aaaaagcctg ttcagcttcc gggtgcttat aatgtgaata taaaattaga     840
tatcacaagt cataacgaag attatactat tgttgaacag tatgaaagag cagaaggaag     900
acattctaca ggagcagcct aaccaggcat caaataaaac gaaaggctca gtcgaaagac     960
tgggcctttc gttttatctg ttgtttgtcg gtgaacgctc tctactagag tcacactggc    1020
tcaccttcgg gtgggccttt ctgcgtttat agccggccag tctacatgta ctctttttga    1080
taaaaaattg gagattcctt tacaaatatg ctcttacgtg ctattattta agtgactatt    1140 taaaggagt taataaatat gcggcaaggt attcttaaat aaactgtcaa tttgatagcg    1200
ggaacaaata attagatgtc ctttttttagg agggcttagt tttttgtacc cagtttaaga    1260 ataccttat catgtgattc taaagtatcc agagaatatc tgtatgcttt gtatacctat    1320
ggttatgcat aaaaatcccg gtgataaaag tatttatcac tgggattttt atgccctttt    1380 gggttttga atggaggaat actagatgaa aatcataaat atcggtgtat tagctcacgt    1440
tgatgcagga aaaacaacat taactgaatc acttttatat aactctggtg caattactga    1500
acttggttca gtagataaag gtactactcg tactgataat acattattag aacgtcaacg    1560
tggaatcaca attcaaacag gtatcacatc ttttcaatgg gaaaatacaa agtaaatat    1620 tatagataca cctggacaca tggatttcct tgcagaagta taccgtagtc tttcagtatt    1680
agatggtgct attttactta tcagcgctaa agatggagtt caagctcaaa ctcgtatctt    1740
```

-continued

```
atttcacgca ttacgtaaaa tgggtattcc aacaattttc tttataaaca aaattgacca    1800
aaacggaatt gatttaagta cagtttatca agatatcaaa gaaaaacttt ctgctgaaat    1860
cgttattaaa caaaaagttg aattataccc aaacgtttgc gtaacaaatt ttactgaatc    1920
agaacaatgg gatacagtta tagaaggtaa tgatgattta ttagaaaaat acatgtcagg    1980
taaatcatta gaagcattag aattagaaca agaagaaagt attcgtttcc aaaactgttc    2040
tttattccct ttataccatg gaagcgctaa agtaacata  ggtattgata acttaattga    2100
agttattact aacaaatttt attcttcaac tcatcgtggg ccttctgaat tatgcggtaa    2160
cgttttcaaa attgaatata caaaaaaacg tcaacgttta gcttatatac gtctttatag    2220
tggtgtttta catttacgtg atagtgttcg tgttagtgaa aaagaaaaga ttaaagttac    2280
agaaatgtat acttctatta acggtgaatt atgcaaaatt gaccgtgcat attcaggtga    2340
aattgtaatt ttacaaaacg aatttcttaa acttaatagt gtacttggtg acacaaaact    2400
tttaccacaa cgtaagaaaa ttgaaaatcc acacccatta cttcaaacaa cagtagaacc    2460
aagcaaacct gaacaacgtg aaatgctttt agatgctctt ttagaaatta gtgactctga    2520 cccacttttta cgttactatg tagattctac tactcatgaa attattcttt ctttccttgg    2580
taaagttcaa atggaagtta tttctgcatt attacaagaa aaatatcatg ttgaaatcga    2640
attaaaagaa cctactgtaa tttatatgga acgtccatta aaaaatgctg aatatacaat    2700
tcatattgaa gttccaccaa atccattttg ggcttctatt ggtctttctg tttctccact    2760
tccacttggt agcggaatgc aatatgaaag tagcgtaagt ttaggttatc ttaatcaaag    2820
tttccaaaac gcagttatgg aaggtattcg ttacggttgc gaacaaggtt tatacggttg    2880
gaatgttaca gactgcaaaa tctgttttaa gtatggactt tactattcac ctgtatcaac    2940
acctgctgac tttcgtatgc ttgcaccaat tgttttagaa caagttttaa agaaagctgg    3000
aactgaactt ttagaaccat acctttcttt taaaatctat gcaccacaag aatacttaag    3060
tcgtgcttat aacgatgcac ctaaatactg tgctaatatt gttgatactc aattaaagaa    3120
caacgaagta attttaagcg gagaaattcc tgcacgttgt attcaagaat atcgtagtga    3180
tttaacattt tcactaatg gacgttctgt ttgcttaact gaattaaaag gttatcatgt    3240
tactactggt gaacctgtat gccaaccacg tcgtcctaat agtcgtattg ataaagttcg    3300
ttatatgttc aacaaaatca cataataaaa aaaaaaccc cgcccctgac agggcgggt     3360 tttttttta gttagttaga gatgtgtata agagacagct ggccatggaa tagactggat    3420
ggaggcggat aaagttgcag gaccacttct gcgctcggcc cttccggctg gctggtttat    3480
tgctgataaa tctggagccg gtgagcgtgg gtctcgcggt atcattgcag cactgggcc     3540 agatggtaag ccctcccgta tcgtagttat ctacacgacg gggagtcagg caactatgga    3600
tgaacgaaat agacagatcg ctgagatagg tgcctcactg attaagcatt ggtaactgtc    3660
agaccaagtt tactcatata ctttagat tgatttaaaa cttcattttt aatttaaaag     3720
gatctaggtg aagatccttt ttgataatct catgaccaaa atcccttaac gtgagttttc    3780
gttccactga gcgtcagacc ccttaataag atgatcttct tgagatcgtt ttggtctgcg    3840
cgtaatctct gctctgaaa acgaaaaaac cgccttgcag gcggtttttt cgaaggttct    3900
ctgagctacc aactctttga accgaggtaa ctggcttgga ggagcgcagt caccaaaact    3960
tgtcctttca gtttagcctt aaccggcgca tgacttcaag actaactcct ctaaatcaat    4020
taccagtggc tgctgccagt ggtgctttttg catgtctttc cgggtggac tcaagacgat     4080 agttaccgga taaggcgcag cggtcggact gaacgggggg ttcgtgcata cagtccagct    4140
```

```
tggagcgaac tgcctacccg gaactgagtg tcaggcgtgg aatgagacaa acgcggccat     4200
aacagcggaa tgacaccggt aaaccgaaag gcaggaacag gagagcgcac gagggagccg     4260 ccagggaaa cgcctggtat ctttatagtc ctgtcgggtt tcgccaccac tgatttgagc     4320
gtcagatttc gtgatgcttg tcagggggc ggagcctatg gaaaaacggc tttgccgcgg     4380
ccctctcact tccctgttaa gtatcttcct ggcatcttcc aggaaatctc cgccccgttc     4440
gtaagccatt tccgctcgcc gcagtcgaac gaccgagcgt agcgagtcag tgagcgagga     4500
agcggaatat atcctgtatc acatattctg ctgacgcacc ggtgcagcct ttttctcct     4560 gccacatgaa gcacttcact gacaccctca tcagtgccaa catagtaagc cagtatacac     4620
tccgctagcg ctgaggtctg cctcgtgaag aaggtgttgc tgactcatac caggcctgaa     4680
tcgccccatc atccagccag aaagtgaggg agccacggtt gatgagagct ttgttgtagg     4740
tggaccagtt ggtgattttg aacttttgct ttgccacgga acggtctgcg ttgtcgggaa     4800
gatgcgtgat ctgatccttc aactcagcaa aagttcgatt tattcaacaa agccacgttg     4860
tgtctcaaaa tctctgatgt tacattgcac aagataaaaa tatatcatca tgaacaataa     4920
aactgtctgc ttacataaac agtaatacaa ggggtgttgc c                         4961

<210> SEQ ID NO 95
<211> LENGTH: 5379
<212> TYPE: DNA
<213> ORGANISM: Artificial Sequence
<220> FEATURE:
<223> OTHER INFORMATION: Synthetic Construct

<400> SEQUENCE: 95
cacagctaac accacgtcgt ccctatctgc tgccctaggt ctatgagtgg ttgctggata       60
actttacggg catgcataag gctcgtataa tatattcagg gagaccacaa cggtttccct      120
ctacaaataa ttttgtttaa cttttcacac aggactacta gatggaccgt gtatatattc      180 acccttttt agaagtactt ttccaaggtc aatgtctca ccttgctgag ttggtcgcat       240
cggccaaagc cgcaatctcg caagcctcgg atgtcgcagc cttggacaat gtccgtgttg      300
agtacttagg caagaaggga catttgacgc tccaaatgac tacgcttcgc gaacttccac      360
ctgaggaacg cccagcagct ggcgccgtca ttaatgaggc caaggaacaa gtccaacaag      420
ccttgaacgc ccgcaaggcc gagttggaga gtgcagcttt gaacgcccgc ttggccgccg      480
agactatcga tgtatccttg cctggccgcc gtatcgagaa tggtggcttg cacccagtca      540
cgcgcacgat tgaccgcatt gagtcgtttt ttggcgaact cggtttcact gttgctacgg      600
gaccagagat tgaggatgac taccacaact tgacgcatt gaatatcccc ggccatcatc      660
cagcccgtgc agaccatgat acattttggt tcgatacaac gcgtttgttg cgcacgcaaa      720
cgagtggtgt ccagattcgt acgatgaagg cacaacaacc tccaatccgc attattgccc      780
caggtcgcgt ctaccgcaat gattatgacc aaacacatac tccaatgttt caccaaatgg      840
agggcttgat tgtcgacacg aatattagtt tcacgaatct taagggtact ttgcatgatt      900
ttttgcgcaa cttttcgag gaggacttac aaatccgttt tcgcccatct tattttccat       960
tcacggagcc atctgctgag gttgatgtta tgggcaagaa tggcaagtgg ttggaggttt     1020
tgggttgtgg aatggttcac ccaaatgttt tacgcaatgt cggtattgac ccagaggtct     1080 attccgctt tggctttgga atgggaatgg aacgcttgac aatgttacgc tatggtgtta    1140
cggatttgcg ctcgtttttt gagaatgact tgcgctttct taagcagttc aagtaagcct     1200
```

```
aaccaggcat caaataaaac gaaaggctca gtcgaaagac tgggcctttc gttttatctg    1260
ttgtttgtcg gtgaacgctc tctactagag tcacactggc tcaccttcgg gtgggccttt    1320
ctgcgtttat agccggccag tctacatgta ctcttttga taaaaaattg gagattcctt     1380
tacaaatatg ctcttacgtg ctattattta agtgactatt taaaggagt taataaatat     1440 gcggcaaggt attcttaaat aaactgtcaa tttgatagcg ggaacaaata attagatgtc    1500
cttttttagg agggcttagt ttttgtacc cagtttaaga ataccttat catgtgattc      1560 taaagtatcc agagaatatc tgtatgcttt gtataccat ggttatgcat aaaaatcccg     1620
gtgataaaag tatttatcac tgggattttt atgccctttt gggtttttga atggaggaat    1680
actagatgaa aatcataaat atcggtgtat tagctcacgt tgatgcagga aaaacaacat    1740
taactgaatc acttttatat aactctggtg caattactga acttggttca gtagataaag    1800
gtactactcg tactgataat acattattag aacgtcaacg tggaatcaca attcaaacag    1860
gtatcacatc ttttcaatgg gaaaatacaa aagtaaatat tatagataca cctggacaca    1920
tggatttcct tgcagaagta taccgtagtc tttcagtatt agatggtgct attttactta    1980
tcagcgctaa agatggagtt caagctcaaa ctcgtatctt atttcacgca ttacgtaaaa    2040
tgggtattcc aacaatttc tttataaaca aaattgacca aaacggaatt gatttaagta     2100
cagtttatca agatatcaaa gaaaactttt ctgctgaaat cgttattaaa caaaaagttg    2160 aattatacc aaacgtttgc gtaacaaatt ttactgaatc agaacaatgg gatacagtta     2220
tagaaggtaa tgatgattta ttagaaaaat acatgtcagg taaatcatta gaagcattag    2280
aattagaaca agaagaaagt attcgtttcc aaaactgttc tttattccct ttataccatg    2340
gaagcgctaa aagtaacata ggtattgata acttaattga agttattact aacaaattt     2400 attcttcaac tcatcgtggg ccttctgaat tatgcggtaa cgttttcaaa attgaatata    2460
caaaaaaacg tcaacgttta gcttatatac gtctttatag tggtgttta catttacgtg     2520 atagtgttcg tgttagtgaa aaagaaaaga ttaaagttac agaaatgtat acttctatta    2580
acggtgaatt atgcaaaatt gaccgtgcat attcaggtga aattgtaatt ttacaaaacg    2640
aatttcttaa acttaatagt gtacttggtg acacaaaact tttaccacaa cgtaagaaaa    2700
ttgaaaatcc acacccatta cttcaaacaa cagtagaacc aagcaaacct gaacaacgtg    2760
aaatgctttt agatgctctt ttagaaatta gtgactctga cccactttta cgttactatg    2820
tagattctac tactcatgaa attattcttt cttttccttgg taaagttcaa atggaagtta   2880
tttctgcatt attacaagaa aaatatcatg ttgaaatcga attaaaagaa cctactgtaa    2940
tttatatgga acgtccatta aaaaatgctg aatatacaat tcatattgaa gttccaccaa    3000
atccattttg ggcttctatt ggtctttctg tttctccact tccacttggt agcggaatgc    3060
aatatgaaag tagcgtaagt ttaggttatc ttaatcaaag tttccaaaac gcagttatgg    3120
aaggtattcg ttacggttgc gaacaaggtt tatacggttg gaatgttaca gactgcaaaa    3180
tctgttttaa gtatggactt tactattcac ctgtatcaac acctgctgac tttcgtatgc    3240
ttgcaccaat tgttttagaa caagttttaa agaaagctgg aactgaactt ttagaaccat    3300
acctttcttt taaatctat gcaccacaag aatacttaag tcgtgcttat aacgatgcac     3360
ctaaatactg tgctaatatt gttgatactc aattaaagaa caacgaagta attttaagcg    3420
gagaaattcc tgcacgttgt attcaagaat atcgtagtga tttaacattt ttcactaatg    3480
gacgttctgt ttgcttaact gaattaaaag gttatcatgt tactactggt gaacctgtat    3540
gccaaccacg tcgtcctaat agtcgtattg ataaagttcg ttatatgttc aacaaaatca    3600
```

```
cataataaaa aaaaaaaccc cgccctgac agggcggggt ttttttttta gttagttaga      3660
gatgtgtata agagacagct ggccatggaa tagactggag ggaggcggat aaagttgcag      3720
gaccacttct gcgctcggcc cttccggctg gctggtttat tgctgataaa tctggagccg      3780
gtgagcgtgg gtctcgcggt atcattgcag cactggggcc agatggtaag ccctcccgta      3840
tcgtagttat ctacacgacg gggagtcagg caactatgga tgaacgaaat agacagatcg      3900
ctgagatagg tgcctcactg attaagcatt ggtaactgtc agaccaagtt tactcatata      3960
tactttagat tgatttaaaa cttcattttt aatttaaaag gatctaggtg aagatccttt      4020
ttgataatct catgaccaaa atcccttaac gtgagttttc gttccactga gcgtcagacc      4080
ccttaataag atgatcttct tgagatcgtt ttggtctgcg cgtaatctct gctctgaaa      4140 acgaaaaaac cgccttgcag gcggttttt cgaaggttct ctgagctacc aactctttga      4200
accgaggtaa ctggcttgga ggagcgcagt caccaaaact tgtcctttca gtttagcctt      4260
aaccggcgca tgacttcaag actaactcct ctaaatcaat taccagtggc tgctgccagt      4320
ggtgcttttg catgtctttc cgggttggac tcaagacgat agttaccgga taaggcgcag      4380
cggtcggact gaacggggg ttcgtgcata cagtccagct tggagcgaac tgcctacccg      4440
gaactgagtg tcaggcgtgg aatgagacaa acgcggccat aacagcggaa tgacaccggt      4500
aaaccgaaag gcaggaacag gagagcgcac gaggagccg ccaggggaaa cgcctggtat      4560
ctttatagtc ctgtcgggtt tcgccaccac tgatttgagc gtcagatttc gtgatgcttg      4620 tcagggggc ggagcctatg gaaaaacggc tttgccgcgg ccctctcact tccctgttaa      4680
gtatcttcct ggcatcttcc aggaaatctc cgccccgttc gtaagccatt tccgctcgcc      4740
gcagtcgaac gaccgagcgt agcgagtcag tgagcgagga agcggaatat atcctgtatc      4800
acatattctg ctgacgcacc ggtgcagcct ttttctcct gccacatgaa gcacttcact      4860 gacacccctca tcagtgccaa catagtaagc cagtatacac tccgctagcg ctgaggtctg      4920
cctcgtgaag aaggtgttgc tgactcatac caggcctgaa tcgccccatc atccagccag      4980
aaagtgaggg agccacggtt gatgagagct ttgttgtagg tggaccagtt ggtgattttg      5040 aactttgct tgccacgga acggtctgcg ttgtcgggaa gatgcgtgat ctgatccttc      5100
aactcagcaa aagttcgatt tattcaacaa agccacgttg tgtctcaaaa tctctgatgt      5160
tacattgcac aagataaaaa tatatcatca tgaacaataa aactgtctgc ttacataaac      5220
agtaatacaa ggggtgttgc ccagctgtct cttatacaca tctccggctt atcggtcagt      5280
ttcacctgat ttacgtaaaa acccgcttcg gcgggttttt gcttttggag gggcagaaag      5340
atgaatgact gtccacgacg ctatacccaa agaaagcc                              5379
```

<210> SEQ ID NO 96
<211> LENGTH: 6932
<212> TYPE: DNA
<213> ORGANISM: Artificial Sequence
<220> FEATURE:
<223> OTHER INFORMATION: Synthetic Construct

<400> SEQUENCE: 96

```
ttctgaatta tgcggtaacg ttttcaaaat tgaatataca aaaaaacgtc aacgtttagc        60
ttatatacgt ctttatagtg gtgttttaca tttacgtgat agtgttcgtg ttagtgaaaa      120
agaaaagatt aaagttacag aaatgtatac ttctattaac ggtgaattat gcaaaattga      180
ccgtgcatat tcaggtgaaa ttgtaatttt acaaaacgaa tttcttaaac ttaatagtgt      240
```

-continued

```
acttggtgac acaaaacttt taccacaacg taagaaaatt gaaaatccac acccattact   300
tcaaacaaca gtagaaccaa gcaaacctga acaacgtgaa atgcttttag atgctctttt   360
agaaattagt gactctgacc cacttttacg ttactatgta gattctacta ctcatgaaat   420
tattctttct ttccttggta aagttcaaat ggaagttatt tctgcattat acaagaaaa    480
atatcatgtt gaaatcgaat aaaagaacc tactgtaatt tatatggaac gtccattaaa    540
aaatgctgaa tatacaattc atattgaagt tccaccaaat ccattttggg cttctattgg   600
tctttctgtt tctccacttc cacttggtag cggaatgcaa tatgaaagta gcgtaagttt   660
aggttatctt aatcaaagtt tccaaaacgc agttatggaa ggtattcgtt acggttgcga   720
acaaggttta tacggttgga atgttacaga ctgcaaaatc tgttttaagt atggactta    780
ctattcacct gtatcaacac ctgctgactt tcgtatgctt gcaccaattg ttttagaaca   840
agttttaaag aaagctggaa ctgaactttt agaaccatac ctttctttta aaatctatgc   900
accacaagaa tacttaagtc gtgcttataa cgatgcacct aaatactgtg ctaatattgt   960
tgatactcaa ttaagaaca acgaagtaat tttaagcgga gaaattcctg cacgttgtat  1020
tcaagaatat cgtagtgatt taacattttt cactaatgga cgttctgttt gcttaactga  1080
attaaaaggt tatcatgtta ctactggtga acctgtatgc caaccacgtc gtcctaatag  1140
tcgtattgat aaagttcgtt atatgttcaa caaaatcaca taataaaaa aaaaccccg    1200
cccctgacag ggcggggttt ttttttagt tagttagaga tgtgtataag agacagctgg   1260
ccatggaata gactggatgg aggcggataa agttgcagga ccacttctgc gctcggccct  1320
tccggctggc tggtttattg ctgataaatc tggagccggt gagcgtgggt ctcgcggtat  1380
cattgcagca ctggggccag atggtaagcc ctcccgtatc gtagttatct acacgacggg  1440
gagtcaggca actatggatg aacgaaatag acagatcgct gagataggtg cctcactgat  1500
taagcattgg taactgtcag accaagttta ctcatatata ctttagattg atttaaaact  1560
tcattttaa tttaaaagga tctaggtgaa gatccttttt gataatctca tgaccaaaat  1620
cccttaacgt gagttttcgt tccactgagc gtcagacccc ttaataagat gatcttcttg  1680
agatcgtttt ggtctgcgcg taatctcttg ctctgaaaac gaaaaaaccg ccttgcaggg  1740
cggttttcg aaggttctct gagctaccaa ctctttgaac cgaggtaact ggcttggagg   1800
agcgcagtca ccaaaacttg tcctttcagt ttagccttaa ccggcgcatg acttcaagac  1860
taactcctct aaatcaatta ccagtggctg ctgccagtgg tgcttttgca tgtctttccg  1920
ggttggactc aagacgatag ttaccggata aggcgcagcg gtcggactga acgggggggtt  1980
cgtgcataca gtccagcttg gagcgaactg cctacccgga actgagtgtc aggcgtggaa  2040
tgagacaaac gcggccataa cagcggaatg acaccggtaa accgaaaggc aggaacagga  2100
gagcgcacga gggagccgcc aggggaaacg cctggtatct ttatagtcct gtcgggtttc  2160
gccaccactg atttgagcgt cagatttcgt gatgcttgtc aggggggcgg agcctatgga  2220
aaaacggctt tgccgcggcc ctctcacttc cctgttaagt atcttcctgg catcttccag  2280
gaaatctccg ccccgttcgt aagccatttc cgctcgccgc agtcgaacga ccgagcgtag  2340
cgagtcagtg agcgaggaag cggaatatat cctgtatcac atattctgct gacgcaccgg  2400
tgcagccttt tttctcctgc cacatgaagc acttcactga caccctcatc agtgccaaca  2460
tagtaagcca gtatacactc cgctagcgct gaggtctgcc tcgtgaagaa ggtgttgctg  2520
actcatacca ggcctgaatc gccccatcat ccagccagaa agtgagggag ccacggttga  2580
tgagagcttt gttgtaggtg gaccagttgg tgattttgaa cttttgcttt gccacggaac  2640
```

```
ggtctgcgtt gtcgggaaga tgcgtgatct gatccttcaa ctcagcaaaa gttcgattta    2700
ttcaacaaag ccacgttgtg tctcaaaatc tctgatgtta cattgcacaa gataaaaata    2760
tatcatcatg aacaataaaa ctgtctgctt acataaacag taatacaagg ggtgttgccc    2820
agctgtctct tatacacatc tccggcttat cggtcagttt cacctgattt acgtaaaaac    2880
ccgcttcggc gggttttttgc ttttggaggg gcagaaagat gaatgactgt ccacgacgct    2940
atacccaaaa gaaagcccac agctaacacc acgtcgtccc tatctgctgc cctaggtcta    3000
tgagtggttg ctggataact ttacgggcat gcataaggct cgtatgatat attcagggag    3060
accacaacgg tttccctcta caaataattt tgtttaactt aaagaggag aaatactaga    3120 tggaccgtgt atatattcac cctttcatt tattagaagt actttccaa ggtccaatgg    3180 ctagtagtga ggatataatc aaagagttta tgcgttttaa agttcacatg gaaggttcag    3240
taaacggaca tgaatttgaa attgagggag aaggagaggg tcgtccgtac gaaggtacac    3300
aaacagcaaa gttaaaagta acaaaaggag gacctttacc atttgcatgg gatattcttt    3360
ctccacaatt tatgtatggt agtaaagcgt atgttaaaca cccggcagat ataccagact    3420
atttaaagtt gagttttccg gaaggattca aatgggaacg tgttatgaat tttgaagatg    3480
gtggtgttgt tacagttact caagatagta gcttacagga tggtgaattt atttacaaag    3540
taaaattacg tggtactaac ttcccgagcg atggtccagt aatgcaaaag aaaactatgg    3600
gatgggaggc tagttctgaa cgtatgtatc ctgaagacgg tgctttaaaa ggagaaatta    3660
acaacgtttt gaaacttaaa gatggtggac actacgatgc agaagttaaa actacatata    3720
aagctaaaaa gcctgttcag cttccgggtg cttataatgt gaatataaaa ttagatatca    3780
caagtcataa cgaagattat actattgttg aacagtatga aagagcagaa ggaagacatt    3840
ctacaggagc agcctaatca cacaggacta ctagatggag ggagtaaacg ataatgagga    3900
aggtttcttt agtgctcgtt tagaagtact tttccaaggt ccaatgtctc accttgctga    3960
gttggtcgca tcggccaaag ccgcaatctc gcaagcctcg gatgtcgcag ccttggacaa    4020
tgtccgtgtt gagtacttag gcaagaaggg acatttgacg ctccaaatga ctacgcttcg    4080
cgaacttcca cctgaggaac gcccagcagc tggcgccgtc attaatgagg ccaaggaaca    4140
agtccaacaa gccttgaacg cccgcaaggc cgagttggag agtgcagctt gaacgcccg    4200 cttggccgcc gagactatcg atgtatcctt gcctggccgc cgtatcgaga atggtggctt    4260
gcacccagtc acgcgcacga ttaccgcat tgagtcgttt tttggcgaac tcggtttcac    4320
tgttgctacg ggaccagaga ttgaggatga ctaccacaac tttgacgcat gaatatccc    4380 cggccatcat ccagcccgtg cagaccatga tacattttgg ttcgatacaa cgcgtttgtt    4440
gcgcacgcaa acgagtggtg tccagattcg tacgatgaag gcacaacaac ctccaatccg    4500
cattattgcc ccaggtcgcg tctaccgcaa tgattatgac caaacacata ctccaatgtt    4560
tcaccaaatg gagggcttga ttgtcgcacac gaatattagt ttcacgaatc ttaagggtac    4620
tttgcatgat ttttttgcgca acttttcga ggaggactta caaatccgtt tcgcccatc    4680 ttattttcca ttcacggagc catctgctga ggttgatgtt atgggcaaga atggcaagtg    4740
gttgagggtt ttgggttgtg aatggttca cccaaatgtt ttacgcaatg tcggtattga    4800
cccagaggtc tattccggct ttggctttgg aatgggaatg gaacgcttga caatgttacg    4860
ctatggtgtt acggatttgc gctcgttttt tgagaatgac ttgcgctttc ttaagcagtt    4920
caagtaagcc taagggccca agttcactta aaaaggagat taacaatgaa agcaatttc    4980
```

| gtactgaaac atcttaatca tgcacaggag actttctaat gaacgagaaa aatataaaac | 5040 |
| acagtcaaaa ctttattact tcaaaacata atatagataa aataatgaca aatataagat | 5100 |
| taaatgaaca tgataatatc tttgaaatcg gctcaggaaa aggccatttt acccttgaat | 5160 |
| tagtaaagag gtgtaatttc gtaactgcca ttgaaataga ccataaatta tgcaaaacta | 5220 |
| cagaaaataa acttgttgac cacgataatt tccaagtttt aaacaaggat atattgcagt | 5280 |
| ttaaatttcc taaaaccaa tcctataaaa tatatggtaa tataccttat aacataagta | 5340 |
| cggatataat acgcaaaatt gttttgata gtatagctaa tgagatttat ttaatcgtgg | 5400 |
| aatacgggtt tgctaaaaga ttattaaata caaaacgctc attggcatta cttttaatgg | 5460 |
| cagaagttga tatttctata ttaagtatgg ttccaagaga atattttcat cctaaaccta | 5520 |
| aagtgaatag ctcacttatc agattaagta gaaaaaaatc aagaatatca cacaaagata | 5580 |
| aacaaaagta taattatttc gttatgaaat gggttaacaa agaatacaag aaaatattta | 5640 |
| caaaaaatca atttaacaat tccttaaaac atgcaggaat tgacgattta aacaatatta | 5700 |
| gctttgaaca attcttatct cttttcaata gctataaatt atttaataag gccttagaag | 5760 |
| tactttttcca aggtccatac ggaggttttc tttaaagaga atataaaaag ccagattatt | 5820 |
| aatccggctt ttttattatt tgccggccag tctacatgta ctcttttga taaaaaattg | 5880 |
| gagattcctt tacaaatatg ctcttacgtg ctattattta agtgactatt taaaaggagt | 5940 |
| taataaatat gcggcaaggt attcttaaat aaactgtcaa tttgatagcg ggaacaaata | 6000 |
| attagatgtc cttttttagg agggcttagt tttttgtacc cagtttaaga ataccttat | 6060 |
| catgtgattc taaagtatcc agagaatatc tgtatgcttt gtatacctat ggttatgcat | 6120 |
| aaaaatcccg gtgataaaag tatttatcac tgggattttt atgccctttt gggtttttga | 6180 |
| atggaggaat actagatgaa aatcataaat atcggtgtat tagctcacgt tgatgcagga | 6240 |
| aaaacaacat taactgaatc acttttatat aactctggtg caattactga acttggttca | 6300 |
| gtagataaag gtactactcg tactgataat acattattag aacgtcaacg tggaatcaca | 6360 |
| attcaaacag gtatcacatc ttttcaatgg gaaaatacaa agtaaatat tatagataca | 6420 |
| cctggacaca tggatttcct tgcagaagta taccgtagtc tttcagtatt agatggtgct | 6480 |
| atttttactta tcagcgctaa agatggagtt caagctcaaa ctcgtatctt atttcacgca | 6540 |
| ttacgtaaaa tgggtattcc aacaattttc tttataaaca aaattgacca aaacggaatt | 6600 |
| gatttaagta cagtttatca agatatcaaa gaaaaacttt ctgctgaaat cgttattaaa | 6660 |
| caaaaagttg aattatacccc aaacgtttgc gtaacaaatt ttactgaatc agaacaatgg | 6720 |
| gatacagtta tagaaggtaa tgatgattta ttagaaaaat acatgtcagg taaatcatta | 6780 |
| gaagcattag aattagaaca agaagaaagt attcgtttcc aaaactgttc tttattccct | 6840 |
| ttataccatg gaagcgctaa aagtaacata ggtattgata acttaattga agttattact | 6900 |
| aacaaatttt attcttcaac tcatcgtggg cc | 6932 |

<210> SEQ ID NO 97
<211> LENGTH: 6927
<212> TYPE: DNA
<213> ORGANISM: Artificial Sequence
<220> FEATURE:
<223> OTHER INFORMATION: Synthetic Construct

<400> SEQUENCE: 97

| ttctgaatta tgcggtaacg ttttcaaaat tgaatataca aaaaaacgtc aacgtttagc | 60 |
| ttatatacgt ctttatagtg gtgttttaca tttacgtgat agtgttcgtg ttagtgaaaa | 120 |

```
agaaaagatt aaagttacag aaatgtatac ttctattaac ggtgaattat gcaaaattga      180
ccgtgcatat tcaggtgaaa ttgtaatttt acaaaacgaa tttcttaaac ttaatagtgt      240
acttggtgac acaaaacttt taccacaacg taagaaaatt gaaatccac acccattact       300 tcaaacaaca gtagaaccaa gcaaacctga caacgtgaa atgcttttag atgctctttt      360
agaaattagt gactctgacc cacttttacg ttactatgta gattctacta ctcatgaaat      420
tattctttct ttccttggta aagttcaaat ggaagttatt tctgcattat tacaagaaaa      480
atatcatgtt gaaatcgaat taaagaacc tactgtaatt tatatggaac gtccattaaa       540
aaatgctgaa tatacaattc atattgaagt tccaccaaat ccattttggg cttctattgg      600
tctttctgtt tctccacttc cacttggtag cggaatgcaa tatgaaagta gcgtaagttt      660
aggttatctt aatcaaagtt tccaaaacgc agttatggaa ggtattcgtt acggttgcga      720
acaaggttta tacggttgga atgttacaga ctgcaaaatc tgttttaagt atggacttta      780
ctattcacct gtatcaacac ctgctgactt tcgtatgctt gcaccaattg ttttagaaca      840
agttttaaag aaagctggaa ctgaactttt agaaccatac ctttcttta aaatctatgc       900 accacaagaa tacttaagtc gtgcttataa cgatgcacct aaatactgtg ctaatattgt      960
tgatactcaa ttaagaaca acgaagtaat tttaagcgga gaaattcctg cacgttgtat     1020
tcaagaatat cgtagtgatt taacatttt cactaatgga cgttctgttt gcttaactga     1080
attaaaaggt tatcatgtta ctactggtga acctgtatgc caaccacgtc gtcctaatag     1140
tcgtattgat aaagttcgtt atatgttcaa caaaatcaca taataaaaa aaaaaccccg      1200 cccctgacag ggcggggttt ttttttagt tagttagaga tgtgtataag agacagctgg     1260
ccatggaata gactggatgg aggcggataa agttgcagga ccacttctgc gctcggccct     1320
tccggctggc tggtttattg ctgataaatc tggagccggt gagcgtgggt ctcgcggtat     1380
cattgcagca ctggggccag atggtaagcc ctcccgtatc gtagttatct acacgacggg     1440
gagtcaggca actatggatg aacgaaatag acagatcgct gagataggtg cctcactgat     1500
taagcattgg taactgtcag accaagttta ctcatatata ctttagattg atttaaaact     1560
tcatttttaa tttaaaagga tctaggtgaa gatccttttt gataatctca tgaccaaaat     1620
cccttaacgt gagttttcgt tccactgagc gtcagacccc ttaataagat gatcttcttg     1680
agatcgtttt ggtctgcgcg taatctcttg ctctgaaaac gaaaaaaccg ccttgcaggg     1740 cggttttttcg aaggttctct gagctaccaa ctctttgaac cgaggtaact ggcttggagg     1800
agcgcagtca ccaaaacttg tcctttcagt ttagccttaa ccggcgcatg acttcaagac     1860
taactcctct aaatcaatta ccagtggctg ctgccagtgg tgcttttgca tgtctttccg     1920
ggttggactc aagacgatag ttaccggata aggcgcagcg gtcggactga acgggggtt     1980 cgtgcataca gtccagcttg gagcgaactg cctacccgga actgagtgtc aggcgtggaa     2040
tgagacaaac gcggccataa cagcggaatg acaccggtaa accgaaaggc aggaacagga     2100
gagcgcacga gggagccgcc aggggaaacg cctggtatct ttatagtcct gtcgggtttc     2160
gccaccactg atttgagcgt cagatttcgt gatgcttgtc agggggggcgg agcctatgga     2220 aaaacggctt tgccgcggcc ctctcacttc cctgttaagt atcttcctgg catcttccag     2280
gaaatctccg ccccgttcgt aagccatttc cgctcgccgc agtcgaacga ccgagcgtag     2340
cgagtcagtg agcgaggaag cggaatatat cctgtatcac atattctgct gacgcaccgg     2400
tgcagccttt tttctcctgc cacatgaagc acttcactga caccctcatc agtgccaaca     2460
```

```
tagtaagcca gtatacactc cgctagcgct gaggtctgcc tcgtgaagaa ggtgttgctg    2520
actcatacca ggcctgaatc gccccatcat ccagccagaa agtgagggag ccacggttga    2580
tgagagcttt gttgtaggtg gaccagttgg tgattttgaa cttttgcttt gccacggaac    2640
ggtctgcgtt gtcgggaaga tgcgtgatct gatccttcaa ctcagcaaaa gttcgattta    2700
ttcaacaaag ccacgttgtg tctcaaaatc tctgatgtta cattgcacaa gataaaaata    2760
tatcatcatg aacaataaaa ctgtctgctt acataaacag taatacaagg ggtgttgccc    2820
agctgtctct tatacacatc tccggcttat cggtcagttt cacctgattt acgtaaaaac    2880
ccgcttcggc gggttttttgc ttttggaggg gcagaaagat gaatgactgt ccacgacgct    2940
atacccaaaa gaaagcccac agctaacacc acgtcgtccc tatctgctgc cctaggtcta    3000
tgagtggttg ctggataact ttacgggcat gcataaggct cgtatgatat attcagggag    3060
accacaacgg tttccctcta caaataattt tgtttaactt taaagaggag aaatactaga    3120
tggaccgtgt atatattcac ccttttcatt tattagaagt acttttccaa ggtccaatgg    3180
ctagtagtga ggatataatc aaagagttta tgcgttttaa agttcacatg gaaggttcag    3240
taaacggaca tgaatttgaa attgagggag aaggagaggg tcgtccgtac gaaggtacac    3300
aaacagcaaa gttaaaagta acaaaaggag gacctttacc atttgcatgg gatattcttt    3360
ctccacaatt tatgtatggt agtaaagcgt atgttaaaca cccggcagat ataccagact    3420
atttaaagtt gagttttccg gaaggattca atgggaacg tgttatgaat tttgaagatg    3480
gtggtgttgt tacagttact caagatagta gcttacagga tggtgaattt atttacaaag    3540
taaaattacg tggtactaac ttcccgagcg atggtccagt aatgcaaaag aaaactatgg    3600
gatgggaggc tagttctgaa cgtatgtatc ctgaagacgg tgcttttaaa ggagaaatta    3660
acaacgtttt gaaacttaaa gatggtggac actacgatgc agaagttaaa actacatata    3720
aagctaaaaa gcctgttcag cttccgggtg cttataatgt gaatataaaa ttagatatca    3780
caagtcataa cgaagattat actattgttg aacagtatga aagagcagaa ggaagacatt    3840
ctacaggagc agcctaaggg cccaagttca cttaaaaagg agattaacaa tgaaagcaat    3900
tttcgtactg aaacatctta atcatgcaca ggagactttc taatgtctca ccttgctgag    3960
ttggtcgcat cggccaaagc cgcaatctcg caagcctcgg atgtcgcagc cttggacaat    4020
gtccgtgttg agtacttagg caagaaggga catttgacgc tccaaatgac tacgcttcgc    4080
gaacttccac ctgaggaacg cccagcagct ggcgccgtca ttaatgaggc caaggaacaa    4140
gtccaacaag ccttgaacgc ccgcaaggcc gagttggaga gtgcagcttt gaacgcccgc    4200
ttggccgccg agactatcga tgtatccttg cctggccgcc gtatcgagaa tggtggcttg    4260
cacccagtca cgcgcacgat tgaccgcatt gagtcgtttt ttggcgaact cggtttcact    4320
gttgctacgg gaccagagat tgaggatgac taccacaact ttgacgcatt gaatatcccc    4380
ggccatcatc cagcccgtgc agaccatgat acatttggt tcgatacaac gcgtttgttg    4440
cgcacgcaaa cgagtggtgt ccagattcgt acgatgaagg cacaacaacc tccaatccgc    4500
attattgccc caggtcgcgt ctaccgcaat gattatgacc aaacacatac tccaatgttt    4560
caccaaatgg agggcttgat tgtcgacacg aatattagtt tcacgaatct taagggtact    4620
ttgcatgatt ttttgcgcaa cttttcgag gaggacttac aaatccgttt tcgcccatct    4680
tattttccat tcacggagcc atctgctgag gttgatgtta tgggcaagaa tggcaagtgg    4740
ttggaggttt tgggttgtgg aatggttcac ccaaatgttt tacgcaatgt cggtattgac    4800
ccagaggtct attccggctt tggctttgga atgggaatgg aacgcttgac aatgttacgc    4860
```

```
tatggtgtta cggatttgcg ctcgttttt  gagaatgact tgcgctttct taagcagttc    4920
aagtaagcct tagaagtact tttccaaggt ccacgtccac ctggatttag tccttaaaaa    4980
gaggagaaat actagatgaa cgagaaaaat ataaaacaca gtcaaaactt tattacttca    5040
aaacataata tagataaaat aatgacaaat ataagattaa atgaacatga taatatcttt    5100
gaaatcggct caggaaaagg ccatttacc  cttgaattag taaagaggtg taatttcgta    5160
actgccattg aaatagacca taaattatgc aaaactacag aaaataaact tgttgaccac    5220
gataatttcc aagttttaaa caaggatata ttgcagttta aatttcctaa aaaccaatcc    5280
tataaaatat atggtaatat acctataac  ataagtacgg atataatacg caaaattgtt    5340
tttgatagta tagctaatga gatttattta atcgtggaat acgggtttgc taaaagatta    5400
ttaaatacaa aacgctcatt ggcattactt ttaatggcag aagttgatat ttctatatta    5460
agtatggttc caagagaata ttttcatcct aaacctaaag tgaatagctc acttatcaga    5520
ttaagtagaa aaaatcaag  aatatcacac aaagataaac aaaagtataa ttatttcgtt    5580
atgaaatggg ttaacaaaga atacaagaaa atatttacaa aaaatcaatt taacaattcc    5640
ttaaaacatg caggaattga cgatttaaac aatattagct ttgaacaatt cttatctctt    5700
ttcaatagct ataaattatt taataaggcc ttagaagtac ttttccaagg tccacatagt    5760
gatgctgtat ttacagataa cactcgttaa agagaatata aaaagccaga ttattaatcc    5820
ggctttttta ttatttgccg gccagtctac atgtactctt tttgataaaa aattggagat    5880
tcctttacaa atatgctctt acgtgctatt atttaagtga ctatttaaaa ggagttaata    5940
aatatgcggc aaggtattct taaataaact gtcaatttga tagcgggaac aaataattag    6000
atgtccttt  ttaggagggc ttagtttttt gtacccagtt taagaatacc tttatcatgt    6060
gattctaaag tatccagaga atatctgtat gctttgtata cctatggtta tgcataaaaa    6120
tcccggtgat aaaagtattt atcactggga ttttatgcc  ctttgggtt  tttgaatgga    6180
ggaatactag atgaaaatca taaatatcgg tgtattagct cacgttgatg caggaaaaac    6240
aacattaact gaatcacttt tatataactc tggtgcaatt actgaacttg gttcagtaga    6300
taaaggtact actcgtactg ataatacatt attagaacgt caacgtggaa tcacaattca    6360
aacaggtatc acatcttttc aatgggaaaa tacaaaagta aatattatag atacacctgg    6420
acacatggat ttccttgcag aagtataccg tagtctttca gtattagatg gtgctatttt    6480
acttatcagc gctaaagatg gagttcaagc tcaaactcgt atcttatttc acgcattacg    6540
taaaatgggt attccaacaa ttttctttat aaacaaaatt gaccaaaacg gaattgattt    6600
aagtacagtt tatcaagata tcaaagaaaa actttctgct gaaatcgtta ttaaacaaaa    6660
agttgaatta tacccaaacg tttgcgtaac aaatttact  gaatcagaac aatgggatac    6720
agttatagaa ggtaatgatg atttattaga aaaatacatg tcaggtaaat cattagaagc    6780
attagaatta gaacaagaag aaagtattcg tttccaaaac tgttctttat tcccctttata    6840
ccatggaagc gctaaaagta acataggtat tgataactta attgaagtta ttactaacaa    6900
attttattct tcaactcatc gtgggcc                                       6927
```

<210> SEQ ID NO 98
<211> LENGTH: 6906
<212> TYPE: DNA
<213> ORGANISM: Artificial Sequence
<220> FEATURE:
<223> OTHER INFORMATION: Synthetic Construct

```
<400> SEQUENCE: 98
ttctgaatta tgcggtaacg ttttcaaaat tgaatataca aaaaaacgtc aacgtttagc      60
ttatatacgt ctttatagtg gtgttttaca tttacgtgat agtgttcgtg ttagtgaaaa     120
agaaaagatt aaagttacag aaatgtatac ttctattaac ggtgaattat gcaaaattga     180
ccgtgcatat tcaggtgaaa ttgtaatttt acaaaacgaa tttcttaaac ttaatagtgt     240
acttggtgac acaaaacttt taccacaacg taagaaaatt gaaatccac acccattact      300
tcaaacaaca gtagaaccaa gcaaacctga acaacgtgaa atgcttttag atgctctttt     360
agaaattagt gactctgacc cacttttacg ttactatgta gattctacta ctcatgaaat     420
tattctttct ttccttggta aagttcaaat ggaagttatt tctgcattat tacaagaaaa     480
atatcatgtt gaaatcgaat taaaagaacc tactgtaatt tatatggaac gtccattaaa     540
aaatgctgaa tatacaattc atattgaagt tccaccaaat ccattttggg cttctattgg     600
tctttctgtt tctccacttc cacttggtag cggaatgcaa tatgaaagta gcgtaagttt     660
aggttatctt aatcaaagtt tccaaaacgc agttatggaa ggtattcgtt acggttgcga     720
acaaggttta tacggttgga atgttacaga ctgcaaaatc tgttttaagt atggactttta    780
ctattcacct gtatcaacac ctgctgactt tcgtatgctt gcaccaattg ttttagaaca     840
agttttaaag aaagctggaa ctgaacttt agaaccatac ctttcttta aaatctatgc       900
accacaagaa tacttaagtc gtgcttataa cgatgcacct aaatactgtg ctaatattgt     960
tgatactcaa ttaaagaaca acgaagtaat tttaagcgga gaaattcctg cacgttgtat    1020
tcaagaatat cgtagtgatt taacatttt cactaatgga cgttctgttt gcttaactga    1080
attaaaaggt tatcatgtta ctactggtga acctgtatgc caaccacgtc gtcctaatag    1140
tcgtattgat aaagttcgtt atatgttcaa caaaatcaca taataaaaaa aaaaccccg     1200
cccctgacag ggcggggttt tttttttagt tagttagaga tgtgtataag agacagctgg    1260
ccatggaata gactggatgg aggcggataa agttgcagga ccacttctgc gctcggccct    1320
tccggctggc tggtttattg ctgataaatc tggagccggt gagcgtgggt ctcgcggtat    1380
cattgcagca ctgggccag atggtaagcc ctcccgtatc gtagttatct acacgacggg     1440
gagtcaggca actatggatg aacgaaatag acagatcgct gagataggtg cctcactgat    1500
taagcattgg taactgtcag accaagttta ctcatatata ctttagattg atttaaaact    1560
tcattttta tttaaaagga tctaggtgaa gatcctttt gataatctca tgaccaaaat     1620
cccttaacgt gagttttcgt tccactgagc gtcagacccc ttaataagat gatcttcttg    1680
agatcgtttt ggtctgcgcg taatctcttg ctctgaaaac gaaaaaaccg ccttgcaggg    1740
cggtttttcg aaggttctct gagctaccaa ctcttgaac cgaggtaact ggcttggagg      1800
agcgcagtca ccaaaacttg tcctttcagt ttagccttaa ccggcgcatg acttcaagac    1860
taactcctct aaatcaatta ccagtggctg ctgccagtgg tgcttttgca tgtctttccg    1920
ggttggactc aagacgatag ttaccggata aggcgcagcg gtcggactga acgggggggtt   1980
cgtgcataca gtccagcttg gagcgaactg cctacccgga actgagtgtc aggcgtggaa    2040
tgagacaaac gcggccataa cagcggaatg acaccggtaa accgaaaggc aggaacagga    2100
gagcgcacga gggagccgcc aggggaaacg cctggtatct ttatagtcct gtcgggtttc    2160
gccaccactg atttgagcgt cagatttcgt gatgcttgtc aggggggcgg agcctatgga    2220
aaaacggctt tgccgcggcc ctctcacttc cctgttaagt atcttcctgg catcttccag    2280
gaaatctccg ccccgttcgt aagccatttc cgctcgccgc agtcgaacga ccgagcgtag    2340
```

```
cgagtcagtg agcgaggaag cggaatatat cctgtatcac atattctgct gacgcaccgg    2400
tgcagccttt tttctcctgc cacatgaagc acttcactga caccctcatc agtgccaaca    2460
tagtaagcca gtatacactc cgctagcgct gaggtctgcc tcgtgaagaa ggtgttgctg    2520
actcatacca ggcctgaatc gccccatcat ccagccagaa agtgagggag ccacggttga    2580
tgagagcttt gttgtaggtg gaccagttgg tgattttgaa cttttgcttt gccacggaac    2640
ggtctgcgtt gtcgggaaga tgcgtgatct gatccttcaa ctcagcaaaa gttcgattta    2700
ttcaacaaag ccacgttgtg tctcaaaatc tctgatgtta cattgcacaa gataaaaata    2760
tatcatcatg aacaataaaa ctgtctgctt acataaacag taatacaagg ggtgttgccc    2820
agctgtctct tatacacatc tccggcttat cggtcagttt cacctgattt acgtaaaaac    2880
ccgcttcggc gggttttttgc ttttggaggg gcagaaagat gaatgactgt ccacgacgct    2940
atacccaaaa gaaagcccac agctaacacc acgtcgtccc tatctgctgc cctaggtcta    3000
tgagtggttg ctggataact ttacgggcat gcataaggct cgtataatat attcagggag    3060
accacaacgg tttccctcta caaataattt tgtttaactt ttcacacagg actactagat    3120
gcgcacgtat acgttcgacc aggtcgaaaa ggcaatagag cagctttatc ctgattttac    3180
gattaatacc atagagataa gtggcgaagg taatgactgt atcgcatatg aaataaaccg    3240
ggatttcatc tttaaatttc caaagcatag tagggctct acgaatctgt ttaatgaagt     3300
caatatactc aaaaggattc acaataaact tcccctcccc atcccggagg tggtatttac    3360
cggcatgcca agtgaaacat accaaatgtc tttcgcagga tttaccaaaa tcaaaggcgt    3420
cccattaacc cctctgctac tcaataattt gccgaagcaa tctcaaaatc aggcagctaa    3480
ggacttggcg cgcttctat cagaactgca cagcataaac atttctggct tcaaatcaaa     3540
tttggtcctt gattttcgcg agaagataaa tgaagataat aaaaaaatta aaaagcttct    3600
atcgcgggaa cttaagggac cccagatgaa gatagtggat gatttttacc gggatatcct    3660
agagaacgaa atttacttca aatactatcc ttgtctaatc cataacgatt ttagctcaga    3720
ccatatcctt tttgatactg aaaaaaatac gatatgtggc ataattgatt ttggcgatgc    3780
agctatctct gaccccgaca atgattttat atcattaatg gaagatgatg aagaatacgg    3840
tatggaattt gtcagtaaaa tattaaacca ttacaaacat aaggatatac cgaccgtatt    3900
agaaaaatat cggatgaaag aaaaatactg gtccttcgaa aagataattt atggcaagga    3960
atatggatat atggattgat atgaggaggg ccttaatgaa attaggagca tcaaaatcaa    4020
ggccttagaa gtacttttcc aaggtccacg tccacctgga tttagtcctt aaaaagagga    4080
gaaatactag atggccgaag cacagaacga ccccttatta ccagggtaca gttttaatgc    4140
tcatttagtt gcaggactta ctccaattga ggctaatgga tatctggatt ttttttatcga    4200
ccgaccatta gggatgaaag gatatattct gaacctgaca attcgtggac aaggcgttgt    4260
taaaaaccaa gggcgagaat ttgtgtgtcg accaggagat attttgttat tcccacctgg    4320
ggagattcat cactacggaa gacatccaga ggcccgtgaa tgatatcacc aatgagtata    4380
ctttagacca cgtgcttact gacatgaatg actaaattga ccatccatat ttgctaacac    4440
tggattcttt cgtccagatg aagcacacca accacatttc tcagacttat ttggccagat    4500
aattaatgct ggccagggcg aaggccgtta gtgagttta ttagcaataa acttactaga     4560
gcagttgctt ttacgccgta tggaagcaat taatgagagt ctgcatcctc caatggataa    4620
ccgcgtccgt gaggcctgcc aatacatctc agaccactta gcggactcaa actttgatat    4680
```

| | |
|---|---|
| cgcttcagtg gcgcaacatg tatgtttgag tccaagtaga ttatcccatc tattccgtca | 4740 |
| acaacttggc atttcagtgc tttcatgacg tgaggaccag cgtatttctc aagcaaagtt | 4800 |
| actattgtca accacacgca tgccgatagc tacagtggga cgtaacgtag gatttgacga | 4860 |
| ccagctatat ttcagtcgag tctttaaaaa atgtacaggc gcttcaccat cagagtttag | 4920 |
| agctggatgc gaagaaaaag ttaacgatgt cgctgtgaag ttgtcggcct tagaagtact | 4980 |
| tttccaaggt ccagaccgtg tatatattca ccctttcat ttataatcac acaggactac | 5040 |
| tagatgatgt cgaggcttga taaatctaaa gttattaatt cagcgcttga gttactaaac | 5100 |
| gaggtgggga tagaaggact taaaacaaga aaactggctc aaaagctagg agtcgagcaa | 5160 |
| ccgacgttgt attgacatgt caaaaacaag cgcgccttgc tggacgctct tgctattgag | 5220 |
| atgcttgacc ggcaccatac ccacttttgt ccgcttgaag gcgaatcatg acaggatttt | 5280 |
| cttagaaaca atgccaaatc ttttaggtgc gcccttctct ctcatcgtga tggggcgaaa | 5340 |
| gtccatcttg gaacgcgccc gacggaaaaa caatatgaaa ccctggaaaa ccagcttgct | 5400 |
| tttctttgtc agcagggatt ttccctcgag aacgcgcttt atgcgctgtc agccgttggc | 5460 |
| cattttaccc ttggatgtgt cttggaagac caggagcatc aggtggccaa agaagaacgg | 5520 |
| gaaacgccga ccaccgattc tatgccagcg cttcttcgac aggccatcga acttttgaa | 5580 |
| caccagggag cggagcctgc tttccttttc ggtctggaac ttatcatatg tgggcttgaa | 5640 |
| aaacagctaa aatgcgaatc tggctcggcc ttagaagtac ttttccaagg tccagaggga | 5700 |
| gtaaacgata atgaggaagg tttctttagt gctcgtgaac aaaaacttat ttcagaggaa | 5760 |
| gacttataaa gagaatataa aaagccagat tattaatccg gcttttttat tatttgccgg | 5820 |
| ccagtctaca tgtactcttt ttgataaaaa attggagatt cctttacaaa tatgctctta | 5880 |
| cgtgctatta tttaagtgac tatttaaaag gagttaataa atatgcggca aggtattctt | 5940 |
| aaataaactg tcaatttgat agcgggaaca ataattaga tgtccttttt taggagggct | 6000 |
| tagtttttg tacccagttt aagaatacct ttatcatgtg attctaaagt atccagagaa | 6060 |
| tatctgtatg ctttgtatac ctatggttat gcataaaaat cccggtgata aagtatttta | 6120 |
| tcactgggat tttatgccc ttttgggttt ttgaatggag gaatactaga tgaaaatcat | 6180 |
| aaatatcggt gtattagctc acgttgatgc aggaaaaaca acattaactg aatcacttt | 6240 |
| ataactct ggtgcaatta ctgaacttgg ttcagtagat aaaggtacta ctcgtactga | 6300 |
| taatacatta ttagaacgtc aacgtggaat cacaattcaa acaggtatca catcttttca | 6360 |
| atgggaaaat acaaaagtaa atattataga tacacctgga cacatggatt tccttgcaga | 6420 |
| agtataccgt agtctttcag tattagatgg tgctatttta cttatcagcg ctaaagatgg | 6480 |
| agttcaagct caaactcgta tcttatttca cgcattacg aaaatgggta ttccaacaat | 6540 |
| tttctttata aacaaaattg accaaaacgg aattgattta agtacagttt atcaagatat | 6600 |
| caaagaaaaa ctttctgctg aaatcgttat taaacaaaaa gttgaattat acccaaacgt | 6660 |
| tgcgtaaca aattttactg aatcagaaca atgggataca gttatagaag gtaatgatga | 6720 |
| tttattagaa aaatacatgt caggtaaatc attagaagca ttagaattag aacaagaaga | 6780 |
| aagtattcgt ttccaaaact gttctttatt ccctttatac catggaagcg ctaaaagtaa | 6840 |
| cataggtatt gataacttaa ttgaagttat tactaacaaa ttttattctt caactcatcg | 6900 |
| tgggcc | 6906 |